US010300185B2

(12) United States Patent
Aboul-Hosn et al.

(10) Patent No.: US 10,300,185 B2
(45) Date of Patent: *May 28, 2019

(54) GUIDABLE INTRAVASCULAR BLOOD PUMP AND RELATED METHODS

(71) Applicant: MAQUET Cardiovascular LLC, Mahwah, NJ (US)

(72) Inventors: Walid N. Aboul-Hosn, Btekhnay (LB); William R. Kanz, Woodinville, WA (US); Bruce A. Baker, Placerville, CA (US)

(73) Assignee: MAQUET CARDIOVASCULAR LLC, Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,355

(22) Filed: Oct. 5, 2018

(65) Prior Publication Data

US 2019/0046706 A1    Feb. 14, 2019

Related U.S. Application Data

(60) Division of application No. 16/143,289, filed on Sep. 26, 2018, which is a division of application No.
(Continued)

(51) Int. Cl.
*A61M 1/12* (2006.01)
*A61M 1/10* (2006.01)
(Continued)

(52) U.S. Cl.
CPC .......... *A61M 1/125* (2014.02); *A61M 1/1008* (2014.02); *A61M 1/1029* (2014.02); *A61M 1/1031* (2014.02); *A61M 1/1096* (2014.02); *A61M 25/09* (2013.01); *A61M 1/101* (2013.01); *A61M 1/102* (2014.02); *A61M 1/1012* (2014.02);
(Continued)

(58) Field of Classification Search
CPC .. A61M 1/1008; A61M 1/101; A61M 1/1012; A61M 1/1013; A61M 1/102; A61M 1/1029; A61M 1/1031; A61M 1/1034; A61M 1/1086; A61M 1/1096; A61M 1/122; A61M 1/125; A61M 2025/0177;
(Continued)

(56) References Cited

U.S. PATENT DOCUMENTS 3,585,983 A    6/1971    Kantrowitz et al.
3,602,009 A    8/1971    Powell
(Continued)

FOREIGN PATENT DOCUMENTS

CA    2256427 A    10/1998
CA    2349483 A1   6/2000
(Continued)

OTHER PUBLICATIONS

Maq Rebuttal Validity Contentions Ex. A6, Case No. 1:16-cv-10914-FDS (dated Oct. 9, 2018).
(Continued)

*Primary Examiner* — Adam Marcetich

(57) ABSTRACT

An improved intravascular blood pump and related methods involving the broad inventive concept of equipping the intravascular blood pump with guiding features such that the intravascular blood pump can be selectively positioned at a predetermined location within the circulatory system of a patient.

23 Claims, 37 Drawing Sheets

Related U.S. Application Data

16/138,788, filed on Sep. 21, 2018, now Pat. No. 10,238,783, which is a division of application No. 15/675,310, filed on Aug. 11, 2017, which is a division of application No. 14/966,669, filed on Dec. 11, 2015, now Pat. No. 9,789,238, which is a division of application No. 14/543,815, filed on Nov. 17, 2014, now Pat. No. 9,327,068, which is a continuation of application No. 12/772,810, filed on May 3, 2010, now Pat. No. 8,888,728, which is a continuation of application No. 11/375,926, filed on Mar. 15, 2006, now Pat. No. 7,731,675, which is a division of application No. 10/070,178, filed as application No. PCT/US00/24515 on Sep. 1, 2000, now Pat. No. 7,022,100.

(60) Provisional application No. 60/152,249, filed on Sep. 3, 1999.

(51) Int. Cl.
*A61M 25/01* (2006.01)
*A61M 25/09* (2006.01)

(52) U.S. Cl.
CPC ......... *A61M 1/1013* (2014.02); *A61M 1/1034* (2014.02); *A61M 1/1086* (2013.01); *A61M 1/122* (2014.02); *A61M 2025/0177* (2013.01); *A61M 2025/0183* (2013.01); *A61M 2205/3348* (2013.01); *Y10S 415/90* (2013.01)

(58) Field of Classification Search
CPC .. A61M 2025/0183; A61M 2205/3348; A61M 25/09; Y10S 415/90
See application file for complete search history.

(56) References Cited

U.S. PATENT DOCUMENTS

| | | |
|---|---|---|
| 3,724,274 A | 4/1973 | Millar |
| 3,879,516 A | 4/1975 | Wolvek |
| 3,904,901 A | 9/1975 | Renard et al. |
| 3,966,358 A | 6/1976 | Heimes et al. |
| 3,995,617 A | 12/1976 | Watkins et al. |
| 4,135,253 A | 1/1979 | Reich et al. |
| 4,153,048 A | 5/1979 | Magrini |
| 4,391,547 A | 7/1983 | Jackson et al. |
| 4,392,836 A | 7/1983 | Sugawara |
| 4,413,989 A | 11/1983 | Schjeidahl et al. |
| 4,468,224 A | 8/1984 | Enzmann et al. |
| 4,479,497 A | 10/1984 | Forgurty |
| 4,508,535 A | 4/1985 | Joh et al. |
| 4,591,355 A | 5/1986 | Hilse |
| 4,625,712 A | 12/1986 | Wampler |
| 4,679,558 A | 7/1987 | Kensey et al. |
| 4,686,982 A | 8/1987 | Nash |
| 4,692,148 A | 9/1987 | Kantrowitz et al. |
| 4,696,667 A | 9/1987 | Masch |
| 4,704,121 A | 11/1987 | Moise |
| 4,722,348 A | 2/1988 | Ligtenberg et al. |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,764,324 A | 8/1988 | Burnham |
| 4,769,005 A | 9/1988 | Ginsburg et al. |
| 4,817,586 A | 4/1989 | Wampler |
| 4,846,152 A | 7/1989 | Wampler et al. |
| 4,858,810 A | 8/1989 | Intlekofer et al. |
| 4,895,557 A | 1/1990 | Moise et al. |
| 4,908,012 A | 3/1990 | Moise et al. |
| 4,909,781 A | 3/1990 | Husted |
| 4,917,102 A | 4/1990 | Miller et al. |
| 4,919,647 A | 4/1990 | Nash |
| 4,944,722 A | 7/1990 | Carriker et al. |
| 4,944,745 A | 7/1990 | Sogard et al. |
| 4,955,856 A | 9/1990 | Phillips |
| 4,964,839 A | 10/1990 | Gloor |
| 4,969,865 A | 11/1990 | Hwang et al. |
| 4,985,022 A | 1/1991 | Fearnot et al. |
| 4,990,134 A | 2/1991 | Auth et al. |
| 5,017,103 A | 5/1991 | Dahl |
| 5,030,204 A | 7/1991 | Badger et al. |
| 5,040,944 A | 8/1991 | Cook |
| 5,041,131 A | 8/1991 | Nagase |
| 5,044,897 A | 9/1991 | Dorman |
| 5,061,256 A | 10/1991 | Wampler |
| 5,061,273 A | 10/1991 | Yock |
| 5,092,844 A | 3/1992 | Schwartz et al. |
| 5,092,879 A | 3/1992 | Jarvik |
| 5,106,363 A | 4/1992 | Nobuyoshi |
| 5,108,411 A | 4/1992 | McKenzie |
| 5,112,292 A | 5/1992 | Hwang et al. |
| 5,112,349 A | 5/1992 | Summers et al. |
| 5,135,535 A | 8/1992 | Kramer |
| 5,137,513 A | 8/1992 | McInnes et al. |
| 5,160,321 A | 11/1992 | Sahota |
| 5,163,910 A | 11/1992 | Schwartz et al. |
| 5,169,378 A | 12/1992 | Figuera |
| 5,179,862 A | 1/1993 | Lynnworth |
| 5,199,950 A | 4/1993 | Schmitt et al. |
| 5,211,546 A | 5/1993 | Isaacson et al. |
| 5,221,256 A | 6/1993 | Mahurkar |
| 5,234,407 A | 8/1993 | Teirsten et al. |
| 5,250,059 A | 10/1993 | Andreas et al. |
| 5,275,580 A | 1/1994 | Yamazaki |
| 5,287,858 A | 2/1994 | Hammerslag et al. |
| 5,300,112 A | 4/1994 | Barr |
| 5,314,407 A | 5/1994 | Auth et al. |
| 5,334,142 A | 8/1994 | Paradis |
| 5,336,184 A | 8/1994 | Teirsten |
| 5,372,138 A | 12/1994 | Crowley et al. |
| 5,376,114 A | 12/1994 | Jarvik |
| 5,405,383 A | 4/1995 | Barr |
| 5,421,338 A | 6/1995 | Crowley |
| 5,435,308 A | 7/1995 | Gallup et al. |
| 5,476,450 A | 12/1995 | Ruggio |
| 5,484,412 A | 1/1996 | Pierpont |
| 5,507,725 A | 4/1996 | Savage et al. |
| 5,516,336 A | 5/1996 | McInnes et al. |
| 5,643,215 A | 7/1997 | Fuhrman et al. |
| 5,678,306 A | 10/1997 | Bozeman et al. |
| 5,692,882 A | 12/1997 | Bozeman, Jr. et al. |
| 5,697,948 A | 12/1997 | Marin et al. |
| 5,711,753 A | 1/1998 | Pacella et al. |
| 5,741,234 A | 4/1998 | Aboul-Hosn |
| 5,746,575 A | 5/1998 | Westphal et al. |
| 5,746,709 A | 5/1998 | Rom et al. |
| 5,746,758 A | 5/1998 | Nordgren et al. |
| 5,749,855 A | 5/1998 | Reitan |
| 5,755,687 A | 5/1998 | Donlon |
| 5,762,624 A | 6/1998 | Peters |
| 5,776,190 A | 7/1998 | Jarvik |
| 5,797,948 A | 8/1998 | Dunham |
| 5,810,088 A | 9/1998 | Lamirand et al. |
| 5,810,758 A | 9/1998 | Yamazaki et al. |
| 5,814,004 A | 9/1998 | Tamari |
| 5,824,070 A | 10/1998 | Jarvik |
| 5,827,229 A | 10/1998 | Auth et al. |
| 5,827,267 A | 10/1998 | Savage et al. |
| 5,851,174 A | 12/1998 | Jarvik et al. |
| 5,863,179 A | 1/1999 | Westphal et al. |
| 5,888,241 A | 3/1999 | Jarvik |
| 5,911,685 A | 6/1999 | Siess et al. |
| 5,911,702 A | 6/1999 | Romley et al. |
| 5,921,913 A | 7/1999 | Siess |
| 5,928,132 A | 7/1999 | Leschinsky |
| 5,928,181 A | 7/1999 | Colman et al. |
| 5,938,645 A | 8/1999 | Gordon |
| 5,938,672 A | 8/1999 | Nash |
| 5,947,892 A | 9/1999 | Benkowski et al. |
| 5,957,672 A | 9/1999 | Aber |

(56) References Cited

U.S. PATENT DOCUMENTS

| | | |
|---|---|---|
| 5,964,694 A | 10/1999 | Siess et al. |
| 5,965,089 A | 10/1999 | Jarvik et al. |
| 6,001,078 A | 12/1999 | Reekers |
| 6,007,478 A | 12/1999 | Seiss et al. |
| 6,058,593 A | 5/2000 | Siess |
| 6,066,100 A | 5/2000 | Willard et al. |
| 6,071,093 A | 6/2000 | Hart |
| 6,083,260 A | 7/2000 | Aboul-Hosn |
| 6,086,570 A | 7/2000 | Aboul-Hosn |
| 6,093,001 A | 7/2000 | Burgreen et al. |
| 6,113,536 A | 9/2000 | Aboul-Hosn |
| 6,116,862 A | 9/2000 | Rau et al. |
| 6,123,659 A | 9/2000 | Le Blanc et al. |
| 6,123,725 A | 9/2000 | Aboul-Hosn |
| 6,129,704 A | 10/2000 | Forman et al. |
| 6,136,025 A | 10/2000 | Barbut et al. |
| 6,139,487 A | 10/2000 | Siess |
| 6,146,354 A | 11/2000 | Beil |
| 6,152,704 A | 11/2000 | Aboul-Hosn et al. |
| 6,171,253 B1 | 1/2001 | Bullister et al. |
| 6,176,822 B1 | 1/2001 | Nix et al. |
| 6,176,848 B1 | 1/2001 | Rau et al. |
| 6,183,220 B1 | 2/2001 | Ohara et al. |
| 6,197,001 B1 | 3/2001 | Wilson et al. |
| 6,210,133 B1 | 4/2001 | Aboul-Hosn et al. |
| 6,210,397 B1 | 4/2001 | Aboul-Hosn et al. |
| 6,217,541 B1 | 4/2001 | Yu |
| 6,228,063 B1 | 5/2001 | Aboul-Hosn |
| 6,234,960 B1 | 5/2001 | Aboul-Hosn et al. |
| 6,245,007 B1 | 6/2001 | Bedingham et al. |
| 6,248,091 B1 | 6/2001 | Voelker |
| 6,287,319 B1 | 9/2001 | Aboul-Hosn et al. |
| 6,290,689 B1 | 9/2001 | Delaney et al. |
| 6,295,877 B1 | 10/2001 | Aboul-Hosn et al. |
| 6,336,939 B1 | 1/2002 | Yamazaki et al. |
| 6,346,120 B1 | 2/2002 | Yamazaki et al. |
| 6,354,814 B1 | 3/2002 | Kaufmann et al. |
| 6,395,026 B1 | 5/2002 | Aboul-Hosn et al. |
| 6,440,158 B1 | 8/2002 | Saab |
| 6,532,964 B2 | 3/2003 | Aboul-Hosn et al. |
| 6,533,716 B1 | 3/2003 | Schmitz Rode et al. |
| 6,544,216 B1 | 4/2003 | Sammler et al. |
| 6,572,530 B1 | 6/2003 | Araki et al. |
| 6,592,567 B1 | 7/2003 | Levin et al. |
| 6,613,008 B2 | 9/2003 | Aboul-Hosn et al. |
| 6,673,040 B1 | 1/2004 | Samson et al. |
| 6,709,418 B1 | 3/2004 | Aboul-Hosn et al. |
| 6,716,189 B1 | 4/2004 | Jarvik et al. |
| 6,733,459 B1 | 5/2004 | Atsumi |
| 6,849,068 B1 | 2/2005 | Bagaoisan et al. |
| 6,926,662 B1 | 8/2005 | Aboul-Hosn et al. |
| 7,022,100 B1 | 4/2006 | Aboul-Hosn et al. |
| 7,517,352 B2 | 4/2009 | Evans et al. |
| 7,731,675 B2 | 6/2010 | Aboul-Hosn et al. |
| 7,785,246 B2 | 8/2010 | Aboul-Hosn et al. |
| 7,998,054 B2 | 8/2011 | Bolling |
| 8,540,615 B2 | 9/2013 | Aboul-Hosn et al. |
| 8,545,447 B2 | 10/2013 | Demarais et al. |
| 8,613,777 B2 | 12/2013 | Siess et al. |
| 8,721,517 B2 | 5/2014 | Zeng et al. |
| 8,834,344 B2 | 9/2014 | Aboul-Hosn et al. |
| 8,888,728 B2 | 11/2014 | Aboul-Hosn et al. |
| 9,327,068 B2 | 5/2016 | Aboul-Hosn et al. |
| 9,545,468 B2 | 1/2017 | Aboul-Hosn et al. |
| 9,561,314 B2 | 2/2017 | Aboul-Hosn et al. |
| 9,597,437 B2 | 3/2017 | Aboul-Hosn et al. |
| 9,789,238 B2 | 10/2017 | Aboul-Hosn et al. |
| 2001/0027287 A1 | 10/2001 | Shmulewitz et al. |
| 2002/0183628 A1 | 12/2002 | Reich et al. |
| 2003/0023201 A1 | 1/2003 | Aboul-Hosn et al. |
| 2003/0065271 A1 | 4/2003 | Khoury |
| 2003/0088151 A1 | 5/2003 | Kung et al. |
| 2003/0100816 A1 | 5/2003 | Siess |
| 2003/0187322 A1 | 10/2003 | Siess |
| 2003/0205233 A1 | 11/2003 | Aboul-Hosn et al. |
| 2004/0097995 A1 | 5/2004 | Nash et al. |
| 2005/0049696 A1 | 3/2005 | Siess et al. |
| 2007/0118072 A1 | 5/2007 | Nash |
| 2009/0024212 A1 | 1/2009 | Siess et al. |
| 2013/0304158 A1 | 11/2013 | Zarinetchi et al. |

FOREIGN PATENT DOCUMENTS

| | | |
|---|---|---|
| CA | 2352234 A1 | 6/2000 |
| CA | 2361972 A1 | 8/2000 |
| CN | 1222862 A | 7/1999 |
| CZ | 200000007 A3 | 5/2000 |
| DE | 2355966 A | 5/1975 |
| DE | 4016013 A1 | 11/1991 |
| DE | 4105278 A1 | 8/1992 |
| DE | 29604787 U1 | 10/1996 |
| DE | 19622335 A1 | 12/1997 |
| DE | 19626224 A1 | 1/1998 |
| DE | 19821307 C1 | 10/1999 |
| DE | 10017147 A1 | 10/2001 |
| DE | 10018424 A1 | 10/2001 |
| EP | 0280225 A2 | 8/1988 |
| EP | 0364293 A2 | 4/1990 |
| EP | 0445782 A1 | 9/1991 |
| EP | 0157859 B1 | 4/1992 |
| EP | 0611582 A2 | 8/1994 |
| EP | 764448 A2 | 3/1997 |
| EP | 0810002 A1 | 12/1997 |
| EP | 0884064 A2 | 12/1998 |
| EP | 0916359 B1 | 5/1999 |
| JP | H04126158 A | 4/1992 |
| JP | H-0999092 A | 4/1997 |
| JP | 2002-514472 A | 5/2002 |
| WO | WO 89/05164 A1 | 5/1989 |
| WO | WO 1994 005347 A1 | 3/1994 |
| WO | WO 97/37697 A1 | 10/1997 |
| WO | WO 1997 037696 A1 | 10/1997 |
| WO | WO 97/46270 A1 | 12/1997 |
| WO | WO 1997 049440 A2 | 12/1997 |
| WO | WO 99/02204 A1 | 1/1999 |
| WO | WO 1999 044651 A1 | 9/1999 |
| WO | WO 99/58170 A1 | 11/1999 |
| WO | WO 99/59652 A1 | 11/1999 |
| WO | WO 1999/058170 A1 | 11/1999 |
| WO | WO 00/12148 A1 | 3/2000 |
| WO | WO 00/18448 A1 | 4/2000 |
| WO | WO 00/19097 A1 | 4/2000 |
| WO | WO 2000029056 A2 | 5/2000 |
| WO | WO 00/37139 A1 | 6/2000 |
| WO | WO 2000 029056 A1 | 6/2000 |
| WO | WO 2000033047 A1 | 6/2000 |
| WO | WO 2000037139 A1 | 6/2000 |
| WO | WO 2000 043053 A1 | 7/2000 |
| WO | WO 00/44417 A1 | 8/2000 |
| WO | WO 2000053240 A1 | 9/2000 |
| WO | WO 00/69489 A1 | 11/2000 |
| WO | WO 2000074748 A1 | 12/2000 |
| WO | WO 2000029056 A3 | 1/2001 |
| WO | WO 2001039817 A2 | 6/2001 |
| WO | WO 01/78807 A1 | 10/2001 |
| WO | WO 2001039817 A3 | 1/2002 |

OTHER PUBLICATIONS

Maq Rebuttal Validity Contentions Ex. A1, Case No. 1:16-cv-10914-FDS (dated Oct. 9, 2018).
Maq Rebuttal Validity Contentions Ex. A3, Case No. 1:16-cv-10914-FDS (dated Oct. 9, 2018).
Maq Rebuttal Validity Contentions Ex. A5, Case No. 1:16-cv-10914-FDS (dated Oct. 9, 2018).
Maq Rebuttal Validity Contentions Ex. A7, Case No, 1:16-cv-10914-FDS (dated Oct. 9, 2018).
Maq Rebuttal Validity Contentions Ex. A2, Case No. 1:16-cv-10914-FDS (dated Oct. 9, 2018).
Maq Rebuttal Validity Contentions Ex. A4, Case No. 1:16-cv-10914-FDS (dated Oct. 9, 2018).
Maq Rebuttal Validity Contentions, Case No. 1:16-cv-10914-FDS (dated Oct. 9, 2018).

(56) References Cited

OTHER PUBLICATIONS

Maq 1 Ex. A1—Invalidity by PCT Pub. No. WO 99/02204 ("Aboul-Hosn"), Case No. 1:16-cv-10914-FDS (dated Sep. 8, 2017).
Maq 1 Ex. A2—Invalidity by "The Hemopump References", Case No. 1:16-cv-10914-FDS (dated Sep. 8, 2017).
Maq 1 Ex. A3—Invalidity based on "Jegaden", Case No. 1:16-cv-10914-FDS (daed Sep. 8, 2017).
Maq 1 Ex. A4—Invalidity by U.S. Pat. No. 6,248,091 ("Voelker"), Case No. 1:16-cv-10914-FDS (dated Sep. 8, 2017).
Maq 1 Ex. A5—Invalidity by U.S. Pat. No. 5,921,913 ("Siess"), Case No. 1:16-cv-10914-FDS (dated Sep. 8, 2017).
Maq 1 Ex. A6—Invalidity by U.S. Pat. No. 6,544,216 B1 ("Sammler"), Case No. 1:16-cv-10914-FDS (dated Sep. 8, 2017).
Maq 1 Ex. A7—Invalidity by U.S. Pat. No. 6,247,007 B1 ("Bedingham"), Case No. 1:16-cv-10914-FDS (dated Sep. 8, 2017).
Maq II Ex. A1—238 Invalidity—Aboul-Hosn Chart, Case No. 1:17-cv-12311-FDS (dated Aug. 3, 2018).
Maq II Ex. A2—238 Invalidity—Hemopump Chart, Case No. 1:17-cv-12311-FDS (dated Aug. 3, 2018).
Maq II Ex. A3—238 Invalidity—Jegaden Chart, Case No, 1:17-cv-12311-FDS (dated Aug. 3, 2018).
Maq II Ex. A4—238 Invalidity—Voelker Chart, Case No. 1:17-cv-12311-FDS (dated Aug. 3, 2018).
Maq II Ex. A5—238 Invalidity—Siess Chart, Case No. 1:17-cv-12311-FDS (dated Aug. 3, 2018).
Maq II Ex. A6—238 Invalidity—Bedingham Chart, Case No. 1:17-cv-12311-FDS (dated Aug. 3, 2018).
Abiomed's Surreply to Maquet's Motion for Reconsideration dated Oct. 26, 2018, Case No. 1:16-cv-10914-FDS.
Sur-Response of Maquet Cardiovascular LLC Concerning Its Motion For Reconsideration and/or Clarification of Claim Construction Regarding "Passing Purge Fluid" Terms dated Nov. 1. 2018, Case No. 1:16-cv-10914-FDS.
Abiomed's Opposition to Maquet's Motion for Reconsideration dated Oct. 5, 2018, Case No. 1:16-cv-10914-FDS.
Reply Memorandum of Law in Further Support of Maquet Cardiovascular LLC's Motion for Reconsideration and/or Clarification of Order on Claim Construction Regarding "Passing Purge Fluid" Terms dated Oct. 17, 2018, Case No. 1:16-cv-10914-FDS.
U.S. Appl. No. 15/675,310, filed Aug. 11, 2017, 2017/0340791 A1, Published.
U.S. Appl. No. 15/675,310, filed Aug. 11, 2017, Aboul-Hosn et al.
U.S. Appl. No. 16/153,355, filed Oct. 5, 2018, Aboul-Hosn et al.
U.S. Appl. No. 16/153,473, filed Oct. 5, 2018, Aboul-Hosn et al.
U.S. Appl. No. 16/153,619, filed Oct. 5, 2018, Aboul-Hosn et al.
U.S. Appl. No. 16/167,400, filed Oct. 22, 2018, Aboul-Hosn et al.
Abiomed Inc., Abiomed R&D, Inc. and Abiomed Europe GmbH's Preliminary Invalidity Contentions, No. 1:16-cv-10914-FDS, dated Sep. 8, 2017 (redacted).
Abiomed Inc., Abiomed R&D, Inc. and Abiomed Europe GmbH's Preliminary Invalidity Contentions, No. 1:17-cv-12311-FDS, dated Aug. 3, 2018 (redacted).
Abiomed's Opening Claim Construction Brief, No. 1:16-cv-10914-FDS, filed Dec. 15, 2017.
Abiomed's Opposition to Maquet's Motion for Reconsideration, 1:16-cv-10914- FDS, filed Oct. 5, 2018.
Abiomed's Rebuttal Claim Construction Brief, No. 1:16-cv-10914-FDS, filed Jan. 26, 2018.
Abou-Awdi N. L., et al., Hemopump Left Ventricular Support in the Peripartum Cardiomyopathy Patient, 8 J. Cardiovascular Nursing, Issue 2 (Jan. 1994) ("Abou-Awdi").
Akdis, M. et al., *Blood Pumps for Circulatory Support*, Perfusion 15 (2000).
Andre F. Cournand et al., Nobel Prize in Physiology or Medicine 1956, Nobel Prize, http://www.nobelprize.org/nobel_prizes/medicine/laureates/ (last visited Jan. 25, 2017).
Andrew F. Cournand, Control of the pulmonary circulation in man with some remarks on methodology, Nobel Lecture, Dec. 11, 1956, p. 531 and p. 533.
Antaki, et al., In Vivo Evaluation of the Nimbus Axial Flow Ventricular Assist System: Criteria and Methods, ASAIO J., M231-36 (1993).
Attar, S., *New developments in cardiac assist devices*, Surgical Science Series (1985).
B. Meyns et al., "Coronary Artery Bypass Graft with Biventricular Microaxial Pumps", Journal of Perfusion, Jul. 1999; 14(4):pp. 287-290.
B. Meyns et al., Micro pumps to Support the Heart During CABG, European Journal of Cardiothorac Surg (2000) 17 (2): pp. 169-174.
Butler, et al., Development of a 14 Fr. Size Hemopump, Ann. Int'l Conf. IEEE Eng'g in Med. & Bio Sci., 12(2): 735-36 (1990).
Butler, et al., Development of an Axial Flow Blood Pump LVAS, ASAIO J., M296-300 (1992).
Casimir-Ahn, H. et al., *Clinical Use of the Hemopump Cardiac Assist System for Circulatory Support*, The Annals of Thoracic Surgery, vol. 59 (1995), pp. 539-545.
Collins Declaration IPR-2017-01025.
Collins Declaration IPR-2017-01026.
Collins Declaration IPR-2017-01027.
Collins Declaration IPR-2017-01028.
Collins Declaration IPR-2017-01029.
Collins Declaration IPR-2017-01201.
Collins Declaration IPR-2017-01202.
Collins Declaration IPR-2017-01203.
Collins Declaration IPR-2017-01204.
Collins Declaration IPR-2017-01205.
Collins Declaration IPR-2017-01207.
Collins Declaration IPR-2017-01208.
Collins Declaration IPR-2017-01209.
Collins Declaration IPR-2017-01253.
Colombo, Selecton of Coronary Stents, J. Am. Coll. Cardiology 40(6); 1021-33 (2002).
Compendium of Technical and Scientific Information for the Hemopump Temporary Cardia Assist System, 1988 (15 pages).
Complaint from *Abiomet Inv. V. Maquet Cardiovascular*, Case No. 1:16-cv-10914, filed in Dist. of Mass. on May 19, 2016.
Cortis, B. S., *From Augiography to Angioscopy: Informal Discussion*, Texas Heart Institute Journal (1986).
Decision Denying Institution of Inter Partes Review Case IPR 2017-01025.
Decision Denying Institution of Inter Partes Review IPR2017-01208.
Decision Denying Institution of Inter Partes Review IPR2017-01209.
Decision Denying Institution of Inter Partes Review IPR2017-02134.
Decision Denying Institution of Inter Partes Review IPR2017-02135.
Decision Denying Institution of Inter Partes Review IPR2017-02150.
Decision Denying Institution of Inter Partes Review IPR2017-02151.
Decision Denying Institution of Inter Partes Review IPR2017-02152.
Decision Denying Institution of Inter Partes Review IPR2017-02153.
Decision Denying Inter Partes Review IPR2017-01026.
Decision Denying Inter Partes Review IPR2017-01027.
Decision Denying Inter Partes Review IPR2017-01028.
Decision Denying Inter Partes Review IPR2017-01029.
Decision Denying Inter Partes Review IPR2017-01201.
Decision Denying Inter Partes Review IPR2017-01202.
Decision Denying Inter Partes Review IPR2017-01203.
Decision Denying Inter Partes Review IPR2017-01204.
Decision Denying Inter Partes Review IPR2017-01205.
Decision Denying Inter Partes Review IPR2017-01207.
Decision Denying Inter Partes Review IPR2017-01253.
Decision Denying Petitioner's Requests for Rehearing IPR2017-01026.
Decision Denying Petitioner's Requests for Rehearing IPR2017-01027.

(56) References Cited

OTHER PUBLICATIONS

Decision Denying Petitioner's Requests for Rehearing IPR2017-01028.
Decision Denying Petitioner's Requests for Rehearing IPR2017-01029.
Decision Denying Petition's Request for Rehearing IPR2017-01025.
Decision from the Patent Trial and Appeal Board, USPTO, appeal No. 2013-001967 for US Patent Application Serial No. 10-556423 dated Sep. 30, 2015 (4 pages).
Declaration of Kiersten Batzli—IPR-2017-01025.
Declaration of Kiersten Batzli—IPR-2017-01026.
Declaration of Kiersten Batzli—IPR-2017-01027.
Declaration of Kiersten Batzli—IPR-2017-01028.
Declaration of Kiersten Batzli—IPR-2017-01029.
Declaration of Kiersten Batzli—IPR-2017-01201.
Declaration of Kiersten Batzli—IPR-2017-01202.
Declaration of Kiersten Batzli—IPR-2017-01203.
Declaration of Kiersten Batzli—IPR-2017-01204.
Declaration of Kiersten Batzli—IPR-2017-01205.
Declaration of Kiersten Batzli—IPR-2017-01207.
Declaration of Kiersten Batzli—IPR-2017-01208.
Declaration of Kiersten Batzli—IPR-2017-01209.
Declaration of Kiersten Batzli—IPR-2017-01253.
Declaration of Pamela Stransburg IPR-2017-01025.
Declaration of Pamela Stransburg IPR-2017-01026.
Declaration of Pamela Stransburg IPR-2017-01027.
Declaration of Pamela Stransburg IPR-2017-01028.
Declaration of Pamela Stransburg IPR-2017-01029.
Declaration of Pamela Stransburg IPR-2017-01201.
Declaration of Pamela Stransburg IPR-2017-01202.
Declaration of Pamela Stransburg IPR-2017-01203.
Declaration of Pamela Stransburg IPR-2017-01204.
Declaration of Pamela Stransburg IPR-2017-01205.
Declaration of Pamela Stransburg IPR-2017-01207.
Declaration of Pamela Stransburg IPR-2017-01208.
Declaration of Pamela Stransburg IPR-2017-01209.
Declaration of Pamela Stransburg IPR-2017-01253.
Declaration of Susanne Leupold and Accompanying Exhibits regarding O. Jegaden, IPR-2017-01201.
Declaration of Susanne Leupold and Accompanying Exhibits regarding O. Jegaden, IPR-2017-01202.
Declaration of Susanne Leupold and Accompanying Exhibits regarding O. Jegaden, IPR-2017-01203.
Declaration of Susanne Leupold and Accompanying Exhibits regarding O. Jegaden, IPR-2017-01207.
Declaration of Susanne Leupold and Accompanying Exhibits regarding O. Jegaden, IPR-2017-01208.
Dens, J. et al., *First Experience with the Impella Recover® LP 2.5 Micro Axial Pump in Patients with Cardiogenic Shock or Undergoing High-Risk Revascularisation*, EuroIntervention, May 2006.
Diastolic Balloon Pumping (With Carbon Dioxide) in the Aorta—a Mechanical Assistance to the Failing Circulation by S. D. Moulopoulos (1962).
Dubois-Rande, J. et al., *Assessment of a Percutaneous Hemopump in a High Risk Coronary Angioplasty Patients*, ASAIO Journal (1994) pp. M486-M488.
E. E. Kunst, J.A. van Alste, T. Arts, and H. B. K. Boom, Integrated Unit for Programmable Control of the 21F Hemopump and Registration of Physiological Signals, Med. & Biol. Eng. & Comput. 694-95 (Nov. 1994).
Exhibit 1001 of Petition filed in Inter Partes Review Case No. IPR2017-02134.
Exhibit 1001 of Petition filed in Inter Partes Review Case No. IPR2017-02135.
Exhibit 1001 of Petition filed in Inter Partes Review Case No. IPR2017-02150.
Exhibit 1001 of Petition filed in Inter Partes Review Case No. IPR2017-02151.
Exhibit 1001 of Petition filed in Inter Partes Review Case No. 1PR2017-02152.
Exhibit 1001 of Petition filed in Inter Partes Review Case No. IPR2017-02153.
Exhibit 1002 of Petition filed in Inter Partes Review Case No. IPR2017-02134.
Exhibit 1002 of Petition filed in Inter Partes Review Case No. IPR2017-02135.
Exhibit 1002 of Petition filed in Inter Partes Review Case No. IPR2017-02150.
Exhibit 1002 of Petition filed in Inter Partes Review Case No. IPR2017-02151.
Exhibit 1002 of Petition filed in Inter Partes Review Case No. IPR2017-02152.
Exhibit 1002 of Petition filed in Inter Partes Review Case No. IPR2017-02153.
Exhibit 1003 of Petition filed in Inter Partes Review Case No. IPR2017-02134.
Exhibit 1003 of Petition filed in Inter Partes Review Case No. IPR2017-02135.
Exhibit 1003 of Petition filed in Inter Partes Review Case No. IPR2017-02150.
Exhibit 1003 of Petition filed in Inter Partes Review Case No. IPR2017-02151.
Exhibit 1003 of Petition filed in Inter Partes Review Case No. IPR2017-02152.
Exhibit 1003 of Petition filed in Inter Partes Review Case No. IPR2017-02153.
Exhibit 1004 of Petition filed in Inter Partes Review Case No. IPR2017-02134.
Exhibit 1004 of Petition filed in Inter Partes Review Case No. IPR2017-02135.
Exhibit 1004 of Petition filed in Inter Partes Review Case No. IPR2017-02150.
Exhibit 1004 of Petition filed in Inter Partes Review Case No. IPR2017-02151.
Exhibit 1004 of Petition filed in Inter Partes Review Case No. IPR2017-02152.
Exhibit 1004 of Petition filed in Inter Partes Review Case No. IPR2017-02153.
Exhibit 1005 of Petition filed in Inter Partes Review Case No. IPR2017-02134.
Exhibit 1005 of Petition filed in Inter Partes Review Case No. IPR2017-02135.
Exhibit 1005 of Petition filed in Inter Partes Review Case No. IPR2017-02150.
Exhibit 1005 of Petition filed in Inter Partes Review Case No. IPR2017-02151.
Exhibit 1005 of Petition filed in Inter Partes Review Case No. IPR2017-02152.
Exhibit 1005 of Petition filed in Inter Partes Review Case No. IPR2017-02153.
Exhibit 1006 of Petition filed in Inter Partes Review Case No. IPR2017-02134.
Exhibit 1006 of Petition filed in Inter Partes Review Case No. IPR2017-02135.
Exhibit 1006 of Petition filed in Inter Partes Review Case No. IPR2017-02150.
Exhibit 1006 of Petition filed in Inter Partes Review Case No. IPR2017-02151.
Exhibit 1006 of Petition filed in Inter Partes Review Case No. IPR2017-02152.
Exhibit 1006 of Petition filed in Inter Partes Review Case No. IPR2017-02153.
Exhibit 1007 of Petition filed in Inter Partes Review Case No. IPR2017-02134.
Exhibit 1007 of Petition filed in Inter Partes Review Case No. IPR2017-02135.
Exhibit 1007 of Petition filed in Inter Partes Review Case No. IPR2017-02150.
Exhibit 1007 of Petition filed in Inter Partes Review Case No. IPR2017-02151.

(56) References Cited

OTHER PUBLICATIONS

Exhibit 1007 of Petition filed in Inter Partes Review Case No. IPR2017-02152.
Exhibit 1007 of Petition filed in Inter Partes Review Case No. IPR2017-02153.
Exhibit 1008 of Petition filed in Inter Partes Review Case No. IPR2017-02134.
Exhibit 1008 of Petition filed in Inter Partes Review Case No. IPR2017-02135.
Exhibit 1008 of Petition filed in Inter Partes Review Case No. IPR2017-02150.
Exhibit 1008 of Petition filed in Inter Partes Review Case No. IPR2017-02151.
Exhibit 1008 of Petition filed in Inter Partes Review Case No. IPR2017-02152.
Exhibit 1008 of Petition filed in Inter Partes Review Case No. IPR2017-02153.
Exhibit 1009 of Petition filed in Inter Partes Review Case No. IPR2017-02134.
Exhibit 1009 of Petition filed in Inter Partes Review Case No. IPR2017-02135.
Exhibit 1009 of Petition filed in Inter Partes Review Case No. IPR2017-02150.
Exhibit 1009 of Petition filed in Inter Partes Review Case No. IPR2017-02151.
Exhibit 1009 of Petition filed in Inter Partes Review Case No. IPR2017-02152.
Exhibit 1009 of Petition filed in Inter Partes Review Case No. IPR2017-02153.
Exhibit 1010 of Petition filed in Inter Partes Review Case No. IPR2017-02134.
Exhibit 1010 of Petition filed in Inter Partes Review Case No. IPR2017-02135.
Exhibit 1010 of Petition filed in Inter Partes Review Case No. IPR2017-02150.
Exhibit 1010 of Petition filed in Inter Partes Review Case No. IPR2017-02151.
Exhibit 1010 of Petition filed in Inter Partes Review Case No. IPR2017-02152.
Exhibit 1010 of Petition filed in Inter Partes Review Case No. IPR2017-02153.
Exhibit 1011 of Petition filed in Inter Partes Review Case No. IPR2017-02134.
Exhibit 1011 of Petition filed in Inter Partes Review Case No. IPR2017-02135.
Exhibit 1011 of Petition filed in Inter Partes Review Case No. IPR2017-02150.
Exhibit 1011 of Petition filed in Inter Partes Review Case No. IPR2017-02151.
Exhibit 1011 of Petition filed in Inter Partes Review Case No. IPR2017-02152.
Exhibit 1011 of Petition filed in Inter Partes Review Case No. IPR2017-02153.
Exhibit 1012 of Petition filed in Inter Partes Review Case No. IPR2017-02134.
Exhibit 1012 of Petition filed in Inter Partes Review Case No. IPR2017-02135.
Exhibit 1012 of Petition filed in Inter Partes Review Case No. IPR2017-02150.
Exhibit 1012 of Petition filed in Inter Partes Review Case No. IPR2017-02151.
Exhibit 1012 of Petition filed in Inter Partes Review Case No. IPR2017-02152.
Exhibit 1012 of Petition filed in Inter Partes Review Case No. IPR2017-02153.
Exhibit 1013 of Petition filed in Inter Partes Review Case No. IPR2017-02134.
Exhibit 1013 of Petition filed in Inter Partes Review Case No. IPR2017-02135.
Exhibit 1013 of Petition filed in Inter Partes Review Case No. IPR2017-02150.
Exhibit 1013 of Petition filed in Inter Partes Review Case No. IPR2017-02151.
Exhibit 1013 of Petition filed in Inter Partes Review Case No. IPR2017-02152.
Exhibit 1013 of Petition filed in Inter Partes Review Case No. IPR2017-02153.
Exhibit 1014 of Petition filed in Inter Partes Review Case No. IPR2017-02134.
Exhibit 1014 of Petition filed in Inter Partes Review Case No. IPR2017-02135.
Exhibit 1014 of Petition filed in Inter Partes Review Case No. IPR2017-02152.
Exhibit 1014 of Petition filed in Inter Partes Review Case No. IPR2017-02153.
Exhibit 1015 of Petition filed in Inter Partes Review Case No. IPR2017-02135.
Exhibit 1018 of Petition filed in Inter Partes Review Case No. IPR2017-02150.
Exhibit 1018 of Petition filed in Inter Partes Review Case No. IPR2017-02151.
Exhibit 1018 of Petition filed in Inter Partes Review Case No. IPR2017-02152.
Exhibit 1019 of Petition filed in Inter Partes Review Case No. IPR2017-02135.
Exhibit 1019 of Petition filed in Inter Partes Review Case No. IPR2017-02150.
Exhibit 1019 of Petition filed in Inter Partes Review Case No. IPR2017-02151.
Exhibit 1019 of Petition filed in Inter Partes Review Case No. IPR2017-02152.
Exhibit 1019 of Petition filed in Inter Partes Review Case No. IPR2017-02153.
Exhibit 1020 of Petition filed in Inter Partes Review Case No. IPR2017-02134.
Exhibit 1020 of Petition filed in Inter Partes Review Case No. IPR2017-02135.
Exhibit 1020 of Petition filed in Inter Partes Review Case No. IPR2017-02150.
Exhibit 1020 of Petition filed in Inter Partes Review Case No. IPR2017-02151.
Exhibit 1020 of Petition filed in Inter Partes Review Case No. IPR2017-02152.
Exhibit 1020 of Petition filed in Inter Partes Review Case No. IPR2017-02153.
Exhibit 1021 of Petition filed in Inter Partes Review Case No. IPR2017-02134.
Exhibit 1021 of Petition filed in Inter Partes Review Case No. IPR2017-02135.
Exhibit 1021 of Petition filed in Inter Partes Review Case No. IPR2017-02150.
Exhibit 1021 of Petition filed in Inter Partes Review Case No. IPR2017-02151.
Exhibit 1021 of Petition filed in Inter Partes Review Case No. IPR2017-02152.
Exhibit 1021 of Petition filed in Inter Partes Review Case No. IPR2017-02153.
Exhibit 1022 of Petition filed in Inter Partes Review Case No. IPR2017-02135.
Exhibit 1022 of Petition filed in Inter Partes Review Case No. IPR2017-02150.
Exhibit 1022 of Petition filed in Inter Partes Review Case No. IPR2017-02151.
Exhibit 1022 of Petition filed in Inter Partes Review Case No. IPR2017-02152.
Exhibit 1022 of Petition filed in Inter Partes Review Case No. IPR2017-02153.
Exhibit 1023 of Petition filed in Inter Partes Review Case No. IPR2017-02134.
Exhibit 1023 of Petition filed in Inter Partes Review Case No. IPR2017-02135.

(56) References Cited

OTHER PUBLICATIONS

Exhibit 1023 of Petition filed in Inter Partes Review Case No. IPR2017-02150.
Exhibit 1023 of Petition filed in Inter Partes Review Case No. IPR2017-02151.
Exhibit 1023 of Petition filed in Inter Partes Review Case No. IPR2017-02152.
Exhibit 1023 of Petition filed in Inter Partes Review Case No. IPR2017-02153.
Exhibit 1024 of Petition filed in Inter Partes Review Case No. IPR2017-02134.
Exhibit 1024 of Petition filed in Inter Partes Review Case No. IPR2017-02135.
Exhibit 1024 of Petition filed in Inter Partes Review Case No. IPR2017-02150.
Exhibit 1024 of Petition filed in Inter Partes Review Case No. IPR2017-02151.
Exhibit 1024 of Petition filed in Inter Partes Review Case No. IPR2017-02152.
Exhibit 1024 of Petition filed in Inter Partes Review Case No. IPR2017-02153.
Exhibit 1025 of Petition filed in Inter Partes Review Case No. IPR2017-02134.
Exhibit 1025 of Petition filed in Inter Partes Review Case No. IPR2017-02135.
Exhibit 1025 of Petition filed in Inter Partes Review Case No. IPR2017-02150.
Exhibit 1025 of Petition filed in Inter Partes Review Case No. IPR2017-02151.
Exhibit 1025 of Petition filed in Inter Partes Review Case No. IPR2017-02152.
Exhibit 1025 of Petition filed in Inter Partes Review Case No. IPR2017-02153.
Exhibit 1026 of Petition filed in Inter Partes Review Case No. IPR2017-02134.
Exhibit 1026 of Petition filed in Inter Partes Review Case No. IPR2017-02135.
Exhibit 1026 of Petition filed in Inter Partes Review Case No. IPR2017-02150.
Exhibit 1026 of Petition filed in Inter Partes Review Case No. IPR2017-02151.
Exhibit 1026 of Petition filed in Inter Partes Review Case No. IPR2017-02152.
Exhibit 1026 of Petition filed in Inter Partes Review Case No. IPR2017-02153.
Exhibit 1027 of Petition filed in Inter Partes Review Case No. IPR2017-02135.
Exhibit 1027 of Petition filed in Inter Partes Review Case No. IPR2017-02150.
Exhibit 1027 of Petition filed in Inter Partes Review Case No. IPR2017-02151.
Exhibit 1027 of Petition filed in Inter Partes Review Case No. IPR2017-02152.
Exhibit 1027 of Petition filed in Inter Partes Review Case No. IPR2017-02153.
Exhibit 1028 of Petition filed in Inter Partes Review Case No. IPR2017-02134.
Exhibit 1028 of Petition filed in Inter Partes Review Case No. IPR2017-02135.
Exhibit 1028 of Petition filed in Inter Partes Review Case No. IPR2017-02150.
Exhibit 1028 of Petition filed in Inter Partes Review Case No. IPR2017-02151.
Exhibit 1028 of Petition filed in Inter Partes Review Case No. IPR2017-02152.
Exhibit 1028 of Petition filed in Inter Partes Review Case No. IPR2017-02153.
Exhibit 1029 of Petition filed in Inter Partes Review Case No. IPR2017-02134.
Exhibit 1029 of Petition filed in Inter Partes Review Case No. IPR2017-02135.
Exhibit 1029 of Petition filed in Inter Partes Review Case No. IPR2017-02150.
Exhibit 1029 of Petition filed in Inter Partes Review Case No. IPR2017-02151.
Exhibit 1029 of Petition filed in Inter Partes Review Case No. IPR2017-02152.
Exhibit 1029 of Petition filed in Inter Partes Review Case No. IPR2017-02153.
Exhibit 1030 of Petition filed in Inter Partes Review Case No. IPR2017-02135.
Exhibit 1030 of Petition filed in Inter Partes Review Case No. IPR2017-02150.
Exhibit 1030 of Petition filed in Inter Partes Review Case No. IPR2017-02151.
Exhibit 1030 of Petition filed in Inter Partes Review Case No. IPR2017-02153.
Exhibit 1031 of Petition filed in Inter Partes Review Case No. IPR2017-02135.
Exhibit 1031 of Petition filed in Inter Partes Review Case No. IPR2017-02152.
Exhibit 1032 of Petition filed in Inter Partes Review Case No. IPR2017-02135.
Exhibit 1032 of Petition filed in Inter Partes Review Case No. IPR2017-02150.
Exhibit 1032 of Petition filed in Inter Partes Review Case No. IPR2017-02151.
Exhibit 1032 of Petition filed in Inter Partes Review Case No. IPR2017-02152.
Exhibit 1032 of Petition filed in Inter Partes Review Case No. IPR2017-02153.
Exhibit 1033 of Petition filed in Inter Partes Review Case No. IPR2017-02134.
Exhibit 1033 of Petition filed in Inter Partes Review Case No. IPR2017-02135.
Exhibit 1033 of Petition filed in Inter Partes Review Case No. IPR2017-02150.
Exhibit 1033 of Petition filed in Inter Partes Review Case No. IPR2017-02151.
Exhibit 1033 of Petition filed in Inter Partes Review Case No. IPR2017-02152.
Exhibit 1033 of Petition filed in Inter Partes Review Case No. IPR2017-02153.
Exhibit 1034 of Petition filed in Inter Partes Review Case No. IPR2017-02151.
Exhibit 1034 of Petition filed in Inter Partes Review Case No. IPR2017-02152.
Exhibit 1034 of Petition filed in Inter Partes Review Case No. IPR2017-02153.
Exhibit 1035 of Petition filed in Inter Partes Review Case No. IPR2017-02150.
Exhibit 1035 of Petition filed in Inter Partes Review Case No. IPR2017-02151.
Exhibit 1035 of Petition filed in Inter Partes Review Case No. IPR2017-02152.
Exhibit 1035 of Petition filed in Inter Partes Review Case No. IPR2017-02153.
Exhibit 1036 of Petition filed in Inter Partes Review Case No. IPR2017-02135.
Exhibit 1036 of Petition filed in Inter Partes Review Case No. IPR2017-02150.
Exhibit 1036 of Petition filed in Inter Partes Review Case No. IPR2017-02151.
Exhibit 1036 of Petition filed in Inter Partes Review Case No. IPR2017-02152.
Exhibit 1036 of Petition filed in Inter Partes Review Case No. IPR2017-02153.
Exhibit 1037 of Petition filed in Inter Partes Review Case No. IPR2017-02134.
Exhibit 1037 of Petition filed in Inter Partes Review Case No. IPR2017-02135.

(56) References Cited

OTHER PUBLICATIONS

Exhibit 1037 of Petition filed in Inter Partes Review Case No. IPR2017-02150.
Exhibit 1037 of Petition filed in Inter Partes Review Case No. IPR2017-02151.
Exhibit 1037 of Petition filed in Inter Partes Review Case No. IPR2017-02152.
Exhibit 1037 of Petition filed in Inter Partes Review Case No. IPR2017-02153.
Exhibit 1038 of Petition filed in Inter Partes Review Case No. IPR2017-02134.
Exhibit 1038 of Petition filed in Inter Partes Review Case No. IPR2017-02135.
Exhibit 1038 of Petition filed in Inter Partes Review Case No. IPR2017-02150.
Exhibit 1038 of Petition filed in Inter Partes Review Case No. IPR2017-02151.
Exhibit 1038 of Petition filed in Inter Partes Review Case No. IPR2017-02152.
Exhibit 1038 of Petition filed in Inter Partes Review Case No. IPR2017-02153.
Exhibit 1039 of Petition filed in Inter Partes Review Case No. IPR2017-02134.
Exhibit 1039 of Petition filed in Inter Partes Review Case No. IPR2017-02135.
Exhibit 1039 of Petition filed in Inter Partes Review Case No. IPR2017-02150.
Exhibit 1039 of Petition filed in Inter Partes Review Case No. IPR2017-02151.
Exhibit 1039 of Petition filed in Inter Partes Review Case No. IPR2017-02152.
Exhibit 1039 of Petition filed in Inter Partes Review Case No. IPR2017-02153.
Exhibit 1040 of Petition filed in Inter Partes Review Case No. IPR2017-02135.
Exhibit 1040 of Petition filed in Inter Partes Review Case No. IPR2017-02150.
Exhibit 1040 of Petition filed in Inter Partes Review Case No. IPR2017-02151.
Exhibit 1040 of Petition filed in Inter Partes Review Case No. IPR2017-02152.
Exhibit 1040 of Petition filed in Inter Partes Review Case No. IPR2017-02153.
Exhibit 1041 of Petition filed in Inter Partes Review Case No. IPR2017-02134.
Exhibit 1041 of Petition filed in Inter Partes Review Case No. IPR2017-02135.
Exhibit 1041 of Petition filed in Inter Partes Review Case No. IPR2017-02150.
Exhibit 1041 of Petition filed in Inter Partes Review Case No. IPR2017-02151.
Exhibit 1041 of Petition filed in Inter Partes Review Case No. IPR2017-02152.
Exhibit 1041 of Petition filed in Inter Partes Review Case No. IPR2017-02153.
Exhibit 1042 of Petition filed in Inter Partes Review Case No. IPR2017-02135.
Exhibit 1042 of Petition filed in Inter Partes Review Case No. IPR2017-02150.
Exhibit 1042 of Petition filed in Inter Partes Review Case No. IPR2017-02151.
Exhibit 1042 of Petition filed in Inter Partes Review Case No. IPR2017-02152.
Exhibit 1042 of Petition filed in Inter Partes Review Case No. IPR2017-02153.
Exhibit 1043 of Petition filed in Inter Partes Review Case No. IPR2017-02150.
Exhibit 1043 of Petition filed in Inter Partes Review Case No. IPR2017-02151.
Exhibit 1043 of Petition filed in Inter Partes Review Case No. IPR2017-02152.
Exhibit 1043 of Petition filed in Inter Partes Review Case No. IPR2017-02153.
Exhibit 1044 of Petition filed in Inter Partes Review Case No. IPR2017-02135.
Exhibit 1044 of Petition filed in Inter Partes Review Case No. IPR2017-02151.
Exhibit 1044 of Petition filed in Inter Partes Review Case No. IPR2017-02152.
Exhibit 1044 of Petition filed in Inter Partes Review Case No. IPR2017-02153.
Exhibit 1045 of Petition filed in Inter Partes Review Case No. IPR2017-02134.
Exhibit 1045 of Petition filed in Inter Partes Review Case No. IPR2017-02135.
Exhibit 1045 of Petition filed in Inter Partes Review Case No. IPR2017-02150.
Exhibit 1045 of Petition filed in Inter Partes Review Case No. IPR2017-02151.
Exhibit 1045 of Petition filed in Inter Partes Review Case No. IPR2017-02152.
Exhibit 1045 of Petition filed in Inter Partes Review Case No. IPR2017-02153.
Exhibit 1046 of Petition filed in Inter Partes Review Case No. IPR2017-02134.
Exhibit 1046 of Petition filed in Inter Partes Review Case No. IPR2017-02135.
Exhibit 1046 of Petition filed in Inter Partes Review Case No. IPR2017-02150.
Exhibit 1046 of Petition filed in Inter Partes Review Case No. IPR2017-02151.
Exhibit 1046 of Petition filed in Inter Partes Review Case No. IPR2017-02152.
Exhibit 1046 of Petition filed in Inter Partes Review Case No. IPR2017-02153.
Exhibit 1047 of Petition filed in Inter Partes Review Case No. IPR2017-02150.
Exhibit 1047 of Petition filed in Inter Partes Review Case No. IPR2017-02151.
Exhibit 1047 of Petition filed in Inter Partes Review Case No. IPR2017-02152.
Exhibit 1047 of Petition filed in Inter Partes Review Case No. IPR2017-02153.
Exhibit 1048 of Petition filed in Inter Partes Review Case No. IPR2017-02150.
Exhibit 1048 of Petition filed in Inter Partes Review Case No. IPR2017-02151.
Exhibit 1048 of Petition filed in Inter Partes Review Case No. IPR2017-02152.
Exhibit 1048 of Petition filed in Inter Partes Review Case No. IPR2017-02153.
Exhibit 1049 of Petition filed in Inter Partes Review Case No. IPR2017-02134.
Exhibit 1049 of Petition filed in Inter Partes Review Case No. IPR2017-02150.
Exhibit 1049 of Petition filed in Inter Partes Review Case No. IPR2017-02151.
Exhibit 1049 of Petition filed in Inter Partes Review Case No. IPR2017-02152.
Exhibit 1049 of Petition filed in Inter Partes Review Case No. IPR2017-02153.
Exhibit 1050 of Petition filed in Inter Partes Review Case No. IPR2017-02134.
Exhibit 1050 of Petition filed in Inter Partes Review Case No. IPR2017-02150.
Exhibit 1050 of Petition filed in Inter Partes Review Case No. IPR2017-02151.
Exhibit 1050 of Petition filed in Inter Partes Review Case No. IPR2017-02152.
Exhibit 1050 of Petition filed in Inter Partes Review Case No. IPR2017-02153.

(56) References Cited

OTHER PUBLICATIONS

Exhibit 1051 of Petition filed in Inter Partes Review Case No. IPR2017-02134.
Exhibit 1051 of Petition filed in Inter Partes Review Case No. IPR2017-02150.
Exhibit 1051 of Petition filed in Inter Partes Review Case No. IPR2017-02151.
Exhibit 1051 of Petition filed in Inter Partes Review Case No. IPR2017-02152.
Exhibit 1051 of Petition filed in Inter Partes Review Case No. IPR2017-02153.
Exhibit 1052 of Petition filed in Inter Partes Review Case No. IPR2017-02134.
Exhibit 1052 of Petition filed in Inter Partes Review Case No. IPR2017-02150.
Exhibit 1052 of Petition filed in Inter Partes Review Case No. IPR2017-02151.
Exhibit 1052 of Petition filed in Inter Partes Review Case No. IPR2017-02152.
Exhibit 1052 of Petition filed in Inter Partes Review Case No. IPR2017-02153.
Exhibit 1053 of Petition filed in Inter Partes Review Case No. IPR2017-02134.
Exhibit 1053 of Petition filed in Inter Partes Review Case No. IPR2017-02150.
Exhibit 1053 of Petition filed in Inter Partes Review Case No. IPR2017-02151.
Exhibit 1053 of Petition filed in Inter Partes Review Case No. IPR2017-02152.
Exhibit 1053 of Petition filed in Inter Partes Review Case No. IPR2017-02153.
Exhibit 1054 of Petition filed in Inter Partes Review Case No. IPR2017-02134.
Exhibit 1054 of Petition filed in Inter Partes Review Case No. IPR2017-02150.
Exhibit 1054 of Petition filed in Inter Partes Review Case No. IPR2017-02151.
Exhibit 1054 of Petition filed in Inter Partes Review Case No. IPR2017-02152.
Exhibit 1054 of Petition filed in Inter Partes Review Case No. IPR2017-02153.
Exhibit 1055 of Petition filed in Inter Partes Review Case No. IPR2017-02150.
Exhibit 1055 of Petition filed in Inter Partes Review Case No. IPR2017-02151.
Exhibit 1055 of Petition filed in Inter Partes Review Case No. IPR2017-02153.
Exhibit 1056 of Petition filed in Inter Partes Review Case No. IPR2017-02134.
Exhibit 1056 of Petition filed in Inter Partes Review Case No. IPR2017-02135.
Exhibit 1056 of Petition filed in Inter Partes Review Case No. IPR2017-02150.
Exhibit 1056 of Petition filed in Inter Partes Review Case No. IPR2017-02151.
Exhibit 1057 of Petition filed in Inter Partes Review Case No. IPR2017-02135.
Exhibit 1057 of Petition filed in Inter Partes Review Case No. IPR2017-02150.
Exhibit 1058 of Petition filed in Inter Partes Review Case No. IPR2017-02135.
Exhibit 1059 of Petition filed in Inter Partes Review Case No. IPR2017-02134.
Exhibit 1059 of Petition filed in Inter Partes Review Case No. IPR2017-02135.
Exhibit 1060 of Petition filed in Inter Partes Review Case No. IPR2017-02134.
Exhibit 1060 of Petition filed in Inter Partes Review Case No. IPR2017-02135.
Exhibit 1061 of Petition filed in Inter Partes Review Case No. IPR2017-02134.
Exhibit 1061 of Petition filed in Inter Partes Review Case No. IPR2017-02135.
Exhibit 1062 of Petition filed in Inter Partes Review Case No. IPR2017-02134.
Exhibit 1062 of Petition filed in Inter Partes Review Case No. IPR2017-02135.
Exhibit 1063 of Petition filed in Inter Partes Review Case No. IPR2017-02135.
Exhibit 1064 of Petition filed in Inter Partes Review Case No. IPR2017-02135.
Exhibit 1065 of Petition filed in Inter Partes Review Case No. IPR2017-02135.
Exhibit 1066 of Petition filed in Inter Partes Review Case No. IPR2017-02135.
Exhibit 2001 of Patent Owner's Preliminary Response filed in Inter Partes Review Case No. IPR2017-01025.
Exhibit 2001 of Patent Owner's Preliminary Response filed in Inter Partes Review Case No. IPR2017-01026.
Exhibit 2001 of Patent Owner's Preliminary Response filed in Inter Partes Review Case No. IPR2017-01027.
Exhibit 2001 of Patent Owner's Preliminary Response filed in Inter Partes Review Case No. IPR2017-01028.
Exhibit 2001 of Patent Owner's Preliminary Response filed in Inter Partes Review Case No. IPR2017-01029.
Exhibit 2001 of Patent Owner's Preliminary Response filed in Inter Partes Review Case No. IPR2017-01201.
Exhibit 2001 of Patent Owner's Preliminary Response filed in Inter Partes Review Case No. IPR2017-01202.
Exhibit 2001 of Patent Owner's Preliminary Response filed in Inter Partes Review Case No. IPR2017-01203.
Exhibit 2001 of Patent Owner's Preliminary Response filed in Inter Partes Review Case No. IPR2017-01204.
Exhibit 2001 of Patent Owner's Preliminary Response filed in Inter Partes Review Case No. IPR2017-01205.
Exhibit 2001 of Patent Owner's Preliminary Response filed in Inter Partes Review Case No. IPR2017-01207.
Exhibit 2001 of Patent Owner's Preliminary Response filed in Inter Partes Review Case No. IPR2017-01208.
Exhibit 2001 of Patent Owner's Preliminary Response filed in Inter Partes Review Case No. IPR2017-01209.
Exhibit 2001 of Patent Owner's Preliminary Response filed in Inter Partes Review Case No. IPR2017-01253.
Exhibit 2001 of Petition filed in Inter Partes Review Case No. IPR2017-02134.
Exhibit 2001 of Petition filed in Inter Partes Review Case No. IPR2017-02135.
Exhibit 2001 of Petition filed in Inter Partes Review Case No. IPR2017-02150.
Exhibit 2001 of Petition filed in Inter Partes Review Case No. IPR2017-02151.
Exhibit 2001 of Petition filed in Inter Partes Review Case No. IPR2017-02152.
Exhibit 2001 of Petition filed in Inter Partes Review Case No. 1PR2017-02153.
Exhibit 2002 of Patent Owner's Preliminary Response filed in Inter Partes Review Case No. IPR2017-01025.
Exhibit 2002 of Patent Owner's Preliminary Response filed in Inter Partes Review Case No. IPR2017-01026.
Exhibit 2002 of Patent Owner's Preliminary Response filed in Inter Partes Review Case No. IPR2017-01027.
Exhibit 2002 of Patent Owner's Preliminary Response filed in Inter Partes Review Case No. IPR2017-01028.
Exhibit 2002 of Patent Owner's Preliminary Response filed in Inter Partes Review Case No. IPR2017-01029.
Exhibit 2002 of Patent Owner's Preliminary Response filed in Inter Partes Review Case No. IPR2017-01201.
Exhibit 2002 of Patent Owner's Preliminary Response filed in Inter Partes Review Case No. IPR2017-01202.
Exhibit 2002 of Patent Owner's Preliminary Response filed in Inter Partes Review Case No. IPR2017-01203.

(56) References Cited

OTHER PUBLICATIONS

Exhibit 2002 of Patent Owner's Preliminary Response filed in Inter Partes Review Case No. IPR2017-01204.
Exhibit 2002 of Patent Owner's Preliminary Response filed in Inter Partes Review Case No. IPR2017-01205.
Exhibit 2002 of Patent Owner's Preliminary Response filed in Inter Partes Review Case No. IPR2017-01207.
Exhibit 2002 of Patent Owner's Preliminary Response filed in Inter Partes Review Case No. IPR2017-01208.
Exhibit 2002 of Patent Owner's Preliminary Response filed in Inter Partes Review Case No. IPR2017-01209.
Exhibit 2002 of Patent Owner's Preliminary Response filed in Inter Partes Review Case No. IPR2017-01253.
Exhibit 2002 of Petition filed in Inter Partes Review Case No. IPR2017-02134.
Exhibit 2002 of Petition filed in Inter Partes Review Case No. IPR2017-02135.
Exhibit 2002 of Petition filed in Inter Partes Review Case No. IPR2017-02150.
Exhibit 2002 of Petition filed in Inter Partes Review Case No. IPR2017-02151.
Exhibit 2002 of Petition filed in Inter Partes Review Case No. IPR2017-02152.
Exhibit 2002 of Petition filed in Inter Partes Review Case No. IPR2017-02153.
Exhibit 2003 of Patent Owner's Preliminary Response filed in Inter Partes Review Case No. IPR2017-01025.
Exhibit 2003 of Patent Owner's Preliminary Response filed in Inter Partes Review Case No. IPR2017-01026.
Exhibit 2003 of Patent Owner's Preliminary Response filed in Inter Partes Review Case No. IPR2017-01027.
Exhibit 2003 of Patent Owner's Preliminary Response filed in Inter Partes Review Case No. IPR2017-01028.
Exhibit 2003 of Patent Owner's Preliminary Response filed in Inter Partes Review Case No. IPR2017-01029.
Exhibit 2003 of Petition filed in Inter Partes Review Case No. IPR2017-02134.
Exhibit 2003 of Petition filed in Inter Partes Review Case No. IPR2017-02135.
Exhibit 2003 of Petition filed in Inter Partes Review Case No. IPR2017-02150.
Exhibit 2003 of Petition filed in Inter Partes Review Case No. IPR2017-02151.
Exhibit 2003 of Petition filed in Inter Partes Review Case No. IPR2017-02152.
Exhibit 2003 of Petition filed in Inter Partes Review Case No. IPR2017-02153.
Exhibit 2004 of Patent Owner's Preliminary Response filed in Inter Partes Review Case No. IPR2017-01025.
Exhibit 2004 of Patent Owner's Preliminary Response filed in Inter Partes Review Case No. IPR2017-01026.
Exhibit 2004 of Patent Owner's Preliminary Response filed in Inter Partes Review Case No. IPR2017-01027.
Exhibit 2004 of Patent Owner's Preliminary Response filed in Inter Partes Review Case No. IPR2017-01028.
Exhibit 2004 of Patent Owner's Preliminary Response filed in Inter Partes Review Case No. IPR2017-01029.
Exhibit 2004 of Patent Owner's Preliminary Response filed in Inter Partes Review Case No. IPR2017-01201.
Exhibit 2004 of Patent Owner's Preliminary Response filed in Inter Partes Review Case No. IPR2017-01202.
Exhibit 2004 of Patent Owner's Preliminary Response filed in Inter Partes Review Case No. IPR2017-01203.
Exhibit 2004 of Patent Owner's Preliminary Response filed in Inter Partes Review Case No. IPR2017-01204.
Exhibit 2004 of Patent Owner's Preliminary Response filed in Inter Partes Review Case No. IPR2017-01205.
Exhibit 2004 of Patent Owner's Preliminary Response filed in Inter Partes Review Case No. IPR2017-01207.
Exhibit 2004 of Patent Owner's Preliminary Response filed in Inter Partes Review Case No. IPR2017-01208.
Exhibit 2004 of Patent Owner's Preliminary Response filed in Inter Partes Review Case No. IPR2017-01209.
Exhibit 2004 of Patent Owner's Preliminary Response filed in Inter Partes Review Case No. IPR2017-01253.
Exhibit 2004 of Petition filed in Inter Partes Review Case No. IPR2017-02134.
Exhibit 2004 of Petition filed in Inter Partes Review Case No. IPR2017-02135.
Exhibit 2004 of Petition filed in Inter Partes Review Case No. IPR2017-02150.
Exhibit 2004 of Petition filed in Inter Partes Review Case No. IPR2017-02151.
Exhibit 2004 of Petition filed in Inter Partes Review Case No. IPR2017-02152.
Exhibit 2004 of Petition filed in Inter Partes Review Case No. IPR2017-02153.
Exhibit 2005 of Patent Owner's Preliminary Response filed in Inter Partes Review Case No. IPR2017-01025.
Exhibit 2005 of Patent Owner's Preliminary Response filed in Inter Partes Review Case No. IPR2017-01026.
Exhibit 2005 of Patent Owner's Preliminary Response filed in Inter Partes Review Case No. IPR2017-01027.
Exhibit 2005 of Patent Owner's Preliminary Response filed in Inter Partes Review Case No. IPR2017-01028.
Exhibit 2005 of Patent Owner's Preliminary Response filed in Inter Partes Review Case No. IPR2017-01029.
Exhibit 2005 of Petition filed in Inter Partes Review Case No. IPR2017-02134.
Exhibit 2005 of Petition filed in Inter Partes Review Case No. IPR2017-02135.
Exhibit 2005 of Petition filed in Inter Partes Review Case No. IPR2017-02150.
Exhibit 2005 of Petition filed in Inter Partes Review Case No. IPR2017-02151.
Exhibit 2005 of Petition filed in Inter Partes Review Case No. IPR2017-02152.
Exhibit 2005 of Petition filed in Inter Partes Review Case No. IPR2017-02153.
Exhibit 2006 of Patent Owner's Preliminary Response filed in Inter Partes Review Case No. IPR2017-01025.
Exhibit 2006 of Patent Owner's Preliminary Response filed in Inter Partes Review Case No. IPR2017-01026.
Exhibit 2006 of Patent Owner's Preliminary Response filed in Inter Partes Review Case No. IPR2017-01027.
Exhibit 2006 of Patent Owner's Preliminary Response filed in Inter Partes Review Case No. IPR2017-01028.
Exhibit 2006 of Patent Owner's Preliminary Response filed in Inter Partes Review Case No. IPR2017-01029.
Exhibit 2006 of Patent Owner's Preliminary Response filed in Inter Partes Review Case No. IPR2017-01201.
Exhibit 2006 of Patent Owner's Preliminary Response filed in Inter Partes Review Case No. IPR2017-01202.
Exhibit 2006 of Patent Owner's Preliminary Response filed in Inter Partes Review Case No. IPR2017-01203.
Exhibit 2006 of Patent Owner's Preliminary Response filed in Inter Partes Review Case No. IPR2017-01204.
Exhibit 2006 of Patent Owner's Preliminary Response filed in Inter Partes Review Case No. IPR2017-01205.
Exhibit 2006 of Patent Owner's Preliminary Response filed in Inter Partes Review Case No. IPR2017-01207.
Exhibit 2006 of Patent Owner's Preliminary Response filed in Inter Partes Review Case No. IPR2017-01208.
Exhibit 2006 of Patent Owner's Preliminary Response filed in Inter Partes Review Case No. IPR2017-01209.
Exhibit 2006 of Patent Owner's Preliminary Response filed in Inter Partes Review Case No. IPR2017-01253.
Exhibit 2006 of Petition filed in Inter Partes Review Case No. IPR2017-02134.
Exhibit 2006 of Petition filed in Inter Partes Review Case No. IPR2017-02135.

(56) References Cited

OTHER PUBLICATIONS

Exhibit 2006 of Petition filed in Inter Partes Review Case No. IPR2017-02151.
Exhibit 2006 of Petition filed in Inter Partes Review Case No. IPR2017-02153.
Exhibit 2007 of Patent Owner's Preliminary Response filed in Inter Partes Review Case No. IPR2017-01025.
Exhibit 2007 of Patent Owner's Preliminary Response filed in Inter Partes Review Case No. IPR2017-01026.
Exhibit 2007 of Patent Owner's Preliminary Response filed in Inter Partes Review Case No. IPR2017-01027.
Exhibit 2007 of Patent Owner's Preliminary Response filed in Inter Partes Review Case No. IPR2017-01028.
Exhibit 2007 of Patent Owner's Preliminary Response filed in Inter Partes Review Case No. IPR2017-01029.
Exhibit 2007 of Patent Owner's Preliminary Response filed in Inter Partes Review Case No. IPR2017-01201.
Exhibit 2007 of Patent Owner's Preliminary Response filed in Inter Partes Review Case No. IPR2017-01202.
Exhibit 2007 of Patent Owner's Preliminary Response filed in Inter Partes Review Case No. IPR2017-01203.
Exhibit 2007 of Patent Owner's Preliminary Response filed in Inter Partes Review Case No. IPR2017-01204.
Exhibit 2007 of Patent Owner's Preliminary Response filed in Inter Partes Review Case No. IPR2017-01205.
Exhibit 2007 of Patent Owner's Preliminary Response filed in Inter Partes Review Case No. IPR2017-01207.
Exhibit 2007 of Patent Owner's Preliminary Response filed in Inter Partes Review Case No. IPR2017-01208.
Exhibit 2007 of Patent Owner's Preliminary Response filed in Inter Partes Review Case No. IPR2017-01209.
Exhibit 2007 of Petition filed in Inter Partes Review Case No. IPR2017-02134.
Exhibit 2007 of Petition filed in Inter Partes Review Case No. IPR2017-02135.
Exhibit 2007 of Petition filed in Inter Partes Review Case No. LPR2017-02151.
Exhibit 2007 of Petition filed in Inter Partes Review Case No. IPR2017-02153.
Exhibit 2008 of Patent Owner's Preliminary Response filed in Inter Partes Review Case No. IPR2017-01025.
Exhibit 2008 of Patent Owner's Preliminary Response filed in Inter Partes Review Case No. IPR2017-01026.
Exhibit 2008 of Patent Owner's Preliminary Response filed in Inter Partes Review Case No. IPR2017-01027.
Exhibit 2008 of Patent Owner's Preliminary Response filed in Inter Partes Review Case No. IPR2017-01028.
Exhibit 2008 of Patent Owner's Preliminary Response filed in Inter Partes Review Case No. IPR2017-01029.
Exhibit 2008 of Patent Owner's Preliminary Response filed in Inter Partes Review Case No. IPR2017-01201.
Exhibit 2008 of Patent Owner's Preliminary Response filed in Inter Partes Review Case No. IPR2017-01202.
Exhibit 2008 of Patent Owner's Preliminary Response filed in Inter Partes Review Case No. IPR2017-01203.
Exhibit 2008 of Patent Owner's Preliminary Response filed in Inter Partes Review Case No. IPR2017-01204.
Exhibit 2008 of Patent Owner's Preliminary Response filed in Inter Partes Review Case No. IPR2017-01205.
Exhibit 2008 of Patent Owner's Preliminary Response filed in Inter Partes Review Case No. IPR2017-01207.
Exhibit 2008 of Patent Owner's Preliminary Response filed in Inter Partes Review Case No. IPR2017-01208.
Exhibit 2008 of Patent Owner's Preliminary Response filed in Inter Partes Review Case No. IPR2017-01209.
Exhibit 2008 of Petition filed in Inter Partes Review Case No. IPR2017-02134.
Exhibit 2008 of Petition filed in Inter Partes Review Case No. IPR2017-02151.
Exhibit 2008 of Petition filed in Inter Partes Review Case No. IPR2017-02153.
Exhibit 2009 of Patent Owner's Preliminary Response filed in Inter Partes Review Case No. IPR2017-01025.
Exhibit 2009 of Patent Owner's Preliminary Response filed in Inter Partes Review Case No. IPR2017-01026.
Exhibit 2009 of Patent Owner's Preliminary Response filed in Inter Partes Review Case No. IPR2017-01027.
Exhibit 2009 of Patent Owner's Preliminary Response filed in Inter Partes Review Case No. IPR2017-01028.
Exhibit 2009 of Patent Owner's Preliminary Response filed in Inter Partes Review Case No. IPR2017-01029.
Exhibit 2009 of Patent Owner's Preliminary Response filed in Inter Partes Review Case No. IPR2017-01201.
Exhibit 2009 of Patent Owner's Preliminary Response filed in Inter Partes Review Case No. IPR2017-01202.
Exhibit 2009 of Patent Owner's Preliminary Response filed in Inter Partes Review Case No. IPR2017-01203.
Exhibit 2009 of Patent Owner's Preliminary Response filed in Inter Partes Review Case No. IPR2017-01204.
Exhibit 2009 of Patent Owner's Preliminary Response filed in Inter Partes Review Case No. IPR2017-01205.
Exhibit 2009 of Patent Owner's Preliminary Response filed in Inter Partes Review Case No. IPR2017-01207.
Exhibit 2009 of Patent Owner's Preliminary Response filed in Inter Partes Review Case No. IPR2017-01208.
Exhibit 2009 of Patent Owner's Preliminary Response filed in Inter Partes Review Case No. IPR2017-01209.
Exhibit 2009 of Petition filed in Inter Partes Review Case No. IPR2017-02134.
Exhibit 2009 of Petition filed in Inter Partes Review Case No. IPR2017-02135.
Exhibit 2009 of Petition filed in Inter Partes Review Case No. IPR2017-02150.
Exhibit 2009 of Petition filed in Inter Partes Review Case No. IPR2017-02151.
Exhibit 2009 of Petition filed in Inter Partes Review Case No. IPR2017-02152.
Exhibit 2009 of Petition filed in Inter Partes Review Case No. IPR2017-02153.
Exhibit 2010 of Patent Owner's Preliminary Response filed in Inter Partes Review Case No. IPR2017-01025.
Exhibit 2010 of Patent Owner's Preliminary Response filed in Inter Partes Review Case No. IPR2017-01026.
Exhibit 2010 of Patent Owner's Preliminary Response filed in Inter Partes Review Case No. IPR2017-01027.
Exhibit 2010 of Patent Owner's Preliminary Response filed in Inter Partes Review Case No. IPR2017-01028.
Exhibit 2010 of Patent Owner's Preliminary Response filed in Inter Partes Review Case No. IPR2017-01029.
Exhibit 2010 of Patent Owner's Preliminary Response filed in Inter Partes Review Case No. IPR2017-01201.
Exhibit 2010 of Patent Owner's Preliminary Response filed in Inter Partes Review Case No. IPR2017-01202.
Exhibit 2010 of Patent Owner's Preliminary Response filed in Inter Partes Review Case No. IPR2017-01203.
Exhibit 2010 of Patent Owner's Preliminary Response filed in Inter Partes Review Case No. IPR2017-01204.
Exhibit 2010 of Patent Owner's Preliminary Response filed in Inter Partes Review Case No. IPR2017-01205.
Exhibit 2010 of Patent Owner's Preliminary Response filed in Inter Partes Review Case No. IPR2017-01207.
Exhibit 2010 of Patent Owner's Preliminary Response filed in Inter Partes Review Case No. IPR2017-01208.
Exhibit 2010 of Patent Owner's Preliminary Response filed in Inter Partes Review Case No. IPR2017-01209.
Exhibit 2010 of Petition filed in Inter Partes Review Case No. 1PR2017-02134.
Exhibit 2010 of Petition filed in Inter Partes Review Case No. IPR2017-02150.
Exhibit 2010 of Petition filed in Inter Partes Review Case No. IPR2017-02151.

(56) References Cited

OTHER PUBLICATIONS

Exhibit 2010 of Petition filed in Inter Partes Review Case No. IPR2017-02152.
Exhibit 2010 of Petition filed in Inter Partes Review Case No. IPR2017-02153.
Exhibit 2011 of Patent Owner's Preliminary Response filed in Inter Partes Review Case No. IPR2017-01025.
Exhibit 2011 of Patent Owner's Preliminary Response filed in Inter Partes Review Case No. IPR2017-01026.
Exhibit 2011 of Patent Owner's Preliminary Response filed in Inter Partes Review Case No. IPR2017-01027.
Exhibit 2011 of Patent Owner's Preliminary Response filed in Inter Partes Review Case No. IPR2017-01028.
Exhibit 2011 of Patent Owner's Preliminary Response filed in Inter Partes Review Case No. IPR2017-01029.
Exhibit 2011 of Petition filed in Inter Partes Review Case No. IPR2017-02134.
Exhibit 2011 of Petition filed in Inter Partes Review Case No. IPR2017-02135.
Exhibit 2011 of Petition filed in Inter Partes Review Case No. IPR2017-02150.
Exhibit 2011 of Petition filed in Inter Partes Review Case No. IPR2017-02151.
Exhibit 2011 of Petition filed in Inter Partes Review Case No. IPR2017-02152.
Exhibit 2011 of Petition filed in Inter Partes Review Case No. IPR2017-02153.
Exhibit 2012 of Patent Owner's Preliminary Response filed in Inter Partes Review Case No. IPR2017-01025.
Exhibit 2012 of Patent Owner's Preliminary Response filed in Inter Partes Review Case No. IPR2017-01026.
Exhibit 2012 of Patent Owner's Preliminary Response filed in Inter Partes Review Case No. IPR2017-01027.
Exhibit 2012 of Patent Owner's Preliminary Response filed in Inter Partes Review Case No. IPR2017-01028.
Exhibit 2012 of Patent Owner's Preliminary Response filed in Inter Partes Review Case No. IPR2017-01029.
Exhibit 2012 of Petition filed in Inter Partes Review Case No. IPR2017-02134.
Exhibit 2012 of Petition filed in Inter Partes Review Case No. IPR2017-02135.
Exhibit 2012 of Petition filed in Inter Partes Review Case No. IPR2017-02150.
Exhibit 2012 of Petition filed in Inter Partes Review Case No. IPR2017-02151.
Exhibit 2012 of Petition filed in Inter Partes Review Case No. IPR2017-02152.
Exhibit 2012 of Petition filed in Inter Partes Review Case No. IPR2017-02153.
Exhibit 2013 of Patent Owner's Preliminary Response filed in Inter Partes Review Case No. IPR2017-01025.
Exhibit 2013 of Patent Owner's Preliminary Response filed in Inter Partes Review Case No. IPR2017-01026.
Exhibit 2013 of Patent Owner's Preliminary Response filed in Inter Partes Review Case No. IPR2017-01027.
Exhibit 2013 of Patent Owner's Preliminary Response filed in Inter Partes Review Case No. IPR2017-01028.
Exhibit 2013 of Patent Owner's Preliminary Response filed in Inter Partes Review Case No. IPR2017-01029.
Exhibit 2013 of Petition filed in Inter Partes Review Case No. IPR2017-02134.
Exhibit 2013 of Petition filed in Inter Partes Review Case No. IPR2017-02135.
Exhibit 2014 of Patent Owner's Preliminary Response filed in Inter Partes Review Case No. IPR2017-01025.
Exhibit 2014 of Patent Owner's Preliminary Response filed in Inter Partes Review Case No. IPR2017-01026.
Exhibit 2014 of Patent Owner's Preliminary Response filed in Inter Partes Review Case No. IPR2017-01027.
Exhibit 2014 of Patent Owner's Preliminary Response filed in Inter Partes Review Case No. IPR2017-01028.
Exhibit 2014 of Patent Owner's Preliminary Response filed in Inter Partes Review Case No. IPR2017-01029.
Exhibit 2014 of Patent Owner's Preliminary Response filed in Inter Partes Review Case No. IPR2017-01201.
Exhibit 2014 of Patent Owner's Preliminary Response filed in Inter Partes Review Case No. IPR2017-01202.
Exhibit 2014 of Patent Owner's Preliminary Response filed in Inter Partes Review Case No. IPR2017-01203.
Exhibit 2014 of Patent Owner's Preliminary Response filed in Inter Partes Review Case No. IPR2017-01204.
Exhibit 2014 of Patent Owner's Preliminary Response filed in Inter Partes Review Case No. IPR2017-01205.
Exhibit 2014 of Patent Owner's Preliminary Response filed in Inter Partes Review Case No. IPR2017-01207.
Exhibit 2014 of Patent Owner's Preliminary Response filed in Inter Partes Review Case No. IPR2017-01208.
Exhibit 2014 of Patent Owner's Preliminary Response filed in Inter Partes Review Case No. IPR2017-01209.
Exhibit 2014 of Petition filed in Inter Partes Review Case No. IPR2017-02134.
Exhibit 2014 of Petition filed in Inter Partes Review Case No. IPR2017-02135.
Exhibit 2015 of Patent Owner's Preliminary Response filed in Inter Partes Review Case No. IPR2017-01025.
Exhibit 2015 of Patent Owner's Preliminary Response filed in Inter Partes Review Case No. IPR2017-01026.
Exhibit 2015 of Patent Owner's Preliminary Response filed in Inter Partes Review Case No. IPR2017-01027.
Exhibit 2015 of Patent Owner's Preliminary Response filed in Inter Partes Review Case No. IPR2017-01028.
Exhibit 2015 of PatentrOwner's Preliminary Response filed in Inter Partes Review Case No. IPR2017-01029.
Exhibit 2015 of Patent Owner's Preliminary Response filed in Inter Partes Review Case No. IPR2017-01201.
Exhibit 2015 of Patent Owner's Preliminary Response filed in Inter Partes Review Case No. IPR2017-01202.
Exhibit 2015 of Patent Owner's Preliminary Response filed in Inter Partes Review Case No. IPR2017-01203.
Exhibit 2015 of Patent Owner's Preliminary Response filed in Inter Partes Review Case No. IPR2017-01204.
Exhibit 2015 of Patent Owner's Preliminary Response filed in Inter Partes Review Case No. IPR2017-01205.
Exhibit 2015 of Patent Owner's Preliminary Response filed in Inter Partes Review Case No. IPR2017-01207.
Exhibit 2015 of Patent Owner's Preliminary Response filed in Inter Partes Review Case No. IPR2017-01208.
Exhibit 2015 of Patent Owner's Preliminary Response filed in Inter Partes Review Case No. IPR2017-01209.
Exhibit 2015 of Petition filed in Inter Partes Review Case No. IPR2017-02134.
Exhibit 2015 of Petition filed in Inter Partes Review Case No. IPR2017-02135.
Exhibit 2016 of Patent Owner's Preliminary Response filed in Inter Partes Review Case No. IPR2017-01025.
Exhibit 2016 of Patent Owner's Preliminary Response filed in Inter Partes Review Case No. IPR2017-01026.
Exhibit 2016 of Patent Owner's Preliminary Response filed in Inter Partes Review Case No. IPR2017-01027.
Exhibit 2016 of Patent Owner's Preliminary Response filed in Inter Partes Review Case No. IPR2017-01028.
Exhibit 2016 of Patent Owner's Preliminary Response filed in Inter Partes Review Case No. IPR2017-01029.
Exhibit 2016 of Petition filed in Inter Partes Review Case No. IPR2017-02134.
Exhibit 2016 of Petition filed in Inter Partes Review Case No. IPR2017-02135.
Exhibit 2017 of Patent Owner's Preliminary Response filed in Inter Partes Review Case No. IPR2017-01025.
Exhibit 2017 of Patent Owner's Preliminary Response filed in Inter Partes Review Case No. IPR2017-01026.

(56) References Cited

OTHER PUBLICATIONS

Exhibit 2017 of Patent Owner's Preliminary Response filed in Inter Partes Review Case No. IPR2017-01027.
Exhibit 2017 of Patent Owner's Preliminary Response filed in Inter Partes Review Case No. IPR2017-01028.
Exhibit 2017 of Patent Owner's Preliminary Response filed in Inter Partes Review Case No. IPR2017-01029.
Exhibit 2017 of Patent Owner's Preliminary Response filed in Inter Partes Review Case No. IPR2017-01201.
Exhibit 2017 of Patent Owner's Preliminary Response filed in Inter Partes Review Case No. IPR2017-01202.
Exhibit 2017 of Patent Owner's Preliminary Response filed in Inter Partes Review Case No. IPR2017-01203.
Exhibit 2017 of Patent Owner's Preliminary Response filed in Inter Partes Review Case No. IPR2017-01204.
Exhibit 2017 of Patent Owner's Preliminary Response filed in Inter Partes Review Case No. IPR2017-01205.
Exhibit 2017 of Patent Owner's Preliminary Response filed in Inter Partes Review Case No. IPR2017-01207.
Exhibit 2017 of Patent Owner's Preliminary Response filed in Inter Partes Review Case No. IPR2017-01208.
Exhibit 2017 of Patent Owner's Preliminary Response filed in Inter Partes Review Case No. IPR2017-01209.
Exhibit 2017 of Petition filed in Inter Partes Review Case No. IPR2017-02134.
Exhibit 2018 of Patent Owner's Preliminary Response filed in Inter Partes Review Case No. IPR2017-01025.
Exhibit 2018 of Patent Owner's Preliminary Response filed in Inter Partes Review Case No. IPR2017-01026.
Exhibit 2018 of Patent Owner's Preliminary Response filed in Inter Partes Review Case No. IPR2017-01027.
Exhibit 2018 of Patent Owner's Preliminary Response filed in Inter Partes Review Case No. IPR2017-01028.
Exhibit 2018 of Patent Owner's Preliminary Response filed in Inter Partes Review Case No. IPR2017-01029.
Exhibit 2018 of Petition filed in Inter Partes Review Case No. IPR2017-02134.
Exhibit 2019 of Patent Owner's Preliminary Response filed in Inter Partes Review Case No. IPR2017-01025.
Exhibit 2019 of Patent Owner's Preliminary Response filed in Inter Partes Review Case No. IPR2017-01026.
Exhibit 2019 of Patent Owner's Preliminary Response filed in Inter Partes Review Case No. IPR2017-01027.
Exhibit 2019 of Patent Owner's Preliminary Response filed in Inter Partes Review Case No. IPR2017-01028.
Exhibit 2019 of Patent Owner's Preliminary Response filed in Inter Partes Review Case No. IPR2017-01029.
Exhibit 2019 of Petition filed in Inter Partes Review Case No. IPR2017-02134.
Exhibit 2020 of Patent Owner's Preliminary Response filed in Inter Partes Review Case No. IPR2017-01025.
Exhibit 2020 of Patent Owner's Preliminary Response filed in Inter Partes Review Case No. IPR2017-01026.
Exhibit 2020 of Patent Owner's Preliminary Response filed in Inter Partes Review Case No. IPR2017-01027.
Exhibit 2020 of Patent Owner's Preliminary Response filed in Inter Partes Review Case No. IPR2017-01028.
Exhibit 2020 of Patent Owner's Preliminary Response filed in Inter Partes Review Case No. IPR2017-01029.
Exhibit 2020 of Patent Owner's Preliminary Response filed in Inter Partes Review Case No. IPR2017-01201.
Exhibit 2020 of Patent Owner's Preliminary Response filed in Inter Partes Review Case No. IPR2017-01202.
Exhibit 2020 of Patent Owner's Preliminary Response filed in Inter Partes Review Case No. IPR2017-01203.
Exhibit 2020 of Patent Owner's Preliminary Response filed in Inter Partes Review Case No. IPR2017-01204.
Exhibit 2020 of Patent Owner's Preliminary Response filed in Inter Partes Review Case No. IPR2017-01205.
Exhibit 2020 of Patent Owner's Preliminary Response filed in Inter Partes Review Case No. IPR2017-01207.
Exhibit 2020 of Patent Owner's Preliminary Response filed in Inter Partes Review Case No. IPR2017-01208.
Exhibit 2020 of Patent Owner's Preliminary Response filed in Inter Partes Review Case No. IPR2017-01209.
Exhibit 2021 of Patent Owner's Preliminary Response filed in Inter Partes Review Case No. IPR2017-01025.
Exhibit 2021 of Patent Owner's Preliminary Response filed in Inter Partes Review Case No. IPR2017-01026.
Exhibit 2021 of Patent Owner's Preliminary Response filed in Inter Partes Review Case No. IPR2017-01027.
Exhibit 2021 of Patent Owner's Preliminary Response filed in Inter Partes Review Case No. IPR2017-01028.
Exhibit 2021 of Patent Owner's Preliminary Response filed in Inter Partes Review Case No. IPR2017-01029.
Exhibit 2021 of Patent Owner's Preliminary Response filed in Inter Partes Review Case No. IPR2017-01201.
Exhibit 2021 of Patent Owner's Preliminary Response filed in Inter Partes Review Case No. IPR2017-01202.
Exhibit 2021 of Patent Owner's Preliminary Response filed in Inter Partes Review Case No. IPR2017-01203.
Exhibit 2021 of Patent Owner's Preliminary Response filed in Inter Partes Review Case No. IPR2017-01204.
Exhibit 2021 of Patent Owner's Preliminary Response filed in Inter Partes Review Case No. IPR2017-01205.
Exhibit 2021 of Patent Owner's Preliminary Response filed in Inter Partes Review Case No. IPR2017-01207.
Exhibit 2021 of Patent Owner's Preliminary Response filed in Inter Partes Review Case No. IPR2017-01208.
Exhibit 2021 of Patent Owner's Preliminary Response filed in Inter Partes Review Case No. IPR2017-01209.
Exhibit 2022 of Patent Owner's Preliminary Response filed in Inter Partes Review Case No. IPR2017-01029.
Exhibit 2022 of Patent Owner's Preliminary Response filed in Inter Partes Review Case No. IPR2017-01204.
Exhibit 2022 of Patent Owner's Preliminary Response filed in Inter Partes Review Case No. IPR2017-01205.
Exhibit 2022 of Patent Owner's Preliminary Response filed in Inter Partes Review Case No. IPR2017-01207.
Exhibit 2023 of Patent Owner's Preliminary Response filed in Inter Partes Review Case No. IPR2017-01029.
Exhibit 2023 of Patent Owner's Preliminary Response filed in Inter Partes Review Case No. IPR2017-01204.
Exhibit 2023 of Patent Owner's Preliminary Response filed in Inter Partes Review Case No. IPR2017-01205.
Exhibit 2023 of Patent Owner's Preliminary Response filed in Inter Partes Review Case No. IPR2017-01207.
Exhibit 2024 of Patent Owner's Preliminary Response filed in Inter Partes Review Case No. IPR2017-01029.
Exhibit 2024 of Patent Owner's Preliminary Response filed in Inter Partes Review Case No. IPR2017-01204.
Exhibit 2024 of Patent Owner's Preliminary Response filed in Inter Partes Review Case No. IPR2017-01205.
Exhibit 2024 of Patent Owner's Preliminary Response filed in Inter Partes Review Case No. IPR2017-01207.
Exhibit 2024 of Patent Owner's Preliminary Response filed in Inter Partes Review Case No. IPR2017-01208.
Exhibit 2024 of Patent Owner's Preliminary Response filed in Inter Partes Review Case No. IPR2017-01209.
Exhibit 2025 of Patent Owner's Preliminary Response filed in Inter Partes Review Case No. IPR2017-01029.
Exhibit 2026 of Patent Owner's Preliminary Response filed in Inter Partes Review Case No. IPR2017-01029.
Exhibit 2027 of Patent Owner's Preliminary Response filed in Inter Partes Review Case No. IPR2017-01029.
Exhibit 2028 of Patent Owner's Preliminary Response filed in Inter Partes Review Case No. IPR2017-01029.
Exhibit 2029 of Patent Owner's Preliminary Response filed in Inter Partes Review Case No. IPR2017-01029.
Figulla, H. R., *Circulatory support devices in clinical cardiology*, Cardiology (1994).

(56) References Cited

OTHER PUBLICATIONS

U.S. Serial No. 09-280970 entitled "Pressure Sensing Cannula"—filed Mar. 30, 1999, USPTO.
U.S. Serial No. 09-280987 entitled "Cannula with Balloon Tip"—filed Mar. 30, 1999, USPTO.
U.S. Serial No. 09-280988 entitled "Steerable Cannula"—filed Mar. 30, 1999, USPTO.
U.S. Serial No. 10-566423 entitled "Intracardiac Pumping Device", USPTO, filed on Jan. 30, 2006.
Flameng, W., ed., Temporary Cardiac Assist with An Axial Pump System, Steinkopff Veriag Darmstadt, Springer-Verleg, New York, 1991.
Fraden, AIP Handbook of Modern Sensors: Physics, Design, and Applications, Amer. Inst. Physics (1993).
Frank K. White, Fluid Mechanics, 2nd edition, 1986.
Frazier, et al., Treatment of Cardiac Allograft Failure by Use of an Intraaortic Axial Flow Pump, J. Heart Transplanation 110 (1989).
Frazier, Mechanical Circulatory Assist Device Development at the Texas Heart Institute: A Personal Perspective, J. Thorac. & Cardiovascular Surg., 1738-44 (2014).
Frazier, O. H. et al., "First Human Use of the Hemopump, A Gather-Mounted Ventricular Assist Device," Ann Thorac Surg., Feb. 1990; 49(2): pp. 299-304.
Gacioch, G. M. et al., *Cardiogenic shock complicating acute myocardial infarction: the use of coronary angioplasty and the integration of the new support devices into patient management*, Journal of the American College of Cardiology (1992).
H. Reul et al., "Artificial Heart and Assist Device: New Development at the Helmholtz Institute", Chapter from *Heart Replacement* publ. springer (Japan), pp. 201-227, 1996.
*Hemopump Cardiac Assist Systems—Instructions for Use for the 14 French and 24 French Pump Assemblies*, Medtronic, Hemodynamics Division (1995).
Hemopump®: Temporary Cardiac Assist System Directions for Use, Nimbus Medical, Inc. (1988).
Impella Recover LP2.5: Percutaneous Cardiac Support System Instructions for Use, Abiomed, Inc. (2015).
Invalidity Contentions from *Abiomed Inc. v. Maquet Cardiovascular*, Case No. 1:16-cv-10914, filed in Dist. of Mass. on Sep. 8, 2017.
JOMED Reitan Catheter Pump Brochure, www.jomed.com/rcp (undated) (6 pages).
K.C. Butler et al., "The Hemopump—a New Cardiac Prosthesis Device", IEEE Trans Biomed Eng. 1990;37:193-196.
Kapoor, A., *Interventional Cardiology*, Springer-Verlag (1989).
Khashaba, RotablatorTM: Rotational Angioplasty System Basics of Operation.
Kirsten-Treptow, P., & Sieß, T. (2000), The intracardiac pump system—High-tech product and Technology Platform (original title in German "Das intrakardiale Pumpsystem—Hightech-Produkt und Technologie-Plattform"). Kardiotechnik, 9(3), pp. 77-80.
Konishi, H. et al., Controller for an Axial Flow Blood Pump, Artificial Organs 20(6): 618-20 (Jun. 1996).
Kozik, et al., Mechanical Circulatory Support, Organogenesis 7(1):50-63 (2001).
Lawrence K. Altman, A. Tiny Heart Pump Saves Its First Life, Researchers Report, N.Y. Times, May 5, 1988.
Letter from Ajey Atre to Michael R. Minogue dated Dec. 15, 2015.
Letter from Michael S. Connor to Richard T. McCaulley, Jr. dated May 3, 2016.
Letter from Richard T. McCaulley, Jr. dated May 19, 2016.
Letter from Richard T. McCaulley, Jr. to Ajey Atre dated Jan. 19, 2016.
Leupold Declaration—Jegaden IPR-201701204.
Leupold Declaration—Jegaden IPR-201701205.
Leupold Declaration—Jegaden IPR-201701209.
Leupold Declaration—Jegaden IPR-201701253.
Library of Congress, Catalog Record of "Supported Complex and High Risk Coronary Angioplasty" (1991).
Library of Congress, Catalog Record of Fluid Mechanics, 2nd edition, ed. Frank M. White (1986).
Library of Congress, Catalog Record of Konishi et al., "Controller for an axial flow blood pump," in Artificial Organs Journal, vol. 20, No. 6 (Jun. 1996) 618-612.
Library of Congress, Catalog Record of Moulopoulos et al., "Diastolic Balloon Pumping (With Carbon Dioxide) in the Aorta—a Mechanical Assistance to the Failing Circulation," in the American Heart Journal, vol. 63, No. 1 (1962) 669-675.
Library of Congress, Catalog Record of Textbook of Medical Physiology by Arthur C. Guyton and John E. Hall, 9th edition (1996).
Lincoff, A. M. et al., *Percutaneous Support Devices for High Risk or Complicated Coronary Angioplasty*, Journal of American College of Cardiology (1997).
Loisance, et al., Left-Ventricular Support by Intraventricular Blood Pump During High-Risk Coronary Angioplasty, The Lancet, 561 (1989).
Loisance, et al., Prophylactic Intraventricular Pumping in High-Risk Coronary Angioplasty, The Lancet, 438-40 (1990).
Lynn R. Williams, Reference Values for Total Blood Volumeand Cardiac Output in Humans, Oak Ridge Nat'l Lab. (Sep. 1994).
Magovern, et al., Nonpulsatile Circulatory Support: Techniques of Insertion, Ann. Thorac. Surg, 55(2): 66-72 (1993).
Maquet Cardiovascular LLC's Motion for Reconsideration and/or Clarification of Order on Claim Construction Regarding "Passing Purge Fluid" Terms, C.A. No. 1:16-CV-10914-FDS, Jury Demand, filed Sep. 27, 2018.
Maquet Cardiovascular LLC's Opening Markman Brief, C.A. No. 1:16-cv-10914-FDS, filed Dec. 15, 2017.
Maquet Cardiovascular LLC's Responsive Markman Brief, C.A. No. 1:16-cv-10914-FDS, filed Jan. 26, 2018.
Marseille, et al., Implantable Micropump System for Augmented Liver Perfusion, Int'l J. Artificial Organs 22(6): 458-60 (1998).
Maslen et al., "Feedback Control Applications in Artificial Hearts," in IEEE Control systems Magazine, vol. 18, No. 6 (1998).
Memorandum and Order on Claim Construction, Civil Action No. 16-10914-FDS, dated Sep. 7, 2018.
Memorandum of Law In Support of Maquet Cardiovascular LLC's Motion for Reconsideration and/or Clarification of Order on Claim Construction Regarding "Passing Purge Fluid" Terms, C.A. No. 1:16-cv-10914-FDS, Jury Demand, filed Sep. 27, 2018
Meyns, B. et al., *Mechanical Support with Microaxial Blood Pumps for Postcardiotomy Left Ventricular Failure: Can Outcome be Predicted?*, Elsevier Inc. (Aug. 2000).
Mihaylov, D. et al., *Development of a New Introduction Technique for the Pulsatile Catheter Pump*, Artif. Organs (1997).
Mizuno, K., *New Percutaneous Transluminal Coronary Angioscope*, Journal of American College of Cardiology (1989).
Nakatani, et al., In Vitro and In Vivo Assessment of an Intravenous Axial Flow Pump for Right Heart Assist, ASAIO J. M723-27 (1994).
Non-Final Office Action—dated Jun. 21, 2017—for U.S. Appl. No. 14/966,669, filed Dec. 11, 2015, which is related to this present application.
O. Jegaden, "Clinical results of Hemopump support in surgical cases," 1991.
Online encyclopedia article "Pyrolytic Carbon" accessed Feb. 19, 2009, http://en.wikipedia.org/wiki/Pyrolytic/carbon, 1 page.
Online encyclopedia article "Ventricular assist device, List of implantable VAD devices" accessed Jan. 12, 2010, http://en.wikipedia.org/wiki/Ventricular_assist_device, 11 pages.
Patent Owner Preliminary Response filed in Inter Partes Review Case No. IPR-2017-01025.
Patent Owner Preliminary Response filed in Inter Partes Review Case No. IPR-2017-01026.
Patent Owner Preliminary Response filed in Inter Partes Review Case No. IPR-2017-01027.
Patent Owner Preliminary Response filed in Inter Partes Review Case No. IPR-2017-01028.
Patent Owner Preliminary Response filed in Inter Partes Review Case No. IPR-2017-01029.
Patent Owner Preliminary Response filed in Inter Partes Review Case No. IPR2017-01201.

(56) References Cited

OTHER PUBLICATIONS

Patent Owner Preliminary Response filed in Inter Partes Review Case No. IPR2017-01202.
Patent Owner Preliminary Response filed in Inter Partes Review Case No. IPR2017-01203.
Patent Owner Preliminary Response filed in Inter Partes Review Case No. IPR2017-01204.
Patent Owner Preliminary Response filed in Inter Partes Review Case No. IPR2017-01205.
Patent Owner Preliminary Response filed in Inter Partes Review Case No. IPR2017-01207.
Patent Owner Preliminary Response filed in Inter Partes Review Case No. IPR2017-01208.
Patent Owner Preliminary Response filed in Inter Partes Review Case No. IPR2017-01209.
Patent Owner Preliminary Response filed in Inter Partes Review Case No. IPR2017-01253.
Patent Owner's Preliminary Response IPR2017-02134.
Patent Owner's Preliminary Response IPR2017-02135.
Patent Owner's Preliminary Response IPR2017-02150.
Patent Owner's Preliminary Response IPR2017-02151.
Patent Owner's Preliminary Response IPR2017-02152.
Patent Owner's Preliminary Response IPR2017-02153.
Petition for Inter Partes Review IPR2017-01205.
Petition IPR-2017-01025.
Petition IPR-2017-01026.
Petition IPR-2017-01027.
Petition IPR-2017-01028.
Petition IPR-2017-01029.
Petition IPR-2017-01201.
Petition IPR-2017-01202.
Petition IPR-2017-01203.
Petition IPR-2017-01204.
Petition IPR-2017-01207.
Petition IPR-2017-01208.
Petition IPR-2017-01209.
Petition IPR-2017-01253.
Petition, IPR2017-02134.
Petition, IPR2017-02135.
Petition, IPR2017-02150.
Petition, IPR2017-02151.
Petition, IPR2017-02152.
Petition, IPR2017-02153.
Petitioner's Request for Rehearing IPR2017-01026.
Petitioner's Request for Rehearing IPR2017-01027.
Petitioner's Request for Rehearing IPR2017-01025.
Petitioner's Request for Rehearing IPR2017-01028.
Petitioner's Request for Rehearing IPR2017-01029.
Pierce, W. S. et al., Portable artificial heart systems, ASAIO Journal 29.1: 757-59 (Apr. 1983).
Practical Angioplasty (David P. Faxon, M.D. ed., Raven Press 1993)—pp. 1 to 9.
Quaal, S., *Cardiac Mechanical Assistance Beyond Balloon Pumping*, Mosby (1993).
R. W. Smalling, The use of mechanical assist devices in the management of cardiogenic shock, Tecas Heart Institute Journal, vol. 18, No. 4, 1991, 275-81.
Reitan, Oyvind et al., "Hydrodynamic Properties of a New Percutaneous Intraaortic Axial Flow Pump," ASAIO Journal; Jan.-Jun. 2000; vol. 16; pp. 323-329.
Reul et al., "Rotary Blood Pumps in Circulatory Assist", Perfusion, May 1995; 10(3); pp. 153-168.
Schmitz, et al., An Expandable Percutaneous Catheter Pump for Left Ventricular Support: Proof of Concept, J. Am. Coll. Cardiology, 45 (11): 1856-61 (2005).
Schner, Design and Selection of Flexible Shaft (Aug. 15, 2016).
Scholz, et al., Clinical Experience with the Percutaneous Hemopump During High-Risk Coronary Angioplasty, Am. J. Cardiology, 82(9): 1107-10 (1998).
Scholz, et al., Mechanical Left Ventricular Unloading During High Risk Coronary Angioplsaty: First Use of a New Percutaneous Transvalvular Left Ventricular Assist Device, Catherization & Cardiovascular Disease 31: 61-69 (1994).
Seldinger, Catheter Replacement of the Needle in Percutaneous Arteriography, Acta Radiologica 39:368-76 (1953).
Siess, et al., Concept, Realization, and First In Vitro Testing of an Intraarterial Microaxial Blood Pump, Int'l J. Artificial Organs 19(7): 644-52 (1995).
Siess, et al., From a Lab Type to a Product: A Retrospective View on Impella's Assist Technology, Int'l J. Artificial Organs 25(5); 414-21 (2001).
Siess, et al., Hydraulic Refinement of an Intrarterial Microaxial Blood Pump, Int'l J. Artificial Organs 18(5): 273-85 (1995).
Stedman's Medical Dictionary, 27th edition, (1999).
Stolinski, et al., The Heart-Pump Interaction: Effects of a Microaxial Blood Pump, Int'l J. Artificial Organs 25(11): 1082-88 (2002).
Stronebridge, P. A., *Angioscopy: a New Light on Perpheral Vascular Disease*, European Journal of Vascular Surgery (1992).
Strong, Biophysical Measurements, Tektronix, Inc., 93-115 (1970).
Sweeney, The Hemopump in 1997: A Clinical, Political, and Marketing Evolution, Ann. Thorac. Surg. 68:761-63 (1999).
T. Siess et al., "Concept, Realization, and First In Vitro Testing of an Intraarterial Microaxial Blood Pump", Artificial Organs, vol. 19, Issue 7, pp. 644-652, Jul. 1995.
Siess, "System Analysis and Development of Intravascular Rotary Pumps to Support the Heart" (original title in German Systemanalyse and Entwicklung intravasaler Rotationspumpen zur Herzunterstutzung), Shaker, 1989 pages, 1999.
Taylor, K. M., *Cardiopulmonary Bypass, Principles and Management*, Williams & Wilkins (1986).
Textbook of Medical Physiology by Arthur C. Guyton and John E. Hall, 9th Edition (1996).
Throckmorton, et al., Numerical Design and Experimental Hydraulic Testing of an Axial Flow, ASAIO J., 754-61 (2007).
Throckmorton, et al., Numerical, Hydraulic, and Hemolytic Evalation of an Intravascular Axial Flow Blood Pump to Mechanically Support Fontan Patients, Ann. Biomed. Eng'g 39(1): 324-36 (2011.
U. Lonn et al., "Beating Heart Coronary Surgery Supported by an Axial Blood Flow Pump", The Annals of Thoracic Surgery, Jan. 1999, vol. 67, Issue 1, pp. 99-104.
Wampler et al., Clinical Experience with the Hemopump Left Ventricular Support Device, published in Supported Complex and High Risk Coronary Angioplasty, ch. 14, 231-49 (Springer 1st ed. 1991).
Wampler, et al., Circulatory Support of Cardiac Interventional Procedures with the HemopumpTM Cardiac Assist System, Cardiology 84:194-201 (1994).
Wampler, et al., The Sternotomy Hemopump: A Second Generation Intrarterial Ventricular Assist, ASAIO J., M218-23 (1993).
Wampler, Ricahrd K., "In Vivo Evaluation of a Peripheral Vascular Access Axial Flow Blood Pump," ASAIO Trans., Jul.-Sep. 1988; 34(3): pp. 450-454.
Webster, Medical Instrumentation, John Wiley & Sons (1973).
Wu et al., Ventricular Assist Devices: Current Status and Future Perspective, Frontiers in Biomedical Engineering, 197-231 (2003).
Wu, et al., Fluid Dynamic Characterization of Operating Conditions for Continuous Flow Blood Pumps, ASAIO J., 442-49 (1999).
ZB Med, Catalog Record of Temporary Cardiac Assist with an Axial Pump, ed. W. Flaming (1991).
Maq Rebuttal Validity Contentions Ex. A6 (Oct. 9, 2018).
Maq Rebuttal Validity Contentions Ex. A1.
Maq Rebuttal Validity Contentions Ex. A3.
Maq Rebuttal Validity Contentions Ex. A5.
Maq Rebuttal Validity Contentions Ex. A7.
Maq Rebuttal Validity Contentions Ex. A2.
Maq Rebuttal Validity Contentions Ex. A4.
Maq Rebuttal Validity Contentions.
Maq I Ex. A1—Invalidity by PCT Pub. No. WO 99/02204 ("Aboul-Hosn").
Maq I Ex. A2—Invalidity by "The Hemopump References".
Maq I Ex. A3—Invalidity based on "Jegaden".
Maq I Ex. A4—Invalidity by U.S. Pat. No. 6,248,091 ("Voelker").

(56) References Cited

OTHER PUBLICATIONS

Maq I Ex. A5—Invalidity by U.S. Pat. No. 5,921,913 ("Siess").
Maq I Ex. A6—Invalidity by U.S. Pat. No. 6,544,216 B1 ("Sammler").
Maq I Ex. A7—Invalidity by U.S. Pat. No. 6,247,007 B1 ("Bedingham").
Maq II Ex. A1—238 Invalidity—Aboul-Hosn Chart.
Maq II Ex. A2—238 Invality—Hemopump Char.
Maq II Ex. A3—238 Invalidity—Jegaden Chart.
Maq II Ex. A4—23 Invalidity—Voelker Chart.
Maq II Ex. A5—238 Invality—Siess Chart.
Maq II Ex. A6—238 Invalidity—Bedingham Chart.
Abiomed's Surreply to Maquet's Motion for Reconsideration dated Oct. 26, 2018.
Sur-Response of Maquet Cardiovascular LLC Concerning Its Motion for Reconsideration and/or Clarification of Claim Construction Regarding "Passing Purge Fluid" Terms dated Nov. 2, 2018.
Abiomed's Opposition to Maquet's Motion for Reconsideration dated Oct. 5, 2018.
Reply Memorandum of Law in Further Support of Maquet Cardiovascular LLC's Motion for Reconsideration and/or Clarification of Order on Claim Construction Regarding "Passing Purge Fluid" Terms dated Oct. 17, 2018.
Office Action for U.S. Appl. No. 16/138,788 dated Dec. 10, 2018
Office Action for U.S. Appl. No. 16/143,289 dated Feb. 12, 2019.
Letter from Scott Weingaertner to Michael S. Connor erroneously dated Mar. 14, 2018 (should have been Mar. 14, 2019), 5 pages.
Transcript, Markman Hearing, Day 1, Apr. 24, 2018, Case No. 1:16-10914-FDS, Document No. 231 (May 14, 2018), 136 pages.
Transcript, Markman Hearing, Day 2, Apr. 25, 2018, Case No. 1:16-10914-FDS, Document No. 231 (May 14, 2018), 96 pages.
Transcript, Motion for Reconsideration Hearing, Case No. 1:16-10914-FDS, Document No. 273 (Nov. 2, 2018), 54 pages.
Technology Tutorial (Presentation) by Maquet Cardiovascular LLC, Case No. 1:16-cv-10914-FDS (Apr. 10, 2018), 22 pages.
Technology Tutorial (Video) by Maquet Cardiovascular LLC, Case No. 1:16-cv-10914-FDS (Apr. 10, 2018).
Technology Tutorial (Video) by Abiomed Inc., Case No. 1:16-cv-10914-FDS (Apr. 9, 2018).
Office Action for U.S. Appl. No. 16/159,553 dated Mar. 19, 2019.

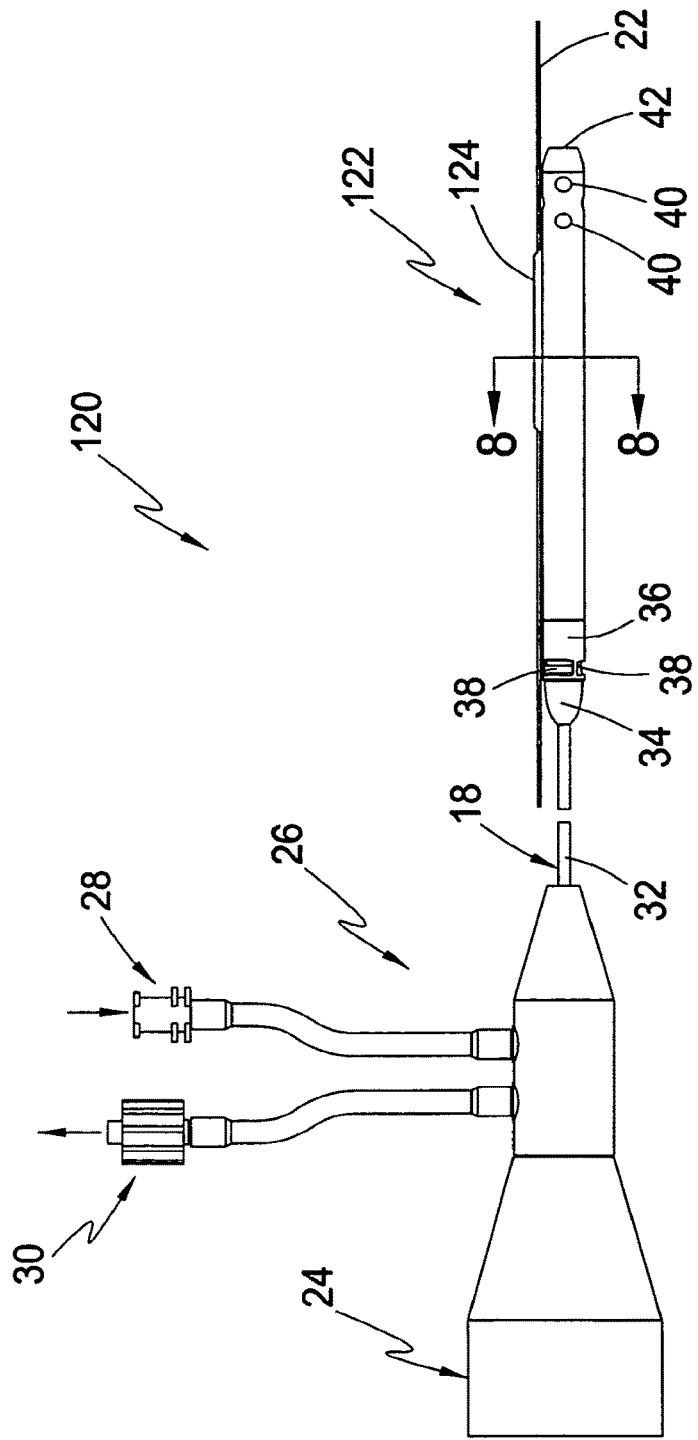

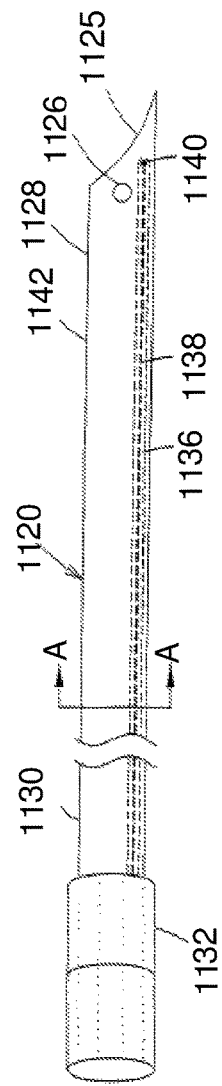
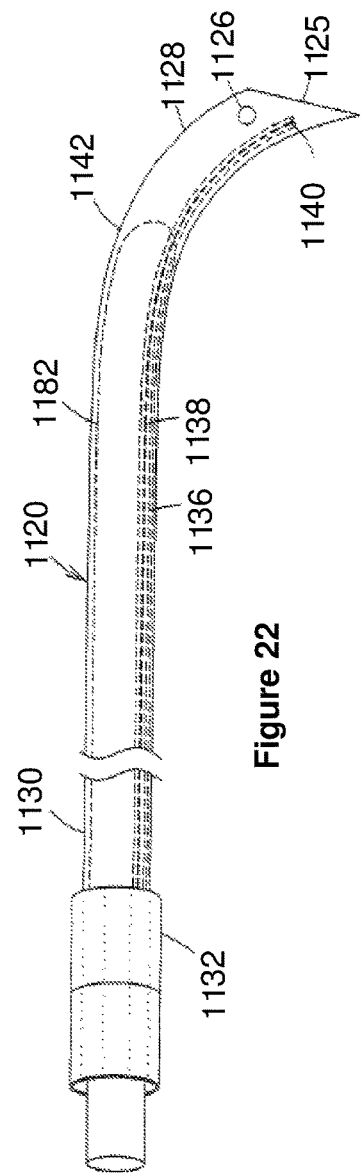
Figure 20
Figure 22

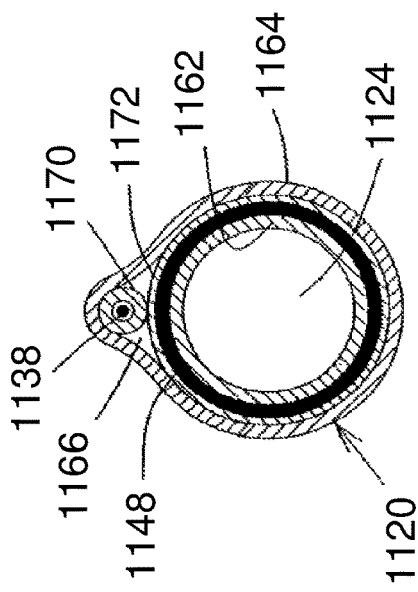
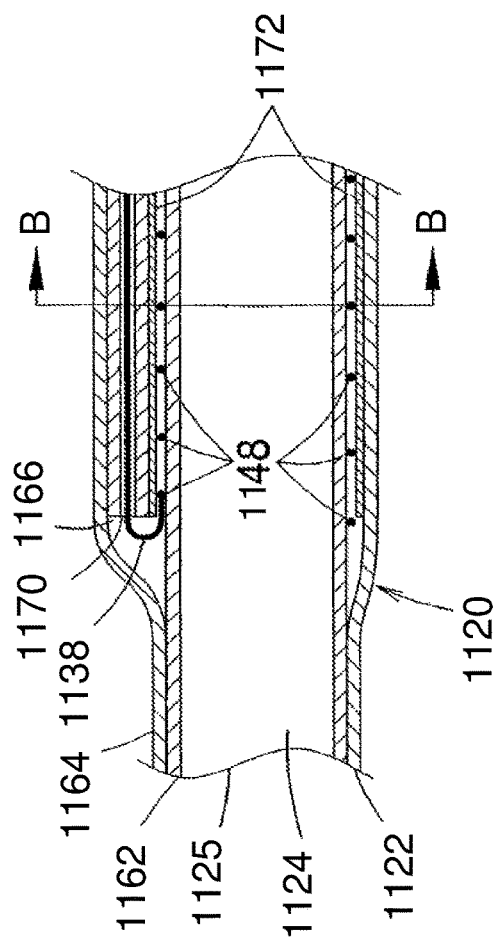
Figure 26
Figure 25

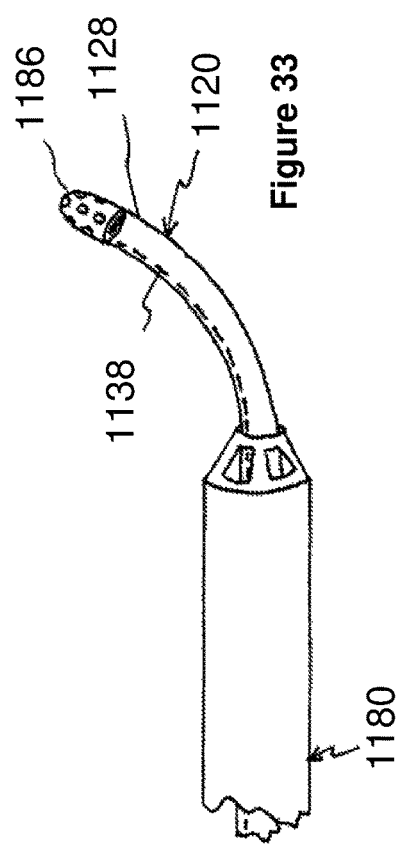
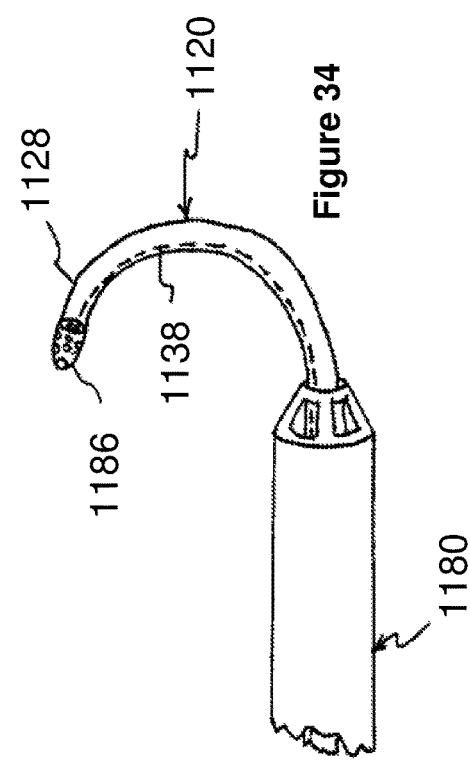

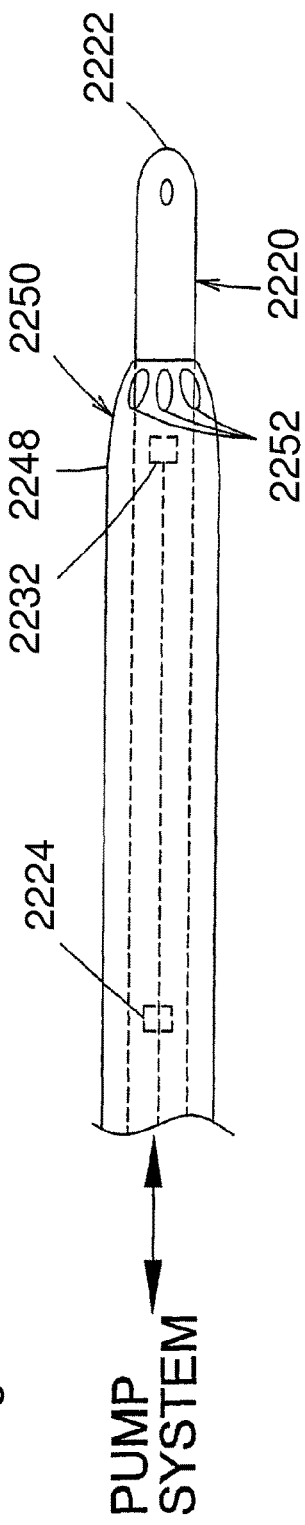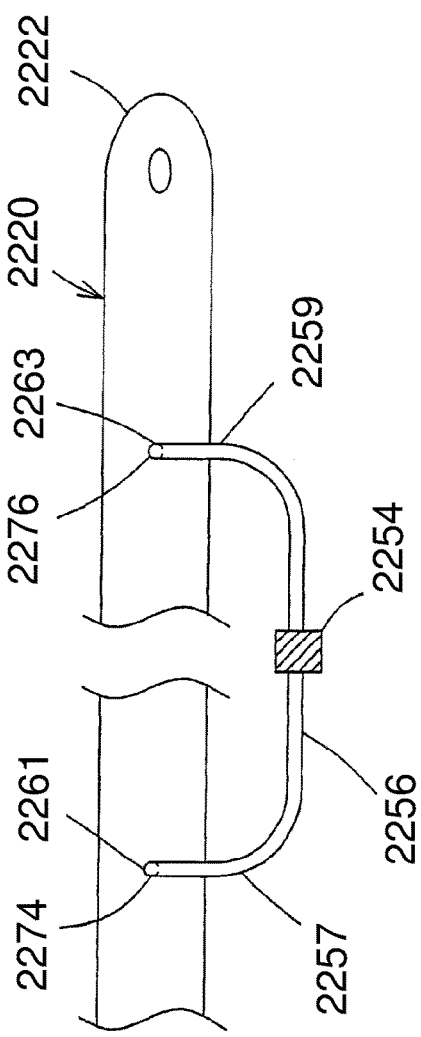
Figure 42
Figure 43

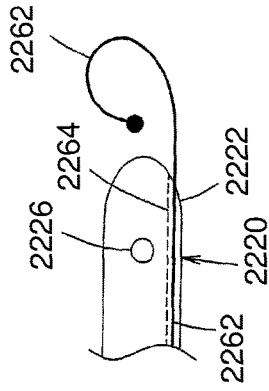
Figure 51
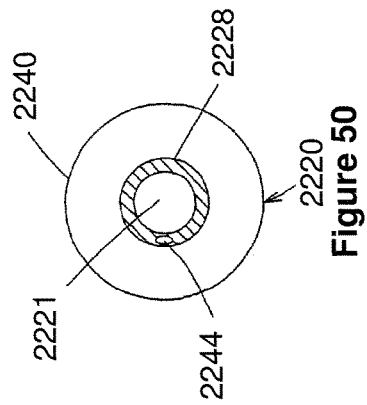
Figure 50
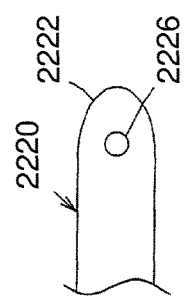
Figure 47
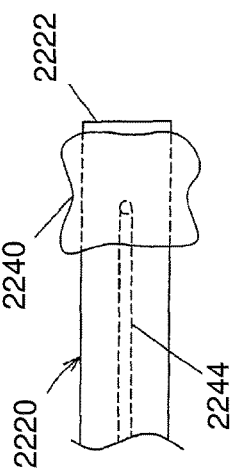
Figure 48
Figure 49

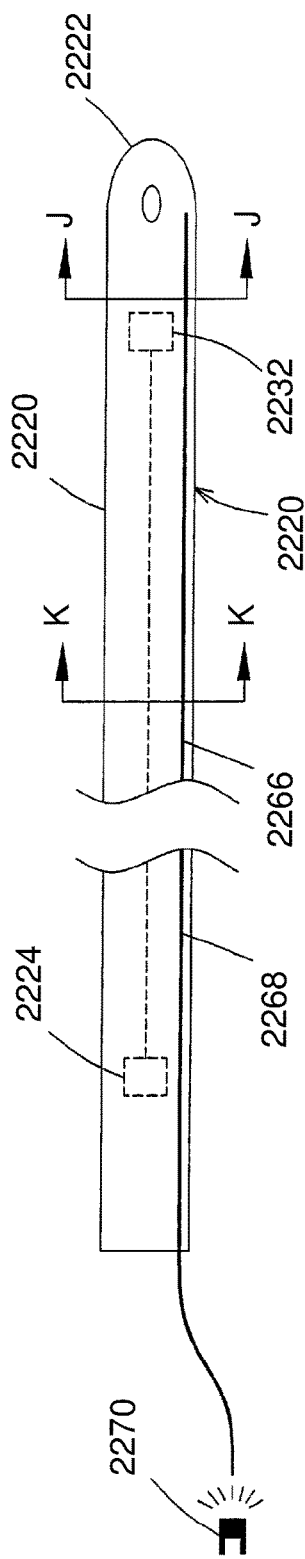
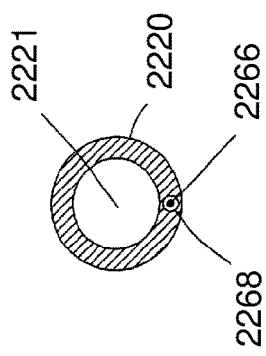
Figure 52
Figure 53

GUIDABLE INTRAVASCULAR BLOOD PUMP AND RELATED METHODS

RELATED APPLICATIONS

This application is a divisional of U.S. patent application Ser. No. 14/543,815, (now U.S. Pat. No. 9,327,068, issued May 3, 2016), which is a continuation of U.S. patent application Ser. No. 12/772,810, field May 3, 2010 (now U.S. Pat. No. 8,888,728, issued Nov. 18, 2014), which is a continuation of U.S. patent application Ser. No. 11/375,926, filed Mar. 15, 2006 (now U.S. Pat. No. 7,731,675, issued Jun. 8, 2010), which is a divisional of U.S. patent application Ser. No. 10/070,178, filed Jul. 19, 2002, (now U.S. Pat. No. 7,022,100, issued Apr. 4, 2006) which claims the benefit of PCT/US00/24515 filed Sep. 1, 2000, which claims the benefit of provisional U.S. Patent Application Ser. No. 60/152,249 filed Sep. 3, 1999.

FIELD OF THE INVENTION

The present invention relates generally to blood pumps and, more particularly, to an improved intra-vascular blood pump having a guide mechanism which provides the ability to selectively guide the intravascular pump to a desired location within a patient's circulatory system.

DESCRIPTION OF RELATED ART

Over the years, various types of blood pumps have been developed for the purpose of augmenting or replacing the blood pumping action of damaged or diseased hearts. Blood pumps are commonly used in three situations: (1) for acute support during cardio-pulmonary operations; (2) for short-term support while awaiting recovery of the heart from surgery; or (3) as a bridge to keep a patient alive while awaiting heart transplantation. The pumps may be designed to provide right and/or left ventricular assist, although left ventricle assist is the most common application in that it is far more common for the left ventricle to become diseased or damaged than it is for the right ventricle.

Blood pumps must provide leak-free operation and must avoid contamination of the fluid by the pump components and the external environment. Such pumps must also pump the fluid at a suitable rate without applying excessive Reynolds shear stress to the fluid. It is well known to those skilled in the art that lysis or cell destruction may result from application of shear stress to cell membranes. Red blood cells are particularly susceptible to shear stress damage as their cell membranes do not include a reinforcing cytoskeleton to maintain cell shape. Lysis of white blood cells and platelets also occurs upon application of high shear stress. Lysis of red blood cells can result in release of cell contents which trigger subsequent platelet aggregation. Sublytic shear stress leads to cellular alterations and direct activation and aggregation of platelets and white blood cells.

Intravascular blood pumps comprise miniaturized blood pumps capable of being percutaneously or surgically introduced into the vascular system of a patient, typically to provide left and/or right heart support. One type of intravascular pump is an axial flow blood pump comprising a cable-mounted rotor surrounded by a protective shroud. The pump, along with the rotor and shroud, are mounted at the end of an elongated flexible catheter. The catheter is inserted into the aorta from a remote entry point, such as an incision below the groin that provides access into a femoral artery. The catheter then passes through the descending aorta until it reaches the ascending aorta, near the heart. The catheter device encloses a rotating drive cable which is coupled to the impeller blade at one end, and which emerges from the exposed end of the catheter, near the patient's groin, at the other end. When the exposed end of the drive cable is mechanically rotated, using a device located outside the patient's body, it conveys the rotational force through the length of the catheter, causing the impeller to spin at high speed near the heart. This type of blood pump finds particular application in providing ventricular assist during surgery or providing temporary bridging support to help a patient survive a crisis.

While generally effective in providing ventricular assisting functions, prior art intravascular blood pumps nonetheless suffer various drawbacks. A significant drawback is that prior art intravascular blood pumps are difficult to guide into the appropriate position within the circulatory system of a patient. This is due largely to the fact that the elongated catheter is incapable of providing the degree of control necessary to easily negotiate the pump through the tortuous pathways leading up to and into the heart. When attempting to place the blood pump in a trans-valvular configuration (with the inlet in the left ventricle and the pump outlet in the ascending aorta), the natural tendency of the catheter to stay straight may cause the pump to be inadvertently placed in the carotid ostia, which can be dangerous if the pump is operated to withdraw blood from the brain.

To overcome these difficulties, certain guide mechanisms may be employed to assist the physician placing the pump in the appropriate position within the circulatory system. One type of supplemental guide mechanism is a guide catheter. Guide catheters are designed with certain guidability characteristics such that physicians can selectively position them within the vasculature or heart with relative ease. A central lumen is provided within the guide catheter such that the intravascular pump may be introduced therein and guided while it is advanced towards the predetermined circulatory site. While generally effective at providing a guiding feature for such intravascular blood pumps, employing such supplemental guide mechanisms is nonetheless disadvantageous in that they consume valuable space within the vessels. A guide catheter, for example, would necessarily be larger in diameter than the diameter of the pump and protective shroud in order to provide adequate passage of those components. As will be appreciated, this restricts the amount of space available for blood to flow within the particular vessel, and increases the size of the required puncture wound for accessing the vessel.

The present invention is directed at eliminating and/or reducing the effects of the foregoing drawbacks of prior art intravascular blood pumps.

SUMMARY OF THE INVENTION

The present invention overcomes the drawbacks of the prior art by providing an improved intravascular blood pump equipped with integrated features for selectively guiding the intravascular blood pump to a predetermined location in the patient's circulatory system, i.e. heart and/or vasculature. In so doing, the intravascular blood pump of the present invention eliminates the need for supplemental guiding mechanisms, such as a separate, large diameter guide catheter as used in the prior art.

In a first broad aspect of the present invention, an intravascular blood pump system is provided comprising an intravascular blood pump having a cannula coupled thereto and an "over-the-wire" type guide mechanism for selectively positioning the intravascular blood pump and cannula at a predetermined location within the circulatory system of a patient. To accomplish this, a central lumen is formed through at least a portion of the intravascular blood pump system such that a guide element, such as a guide wire, may be progressed therethrough and advanced to the predetermined location in the circulatory system of the patient. After the guide element is advanced to this desired location, the intravascular blood pump and cannula may thereafter be advanced along the guide element to the desired location.

In a second broad aspect of the present invention, an intravascular blood pump system is provided comprising an intravascular blood pump having a cannula coupled thereto and a "side-rigger" or "rapid exchange" type guide mechanism for selectively positioning the intravascular blood pump and cannula at a predetermined location within the circulatory system of a patient. To accomplish this, a side lumen is formed along a length of at least one of the intravascular blood pump and the cannula. A guide element, such as a guide wire, may be advanced to the predetermined location in the circulatory system of the patient. After the guide element is advanced to this desired location, the intravascular blood pump and cannula may thereafter be advanced along the guide element to the desired location.

In a third broad aspect of the present invention, an intravascular blood pump system is provided comprising an intravascular blood pump having a cannula coupled thereto and a "guide catheter" type guide mechanism for selectively positioning the intravascular blood pump and cannula at a predetermined location within the circulatory system of a patient. The pump system of this broad aspect includes a conduit assembly and a separate pump assembly. The conduit assembly includes a guide catheter, a rotor shroud, and a cannula, with the cannula and guide catheter disposed on either side of the rotor shroud. The pump assembly includes a rotor, a drive member coupled to the rotor, and a pump disposed between the rotor and the drive member. The guide catheter is dimensioned to receive and guide the pump assembly to the point where the rotor docks within the rotor shroud so as to form an operational blood pump. This configuration allows the conduit assembly to be precisely and efficiently guided into a desired position within the body through the use of conventional guiding techniques well known in interventional cardiology. The pump assembly may thereafter be introduced into and guided within the conduit until the pump assembly is docked within the rotor shroud. This dual construction arrangement provides improved placement of the pump assembly by using the conduit as a guiding mechanism.

The foregoing broad aspects of the present invention may be manifested according to the following recitations:

According to a first broad recitation of the present invention, an intravascular blood pump system is provided comprising an intravascular blood pump having a cannula coupled thereto, and a guide mechanism adapted to guide the intravascular blood pump and cannula to a predetermined location within the circulatory system of a patient.

In a further embodiment, the intravascular blood pump includes a rotor, a shroud for receiving the rotor, and a drive cable coupled to the rotor for driving the rotor within the shroud.

In a further embodiment, the cannula is coupled to the shroud of the intravascular blood pump.

In a further embodiment, the guide mechanism comprises a guide catheter coupled to the shroud.

In a further embodiment, the guide catheter may be used to guide the shroud and cannula to the predetermined location within the circulatory system of the patient, after which point the rotor and drive cable of the intravascular blood pump may be docked within the shroud for pump operation.

In a further embodiment, the drive cable sheath is provided having a central lumen for receiving the drive cable, and wherein a purge fluid delivery system is coupled to the drive cable sheath to deliver purge fluid to the rotor.

In a further embodiment, the drive cable sheath includes at least one side lumen for delivering the purge fluid towards the rotor.

In a further embodiment, a portion of the purge fluid is delivered through the at least one side lumen and past the rotor, and a portion of purge fluid is rerouted back from the rotor through the central lumen of the drive cable.

In a further embodiment, a perfusion assembly is provided communicatively coupled to the guide catheter for selectively rerouting blood from within the guide catheter to a point downstream from the introduction site of the guide catheter into the vasculature of the patient.

In a further embodiment, the perfusion assembly includes a first conduit communicatively coupled to the guide catheter, a second conduit dimensioned to be introduced into the vasculature of the patient, and a selectively operable valve disposed in between the first conduit and the second conduit.

In a further embodiment, a blood pressure detection mechanism is provided to detect the pressure of the blood proximate at least one of the intravascular blood pump and cannula.

In a further embodiment, the blood pressure detection mechanism comprises at least one of fluid filled column disposed within at least a portion of the cannula, a piezoelectric element coupled to at least one of the intravascular blood pump and cannula, and a strain gauge coupled to at least one of the intravascular blood pump and cannula.

In a further embodiment, the blood pressure detection mechanism involves calculating blood pressure based on the relationship between the torque and motor current of a motor used to drive the rotor.

In a further embodiment, the guide mechanism comprises a guide element disposed at least partially within the cannula.

In a further embodiment, the guide element comprises a guide wire for passage through a side lumen formed in the cannula.

In a further embodiment, the guide element comprises a selectively deformable element disposed at least partially within the cannula.

In a further embodiment, the intravascular blood pump and cannula may be selectively advanced to the predetermined location within the vasculature of the patient by first passing the guide wire to the predetermined location and thereafter sliding the intravascular blood pump and cannula along the guide wire to the predetermined location.

In a further embodiment, the guide element comprises a guide wire for passage through a lumen extending through the drive cable and rotor.

In a further embodiment, the intravascular blood-pump and cannula may be selectively advanced to the predetermined location within the vasculature of the patient by first passing the guide wire to the predetermined location and thereafter sliding the intravascular blood pump and cannula along the guide wire to the predetermine location.

In a further embodiment, the guide mechanism further includes guide element for passage through the guide catheter to facilitate placement of the shroud and the cannula at the predetermined location within the vasculature of the patient.

In a further embodiment, the guide mechanism further includes a guide element for passage through a side lumen formed along at least a portion of the guide catheter.

In a further embodiment, the guide element comprises at least one of a guide wire and a balloon catheter.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 7 is side view of the guidable intravascular blood pump system of the type shown in FIG. 6 including a motor coupler and purge fluid delivery system according to an exemplary embodiment of the present invention;

FIG. 20 corresponds to FIG. 1 of U.S. Ser. No. 09/280,988, and is a schematic side view of a steerable cannula in the undeformed state in accordance with the first embodiment of U.S. Ser. No. 09/280,988;

FIG. 22 corresponds to FIG. 3 of U.S. Ser. No. 09/280,988, and is a schematic side view of the steerable cannula in the deformed state in accordance with the first embodiment of U.S. Ser. No. 09/280,988;

FIG. 25 corresponds to FIG. 6 of U.S. Ser. No. 09/280,988, and is a schematic cut-away view of a steerable cannula in accordance with a fourth embodiment of U.S. Ser. No. 09/280,988;

FIG. 26 corresponds to FIG. 7 of U.S. Ser. No. 09/280,988, and is a schematic cross-sectional view taken along line B-B of FIG. 25;

FIG. 33 corresponds to FIG. 14 of U.S. Ser. No. 09/280,988, and is a schematic side view showing a steerable cannula used in a co-axial configuration in accordance with a ninth embodiment of U.S. Ser. No. 09/280,988, wherein the steerable cannula is advanced to a first relative position;

FIG. 34 corresponds to FIG. 15 of U.S. Ser. No. 09/280,988, and is a schematic side view showing a steerable cannula of FIG. 33, wherein the steerable cannula is advanced to a second relative position.

FIG. 42 corresponds to FIG. 7 of U.S. Ser. No. 09/280,970, and is a schematic side view of a third embodiment of U.S. Ser. No. 09/280,970;

FIG. 43 corresponds to FIG. 8 of U.S. Ser. No. 09/280,970, and is a schematic side view of a fourth embodiment of U.S. Ser. No. 09/280,970;

FIG. 47 corresponds to FIG. 12 of U.S. Ser. No. 09/280,970, and is a schematic side view of a seventh embodiment of U.S. Ser. No. 09/280,970;

FIGS. 48 and 49 correspond to FIGS. 13 and 14, respectively, of U.S. Ser. No. 09/280,970, and are schematic side views of an eighth embodiment of U.S. Ser. No. 09/280,970;

FIG. 50 corresponds to FIG. 15 of U.S. Ser. No. 09/280,970, and is a schematic cross-sectional view taken along line H-H of FIG. 49;

FIG. 51 corresponds to FIG. 16 of U.S. Ser. No. 09/280,970, and is a schematic side view of a ninth embodiment of U.S. Ser. No. 09/280,970;

FIG. 52 corresponds to FIG. 17 of U.S. Ser. No. 09/280,970, and is a schematic side view of a tenth embodiment of U.S. Ser. No. 09/280,970;

FIG. 53 corresponds to FIG. 18 of U.S. Ser. No. 09/280,970, and is a schematic cross-sectional view taken along line K-K of FIG. 52.

DETAILED DESCRIPTION OF THE INVENTION

Illustrative embodiments of the invention are described below. In the interest of clarity, not all features of an actual implementation may be described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention involves an intravascular pump system for use in a number of broad ranging applications involving the augmentation of blood flow within the circulatory system of a patient. As will be described below, the intravascular blood pump system of the present invention overcomes the drawbacks of the prior art by providing a guide mechanism as part of the intravascular blood pump. This advantageously allows the intravascular blood pump to be selectively guided to a predetermined location within the circulatory system of a patient without the need for bulky supplemental guide mechanisms, such as a separate guide catheter.

The intravascular pump assembly of the present invention is particularly suited for trans-valvular use, such as for left and/or right ventricular assist procedures. By way of example only, such ventricular assist procedures may be employed in cardiac operations including, but not limited to, coronary bypass graft (CABG), cardio-pulmonary bypass (CPB), open chest and closed chest (minimally invasive) surgery, bridge-to-transplant and/or failure-to-wean-from-bypass situations. It is to be readily understood, however, that the intravascular blood pump assembly and methods of the present invention are not to be limited to such applications. Moreover, while illustrated and described largely with reference to left-heart assist applications, it is to be readily understood that the principles of the present invention apply equally with regard to right-heart assist application, which are contemplated as within the scope of the present invention. These and other variations and additional features will be described throughout.

Figure 1:
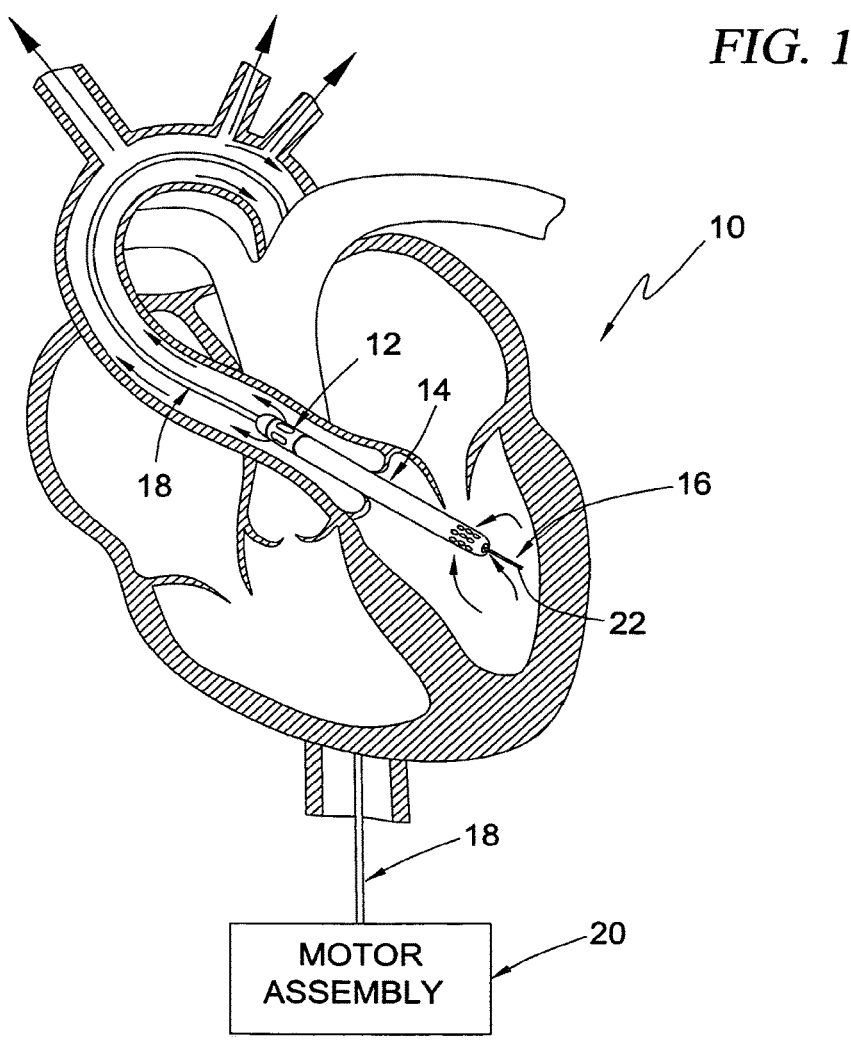
FIG. 1 is a partial sectional view of a human heart illustrating an intravascular blood pump system having an "over-the-wire" type guide mechanism according to a first broad aspect of the present invention positioned, by way of example, in a trans-valvular configuration to provide left-heart assist.

Referring to FIG. 1, shown is a guidable intra-vascular blood pump system 10 according to a first broad aspect of the present invention shown, by way of example only, in a left-heart assist configuration within a human heart. The system 10 includes an intravascular blood pump 12, a cannula 14, and an "over-the-wire" type guide mechanism 16. A drive cable assembly 18 and a motor assembly 20 are provided to drive the intravascular blood pump 12. The "over-the-wire" guide mechanism 16 comprises a suitable guide element dimensioned to pass slideably through a central lumen extending through the drive cable 18, blood pump 12, and cannula 14. Suitable guide elements may include any number of conventional guiding devices, including but limited to those employed in cardiology. By way of example only, the guide element is shown as a guide wire 22. According to the present invention, the "over-the-wire" guide mechanism 16 provides the ability to selectively guide the blood pump 12 and cannula 14 to a predetermined position in the circulatory system of a patient, such as the trans-valvular position shown.

To accomplish this, the guide wire 22 is first introduced into the vascular system of a patient through any suitable access point, such as through the use of the well known Seldinger technique. The guide wire 22 can then be advanced within the patient to a desired location within the circulatory system of the patient. This may be done using the control features of the guide wire 22 itself, or may be facilitated through the use of any number of supplemental guidance mechanisms or techniques to ensure the proper and efficient placement of the guide wire 22. Such supplemental guidance techniques may include, but are not necessarily limited to, guide catheters and/or techniques involving ultrasound or fluoroscopy. Once the guide wire 22 is positioned at the desired location (such as in left ventricle as shown), the blood pump 12 and cannula 14 may thereafter be advanced along the guide wire 22 and positioned in the trans-valvular configuration shown. Under the operation of the motor assembly 20, the blood pump 12 may be used for left-heart assist by selectively withdrawing blood from the left ventricle (through the interior of the cannula 14) for delivery outward through outflow apertures formed in the blood pump 12. This outflow from the blood pump 12 flows along the exterior of the drive cable assembly 18 in a substantially axial fashion for arterial distribution throughout the body.

Figure 2:
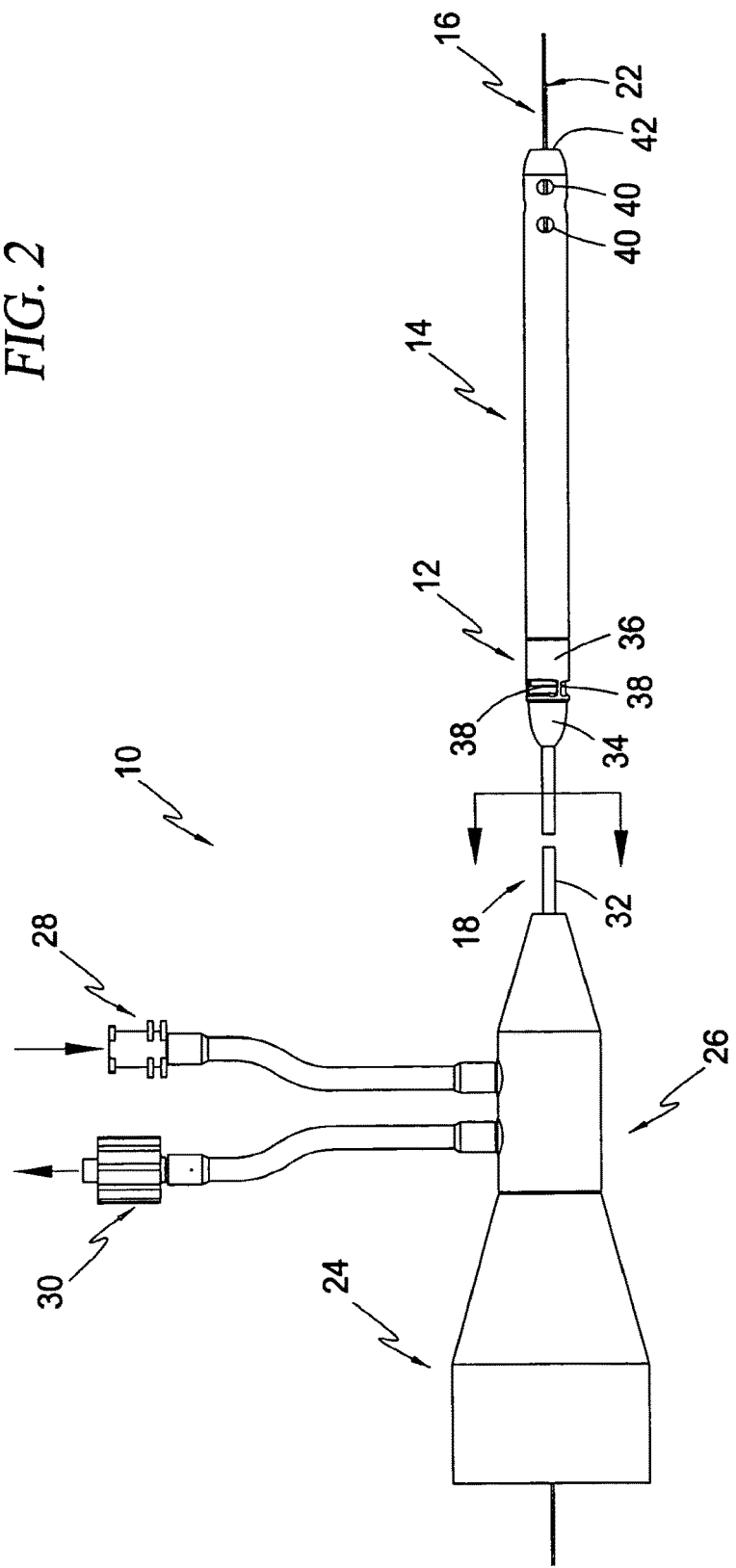
FIG. 2 is side view of the guidable intravascular blood pump system of the type shown in FIG. 1 including a motor coupler and purge fluid delivery system according to an exemplary embodiment of the present invention.

Referring to FIGS. 2-5, an exemplary embodiment of the intravascular blood pump system 10 of FIG. 1 will now be described. As shown in FIG. 2, the intravascular blood pump system 10 includes a coupler 24 and, as will be described in greater detail below, a purge fluid delivery system 26 for providing a two-way fluid flow within the drive cable assembly 18 during pump operation. The purge fluid delivery system 26 includes a fluid inlet conduit 28 for introducing pressurized purge fluid from a fluid source (not shown) for delivery into the blood pump 12, and a fluid outlet conduit 30 to withdraw a return flow of purge fluid from the blood pump 12. The motor coupler 24 establishes a mechanical connection between a motor (not shown) and a drive cable (not shown) for providing motive force to the blood pump 12 for pump operation. The drive cable assembly 18 includes a drive cable sheath 32 which, in addition to serving a purge fluid delivery function, also serves as a protective housing for the drive cable (not shown). Although shown in broken form for clarity, it will be appreciated that the drive cable assembly 18 (and all components thereof) may be provided in any suitable length sufficient for intravascular applications. That is to say, the length of the drive cable assembly 18 must be enough to reach between the motor coupler 24 and purge fluid delivery system 26, located outside the patient, and the desired location within the patient's circulatory system where the blood pump 12 is to be positioned.

The intravascular blood pump 12 is shown (by way of example only) as an axial flow intravascular blood pump. The blood pump 12 includes pump body 34, a rotor shroud 36 having flow ports 38, and an internally disposed rotor (not shown) having a shaft rotatably disposed within the pump body 34 and an impeller rotatably disposed within the rotor shroud 36. The cannula 14 is fixedly attached to the rotor shroud 36 and may extend any suitable length therefrom depending upon the particular intravascular application. The cannula 14 preferably includes a plurality of ports or fenestrations 40 about its distal region, as well as an end port 42, which allow for the ingress or egress of blood into or from the cannula 14 depending upon the operation of the blood pump 12. That is to say, if the pump 12 is configured for left-heart assist as shown in FIG. 1, then the ports 40, 42 will allow the ingress of blood into the cannula 14 from the left ventricle. If, on the other hand, the blood pump 12 is configured for right-heart assist (i.e. with the pump 12 in the right atrium and the distal end of the cannula 14 located within the pulmonary artery), then the ports 40, 42 will allow the egress of blood from the cannula 14 into the pulmonary artery. (Details on right-heart assist applications will be discussed in greater detail below.) The pump 12 and cannula 14 may be dimensioned to any suitable diameter for intravascular applications. For example, the range of sizes may include, but is not necessarily limited to, 9 French to 30 French, although the range is more preferably from 14 French to 24 French, and most preferably from 18 French to 20 French.

The "over-the-wire" type guide mechanism 16 includes the guide wire 22 and, as will be explained in greater detail below, a central lumen extending through the cannula 14, blood pump 12, drive cable assembly 18, purge fluid delivery system 26, and motor coupler 24. As noted above, the central lumen is dimensioned to slideably receive the guide wire 22 such that the blood pump 12 and cannula 14 may be slideably advanced along the guide wire 22 to a desired location within the circulatory system of a patient after the guide wire 22 has been so positioned using conventional guidance techniques. It is to be readily understood that, while shown as a conventional guide wire 22, the guide element forming part of the guide mechanism 16 of the present invention may include any number of well known guidance mechanisms depending upon the application, including but not limited to balloon catheters, imaging wires, and guide catheters dimensioned to be slideably received through the central lumen. For example, although not appropriate for retrograde progression (such as the left-heart application shown in FIG. 1), a balloon catheter may be a suitable guidance mechanism for a right-heart assist application. In such a case, the balloon may be inflated and used as a "sail" to direct the catheter to a desired location (such as the pulmonary artery), after which point the blood pump 12 and cannula 14 can be advanced over the catheter to a trans-valvular configuration with the blood pump 12 in the right atrium and the ports 38, 40 of the cannula 14 in the pulmonary artery.

Figure 3:
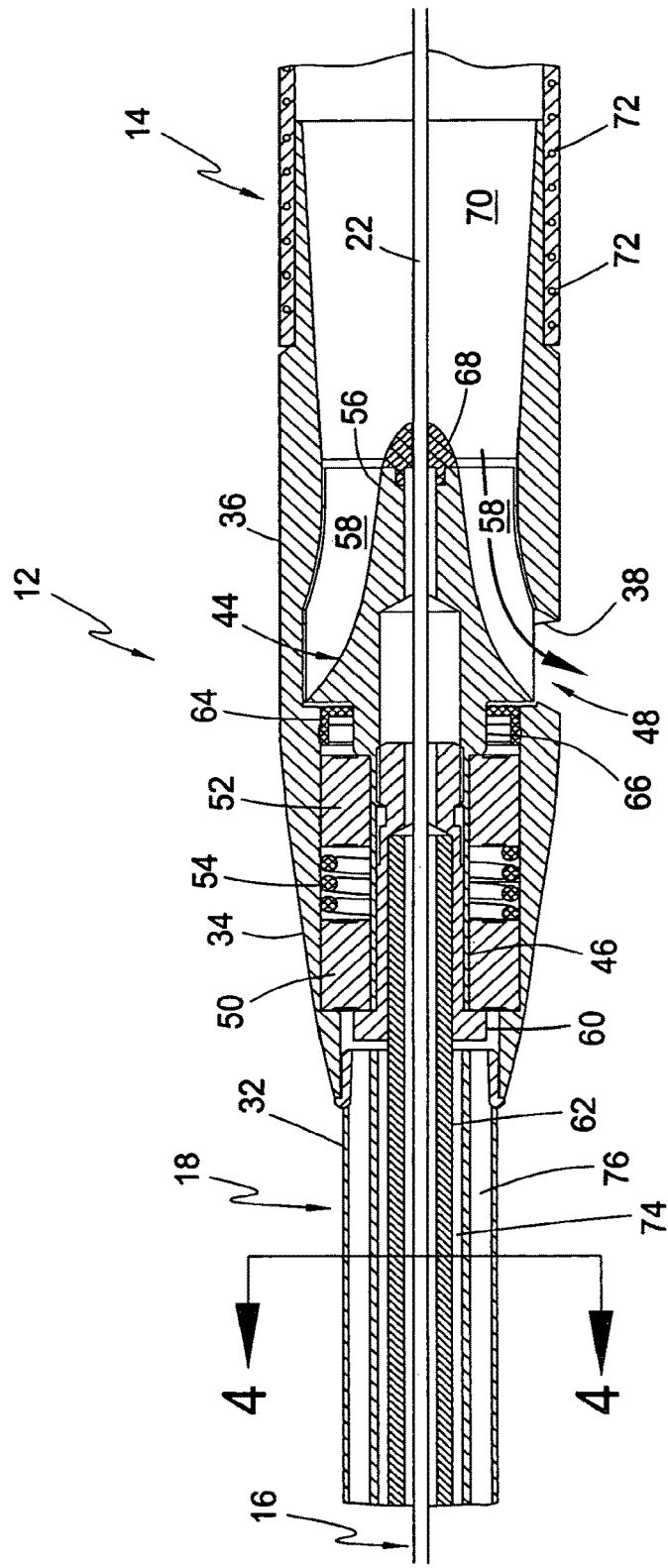
FIG. 3 is a cross-sectional view illustrating an exemplary construction of the blood pump, drive cable assembly, and cannula of the intravascular blood pump system according to the first broad aspect of the present invention.
Figure 4:
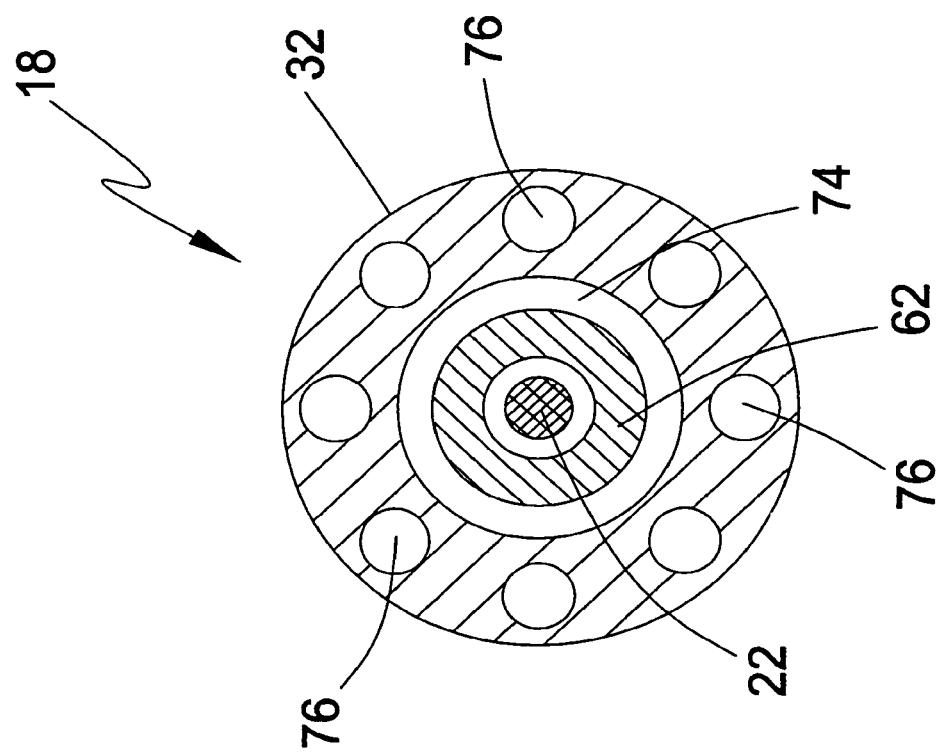
FIG. 4 is a cross-sectional view taken along lines 4-4 of FIG. 3 illustrating an exemplary construction of the drive cable assembly and guide mechanism according to the first broad aspect of the present invention.

FIGS. 3 and 4 further detail the construction of the blood pump 12, cannula 14, drive cable assembly 18, and "overthe-wire" guide mechanism 16. The blood pump 12 includes a rotor 44 having a shaft 46 and an impeller 48. The shaft 46 is rotatably disposed within the pump body 34 via a bearing pack comprising, by way of example, ball bearing assemblies 50, 52 and spring 54. Ball bearings assemblies 50, 52 are well known in the art, each comprising an inner race which rotates along with the rotor shaft 46, an outer race which remains in a static and fixed position against the inner surface of the pump body 34, and a plurality of ball bearings disposed between the inner and outer races. The spring 54 biases each bearing assembly 50, 52 axially away from one another to reduce axial play during pump operation. The shaft 46 is generally hollow and dimensioned to receive a cable adapter 60 therein for the purpose of coupling the rotor 44 to a drive cable 62 forming part of the drive cable assembly 18. The drive cable 62 may be secured to the cable adapter 60 in any number of suitable fashions, including but not limited to the use of adhesives, crimping, and laser welding. These same techniques may be used to secure the cable adapter 60 within the shaft 46 of the rotor 44. A radial seal 64 is provided in between the wall of the pump body 34 and a distal stepped region 66 on the rotor shaft 46, the function of which will be described below.

The impeller 48 includes a hub 56 and a plurality of blades 58 extending therefrom. The hub 56 is generally conical and, according to the first broad aspect of the present invention, is hollow throughout to form part of the central lumen of the guide mechanism 16. In this regard, the hub 56 is preferably provided with a gasket or seal member 68 at its distal tip. The seal member 68 may be made of any suitable sealing material (including but not limited to silicone) such that the pump 12 and cannula 14 may be easily progressed along the guide wire 22 for delivery to a desired circulatory site. The seal member 68 should also be robust enough to prevent the ingress of blood into the interior of the rotor hub 56 during pump operation, whether the guide wire 22 remains in place or is fully withdrawn. The blades 58 are dimensioned to reside in close tolerance with the interior surface of the shroud 36. In operation, the blades 58 impart both an axial and radial vector on the blood which causes it to flow outward through the flow ports 38 formed in the shroud 36. As used herein, the term "axial flow" is deemed to include flow characteristics like that shown in FIG. 3, which include both an axial and slight radial component. It is to be readily appreciated that, although shown as an axial flow type, blood pump 12 may comprise any number of suitable types of intravascular blood pumps, including but not limited to so-called "mixed flow" intravascular blood pumps without departing from the scope of the present invention.

The cannula 14 is coupled at its proximal end to the rotor shroud 36. This may be accomplished in any number of fashions, including but not limited to the use of adhesives. This may also be facilitated by dimensioning the shroud 36 to include a narrow inlet region 70 capable of being received flushly within the proximal end of the cannula 14. The inlet region 70 of the shroud 36 should preferably have a tapered interior surface for establishing a smooth flow transition between the cannula 14 and the region containing the impeller blades 58. Although shown as a single integral element, it is to be understood that the pump body 34 and shroud 36 may comprise two separate (and sometimes separable) components, the significance of which will become apparent below. The pump body 34 and shroud 36 may be constructed from any number of suitable materials, including but not limited to stainless steel or other medical grade compositions or alloys. The cannula 14 may also be constructed from any number of suitable materials, including but not limited to medical grade plastics. As shown, the cannula 14 may also be fortified with spiral-wound reinforcement wire 72 within the walls of the cannula 14.

The drive cable assembly 18 includes the drive cable 62 and the drive cable sheath 32. The drive cable 62 is coupled to the rotor 44 via the cable adapter 60. The drive cable sheath 32 includes a central lumen 74 and a plurality of side lumens 76. The central lumen 74 serves as a protective covering for the drive cable 62. The central lumen 74, along with the side lumens 76, also forms part of the purge fluid delivery system 26 shown above in FIG. 2, which will be described in greater detail below. The side lumens 76 are provided in fluid communication with the fluid inlet conduit 28, while the central lumen 74 is provided in fluid communication with the fluid outlet conduit 30. The side lumens 76 are thus configured to deliver purge, fluid into the pump 12, while the central lumen 74 is configured to transport purge fluid away from the pump 12 along the length of the drive cable 62.

The pressurized purge fluid within the side lumens 76 may take one of two flow paths upon entry into the pump 12. One flow path passes through the interior of the pump 12 and onward past the radial seal 64 to prevent the ingress of blood into the pump body 34 during pump operation. More specifically, the purge fluid flows distally around the cable adapter 60, through the ball bearing assemblies 50, 52, and onward past the radial seal 64. This egress of purge fluid past the radial seal 64 can be controlled to effectively thwart the ingress of blood past the radial seal 64, which might otherwise cause clotting and/or pump damage. The other flow path is directed back out the central lumen 74 for delivery to the fluid outlet conduit 30. In so doing, this flow path bathes the components of the pump 12 and/or drive cable 62 and thereby reduces frictional heating within the pump 12 and/or the central lumen 74 of the sheath 32 during pump operation.

The "over-the-wire" guide mechanism 16 includes a central lumen through which the guide wire 22 may extend for the purpose of slideably advancing the blood pump 12 and cannula 14 into a desired position within the circulatory system of a patient. In the embodiment shown, this central lumen is established by forming and co-aligning the individual central lumens within each of the drive cable 62, the cable adapter 60, the shaft 46 and hub 56 of the rotor 44, and the cannula 14. In this regard, the drive cable 62 is preferably of wound-wire construction having a central lumen formed therein. The central lumens within the cable adapter 60, rotor 44, and gasket 68 may be formed via machining or molding processes. These central lumens should preferably be sized such that they permit the slideable passage of the pump 12 and cannula 14 therealong, but do not interfere with or constrain the guide wire 22 to cause inadvertent rotation of the guide wire 22 during pump operation. As noted above, it is also contemplated to remove the guide wire 22 after the pump 12 and cannula 14 are properly positioned in the patient. In this case, the gasket or seal 68 on the hub 56 should be robust enough to reseal after the guide wire 22 is withdrawn and prevent the ingress of blood into the interior of the rotor 44.

Figure 5:
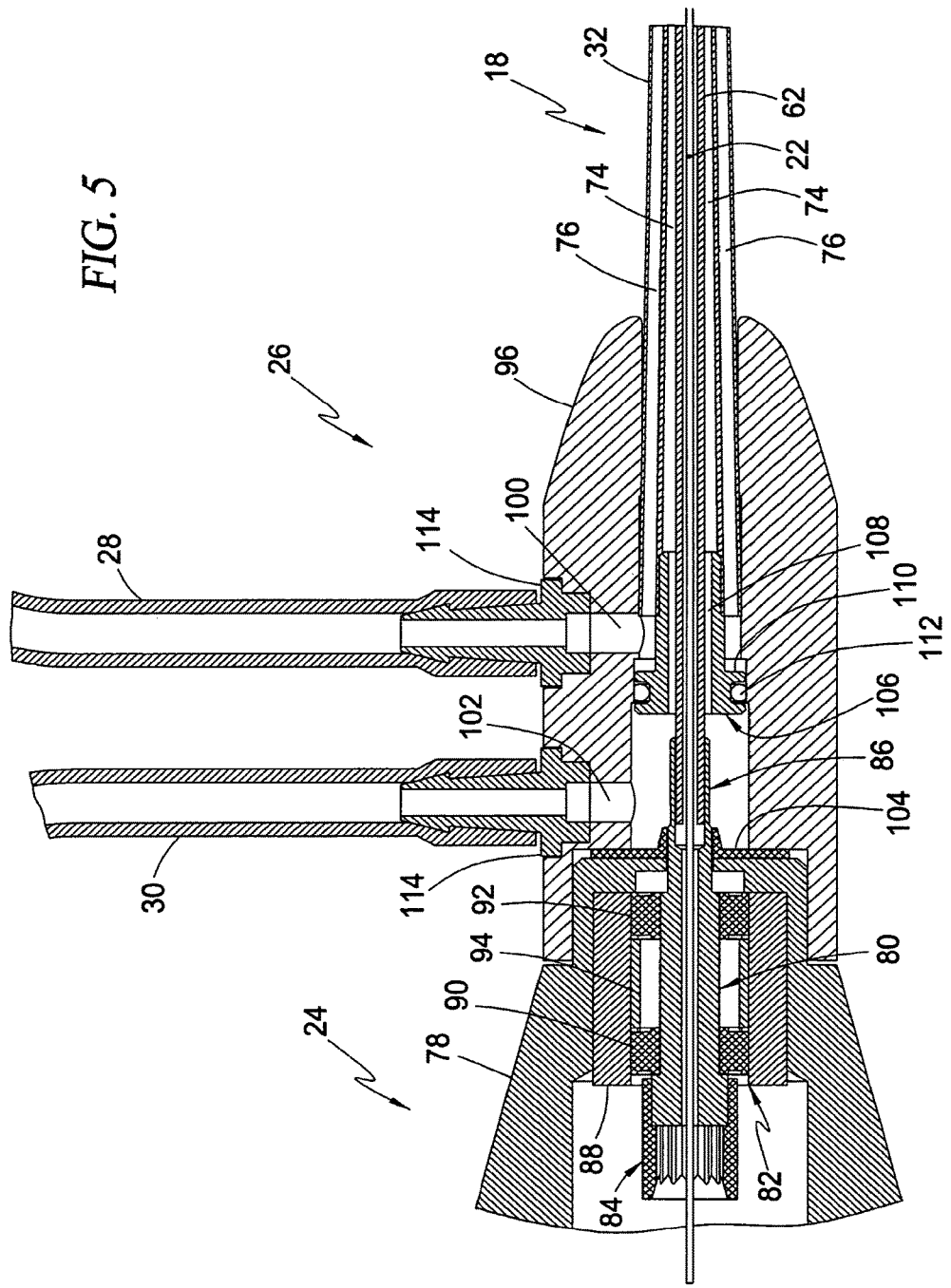
FIG. 5 is a cross-sectional view illustrating an exemplary construction of the motor coupler and purge fluid delivery system according to the first broad aspect of the present invention.

Referring to FIG. 5, the motor coupler 24 includes a housing 78, a drive shaft adapter 80, and a bearing assembly 82. The drive shaft adapter 80 includes a drive shaft coupler 84 dimensioned to receive a drive shaft of a motor (not shown), and a drive cable coupler 86 dimensioned to receive the drive cable 62. Any of a variety of attachment techniques may be employed to securely fasten the drive cable 62 to the drive cable coupler 86, including but not limited to adhesives, crimping, and laser welding. The drive shaft adapter 80 is rotatably disposed within the housing 78 by the bearing assembly 82. The bearing assembly 82 includes a sleeve 88 (which may alternatively be formed as an integral part of the housing 78) for retaining a pair of ball bearing assemblies 90, 92 and a spring 94 of the type described above. That is, each bearing assembly 90, 92 generally comprises an inner race which rotates along with the drive shaft adapter 80, an outer race which remains in a static and fixed position against the inner surface of the retaining sleeve 88, and a plurality of ball bearings disposed between the inner and outer races. The spring 94 is provided to bias each bearing assembly 90, 92 axially away from one another to reduce axial play during operation.

The purge fluid delivery system 26 includes a housing 96 having a central lumen 98, an inflow port 100, and an outflow port 102. The housing 96 is also dimensioned to matingly receive a portion of the motor coupler 24. In this regard, a seal element 104 is provided sandwiched in between the housing 96 and housing 78 and including an aperture which extends about the drive shaft adapter 80 as it exits the housing 78 to prevent the ingress of purge fluid into the motor coupler 24. A fluid guide structure 106 is also provided within the central lumen 98 for the purpose of separating the inflow and outflow ports 100, 102. The fluid guide structure 106 includes a central lumen 108 through which the drive cable 62 extends, and an elevated portion 110 that retains an O-ring 112 against the inner surface of the central lumen 98 of the housing 96. The drive cable sheath 32 is secured to the housing 96 such that the inflow port 100 is communicatively coupled to the side lumens 76, and the outflow port 102 is communicatively coupled to the central lumen 74. In this fashion, pressurized purge fluid may be introduced through the inflow port 100 via inflow conduit 28, and removed through the outflow port 102 via outflow conduit 30. By way of example, the inflow conduit 28 and outflow conduit 30 may be coupled to their respective ports 100, 102 via barbed connectors 114. Similarly, the inflow and outflow conduits 28, 30 may be equipped with any number of suitable connectors (such as those illustrated by way of example in FIG. 2) for establishing fluid communication with a source of pressurized fluid (not shown). The pressurized fluid source (not shown) may include, but is not necessarily limited to, the use of a syringe, an indeflator, a fluid delivery pump, or an accumulator arrangement to provide the requisite delivery of pressurized fluid. The purge fluid delivery system 26 thus provides a two-way transmission of purge fluid within the drive cable sheath 32 for the purposes of cooling the blood pump 12 and preventing the ingress of blood past the radial seal 64 and into blood pump 12.

Figure 6:
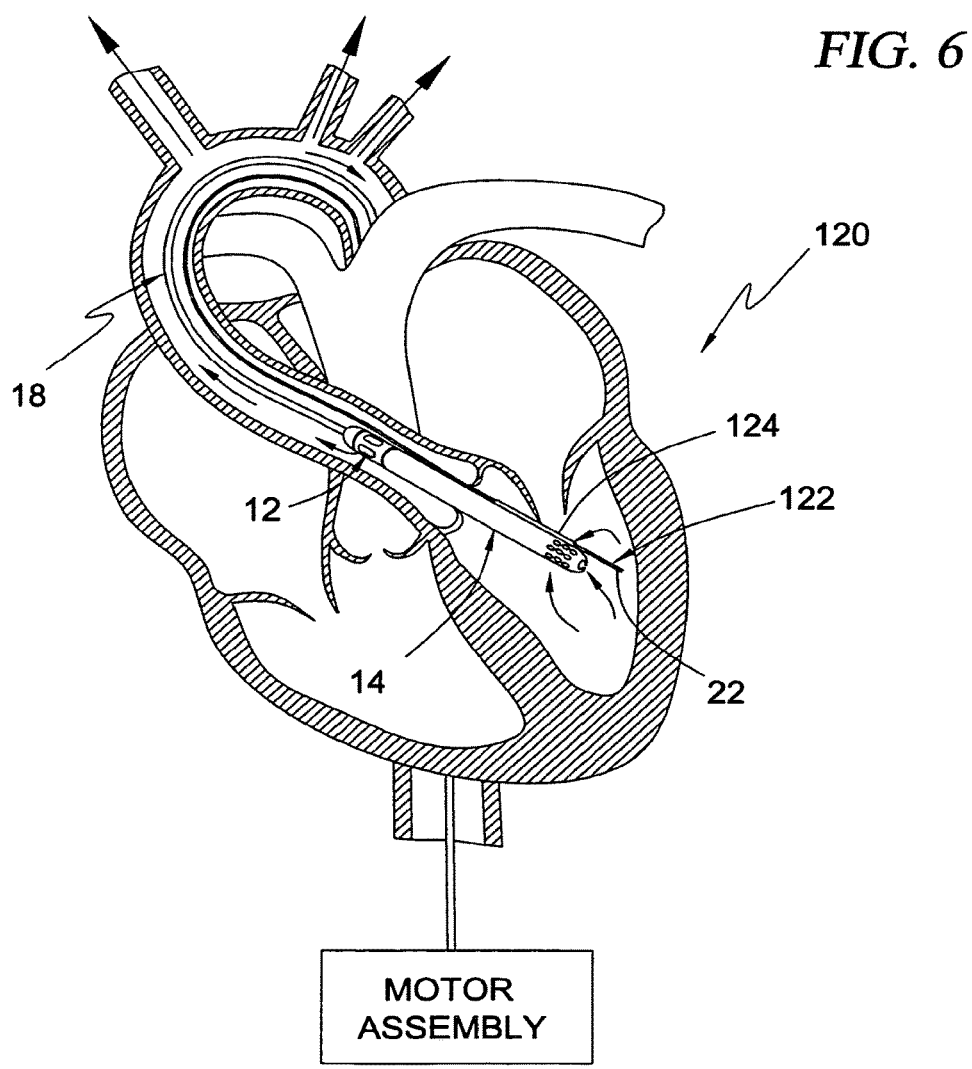
FIG. 6 is a partial sectional view of a human heart illustrating an intravascular blood pump system having a "rapid exchange" or "side-rigger" type guide mechanism according to a second broad aspect of the present invention positioned, by way of example, in a trans-valvular configuration to provide left-heart assist.

Referring to FIG. 6, shown is a guidable intra-vascular blood pump system 120 according to a second broad aspect of the present invention. As will be described hereinafter, the intravascular blood pump system 120 differs from the intravascular blood pump system 10 described above only as to the type of guide mechanism employed. In the interest of clarity and consistency, then, like reference numerals will be used to denote like elements and distinctions pointed out where necessary. Moreover, due to the commonality of principles employed in both intravascular blood pump systems 10, 120, a discussion to the level of detail set forth above is not deemed necessary with regard to the intravascular blood pump system 120. Instead, those aspects in common with the intravascular blood pump 10 are hereby incorporated into the discussion of the intravascular blood pump system 120.

In its most general form, the intravascular blood pump system 120 of this second broad aspect of the present invention comprises the blood pump 12 and cannula 14 arrangement, wherein the cannula 14 is equipped with a "side-rigger" or "rapid exchange" guide mechanism 122. In an important aspect of the present invention, the "rapid exchange" or "side-rigger" guide mechanism 122 includes a guide carriage 124 formed along at least a portion of the cannula 14, and a suitable guide element (such as guide wire 22) dimensioned to pass slidably through a lumen (not shown) extending through the guide carriage 124. The "rapid exchange" guide mechanism 122 thereby provides the ability to selectively guide the blood pump 12 and cannula 14 to a predetermined position in the circulatory system of a patient in the manner described above. Namely, the guide wire 22 may be first introduced into the vascular system of a patient through any suitable access point and guided to a desired location within the circulatory system of the patient, i.e. the left ventricle as shown. The blood pump 12 and cannula 14 may thereafter be advanced along the guide wire 22 and positioned in the trans-valvular configuration shown for providing left-heart assist.

Figure 9:
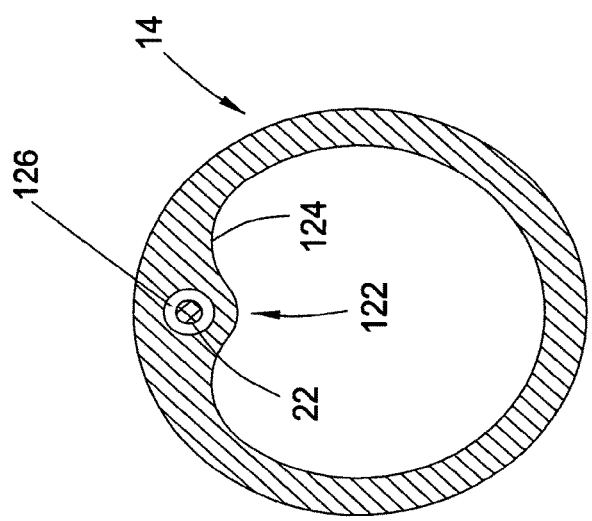
FIG. 9 is a cross-sectional view of the type shown in FIG. 8 illustrating an alternate configuration of the guide mechanism according to the second broad aspect of the present invention.
Figure 8:
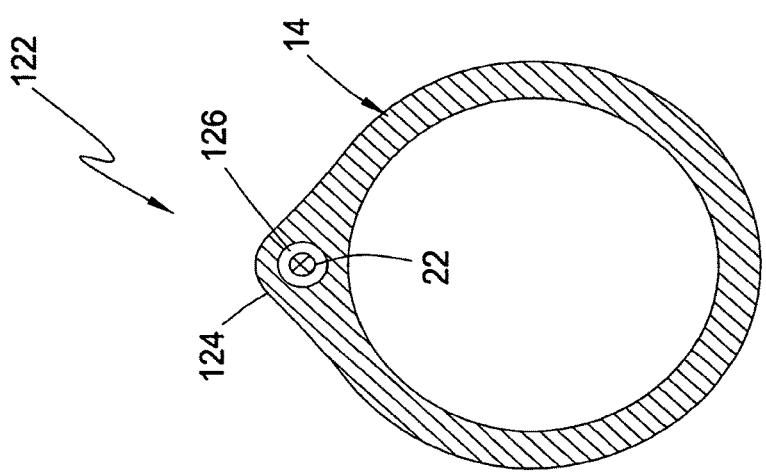
FIG. 8 is a cross-sectional view taken along lines 8-8 of FIG. 7 illustrating the "side-rigger" or "rapid exchange" type guide mechanism according to the second broad aspect of the present invention.

FIGS. 7-9 further illustrate the "side-rigger" or "rapid-exchange" guide mechanism 122 of this second broad aspect of the present invention. In a preferred embodiment, the "side-rigger" guide mechanism 122 includes a lumen 126 formed within the guide carriage 124. The guide carriage 124 is preferably formed as an integral extension of the wall of the cannula 14. FIGS. 7 and 8 comport with the embodiment shown in FIG. 6, namely illustrating the guide carriage 124 formed along the exterior surface of the cannula 14. FIG. 9 illustrates an alternate embodiment wherein the guide carriage 124 may be formed along the interior surface of the cannula 14. In either case, the guide wire 22 is advanced to a desired location in the vasculature of the patient, after which point the blood pump 12 and cannula 14 can be slidably advanced therealong for delivery to the desired location according to the present invention. The guide wire 22 may thereafter be withdrawn from the patient. If the guide carriage 124 is formed along the exterior surface of the cannula 14 (as shown in FIGS. 7-8), then the cannula 14 should preferably be positioned so that the guide carriage 124 does not extend in a trans-valvular fashion. For example, with reference to FIG. 6, the guide carriage 124 should be positioned wholly within the left ventricle such that the pulsatile blood flow during beating heart procedures will not inadvertently pass through the side lumen 126 and pass through the aortic valve.

The intravascular blood pump system 120 is constructed in virtually the same manner as the intravascular blood pump system 10 shown and described above, with the exception of the location of the respective guide mechanisms 16, 122. More specifically, because the guide mechanism 122 is disposed along the side of the cannula 14, there is no need to form a central lumen extending through the blood pump 12, drive cable assembly 18, purge fluid delivery system 26, and motor coupler 24 as detailed above with regard to the intravascular blood pump system 10. As such, these components need not be specially machined or molded to include such central lumens as was required with the intravascular blood pump system 10 set forth above.

Figure 10:
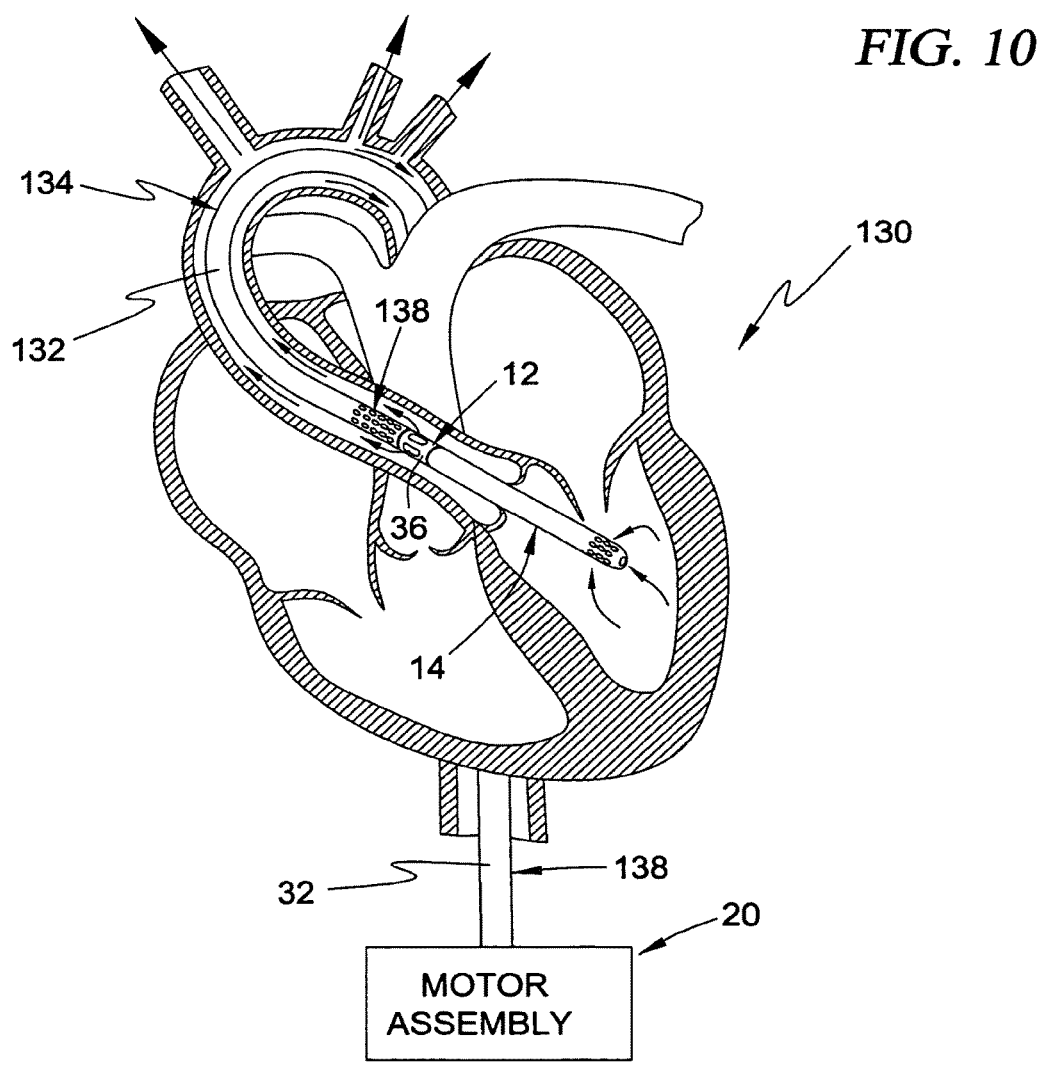
FIG. 10 is a partial sectional view of a human heart illustrating an intravascular blood pump system having a "guide catheter" type guide mechanism according to a third broad aspect of the present invention positioned, by way of example, in a trans-valvular configuration to provide left-heart assist.

Referring to FIG. 10, shown is a guidable intravascular blood pump system 130 according to a third broad aspect of the present invention. Again, due to the commonality between many of the same components and features of the intravascular blood pump systems described above and the intravascular blood pump system 130, like reference numerals will be used to denote like elements and distinctions pointed out where necessary. As will be explained in greater detail below, the intravascular blood pump system 130 employs yet another unique and useful guide mechanism according to the present invention. However, because many of the same components are employed, a discussion to the level of detail set forth above is not deemed necessary with regard to the intravascular blood pump system 130. Instead, those aspects in common with the intravascular blood pumps described above are hereby incorporated into the discussion of the intravascular blood pump system 130.

In its most general form, the intravascular blood pump system 130 of this third broad aspect of the present invention comprises the blood pump 12 and cannula 14 arrangement, wherein a "guide catheter" 132 is provided as the guide mechanism for positioning the pump 12 and cannula 14 at a desired location within the circulatory system of the patient. More specifically, with brief reference to FIG. 12, the intravascular blood pump system 130 is formed in two separate assemblies according to the present invention: a conduit assembly 134 and pump assembly 136. In its most basic form, the conduit assembly 134 comprises the guide catheter 132 and cannula 14 coupled to the rotor shroud 36. The pump assembly 136 is constructed such that the pump body 34 and rotor 44 can be disengaged from the rotor shroud 36 and removed entirely from the conduit assembly 134. Referring again to FIG. 10, this dual construction forms a significant feature of the present invention because it provides the ability to form the blood pump 12 at a desired location in a patient using two separate and distinct steps. The first step involves positioning the conduit assembly 134 (with the pump assembly 136 removed) within a patient such that the shroud 36 and cannula 14 are each disposed in a desired location, such as a trans-valvular configuration for cardiac assist procedures. In an important aspect, the task of positioning the conduit assembly 134 within the patient may be advantageously facilitated through the use of any number of well known guidance mechanisms, including but not limited to guide wires, balloon catheters, imaging wires, guide catheters, and/or techniques involving ultra-sound or fluoroscopy. The second step in providing the intravascular blood pump system 130 of the present invention involves advancing the pump assembly 136 through the conduit assembly 134 such that the rotor 44 docks within the shroud 36 to form the pump 12 at the desired location.

By way of clarification, the term "cannula" is used to denote cannula 14 because it serves a primary purpose of transporting fluid into the blood pump 12, whereas the term "catheter" is used to denote the catheter 132 because it serves a primary purpose of guiding or directing devices or components (i.e. the pump assembly 136) to a desired location within the body. It is to be readily understood, however, that these terms are only used for convenience and in a general fashion such that the cannula 14 may serve certain guiding functions and the catheter 132 may serve certain fluid transportation functions without departing from the scope of the present invention. For example, the cannula 14 may be equipped with dedicated lumens to receive various guide mechanisms (such as guide wires, balloon catheters, selectively deformable elements such as Nitonol, etc). In similar fashion, the guide catheter 132 may be used to transport fluid to and/or from the patient, such as by providing apertures 138 along predetermined regions of the catheter 132.

Figure 11:
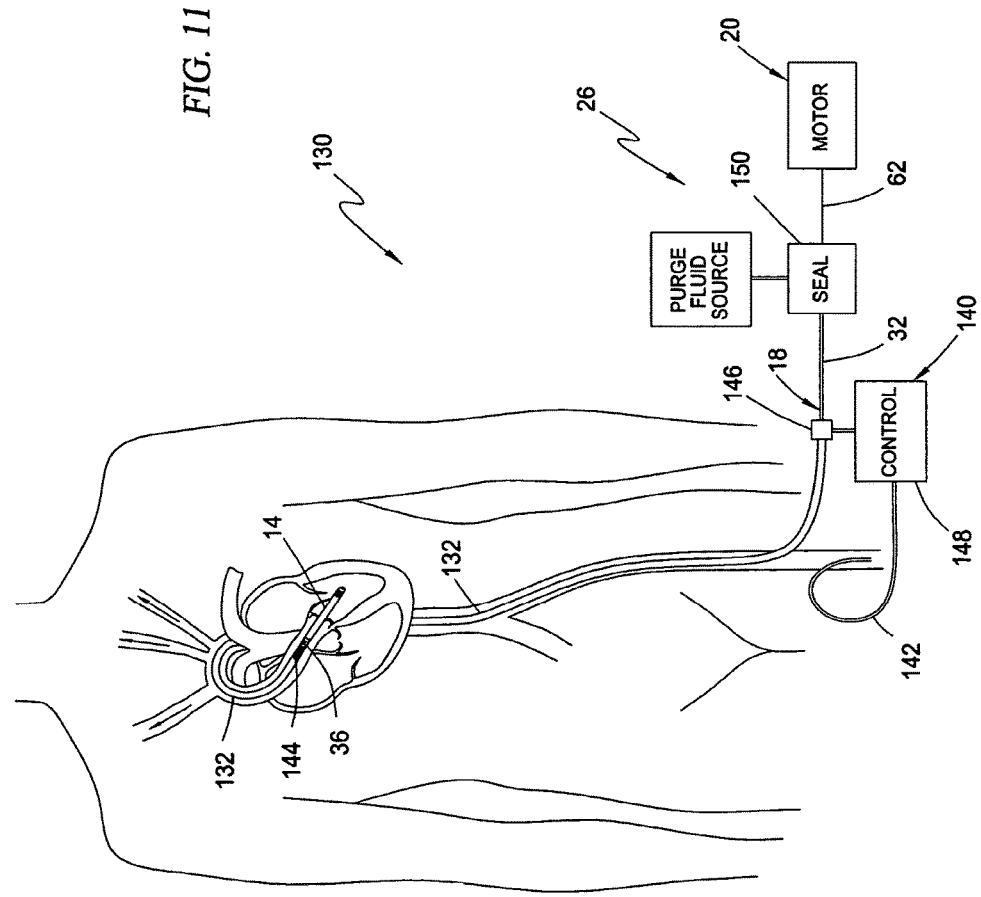
FIG. 11 is a schematic view of a human being illustrating the intravascular blood pump system of the type shown in FIG. 10 inserted through the femoral artery and including an optional perfusion assembly for perfusing the vasculature downstream from the incision site where guide catheter enters the femoral artery.

FIG. 11 demonstrates a significant feature of the present invention involving the use of the guide catheter 132 to transport fluid to and/or from the patient. An optional perfusion assembly 140 is provided as part of the intravascular blood pump system 130 of the present invention. The perfusion assembly 140 includes a conduit 142 in fluid communication with the apertures 138, which in this case are formed near the distal region of the guide catheter 132 a short distance downstream from the blood pump 12. In use, blood will pass along the exterior of the guide catheter 132 for distribution throughout the body, as well as within the interior of the guide catheter 132 after passing into the apertures 138. The perfusion assembly 140 may then be employed to selectively reroute blood from within the guide catheter 132 to a point within the patient's vasculature downstream from the point where the guide catheter 132 enters the body. A hemostasis valve assembly 146 of the perfusion assembly 140 permits the drive cable assembly 18 to pass through to the purge fluid delivery system 26 while preventing blood flow other than into the perfusion assembly 140. A seal assembly 150 of the purge fluid delivery system 26 permits the drive cable 62 to pass through to the motor 20 while preventing the flow of purge fluid other than into and from the purge fluid delivery system 26. The perfusion assembly 140 includes a control mechanism 148 for selectively controlling the distribution of perfusion blood flow from the perfusion assembly 140 into the patient. This control mechanism 148 may be automatic based on certain feedback criteria or manually operated.

Figure 12:
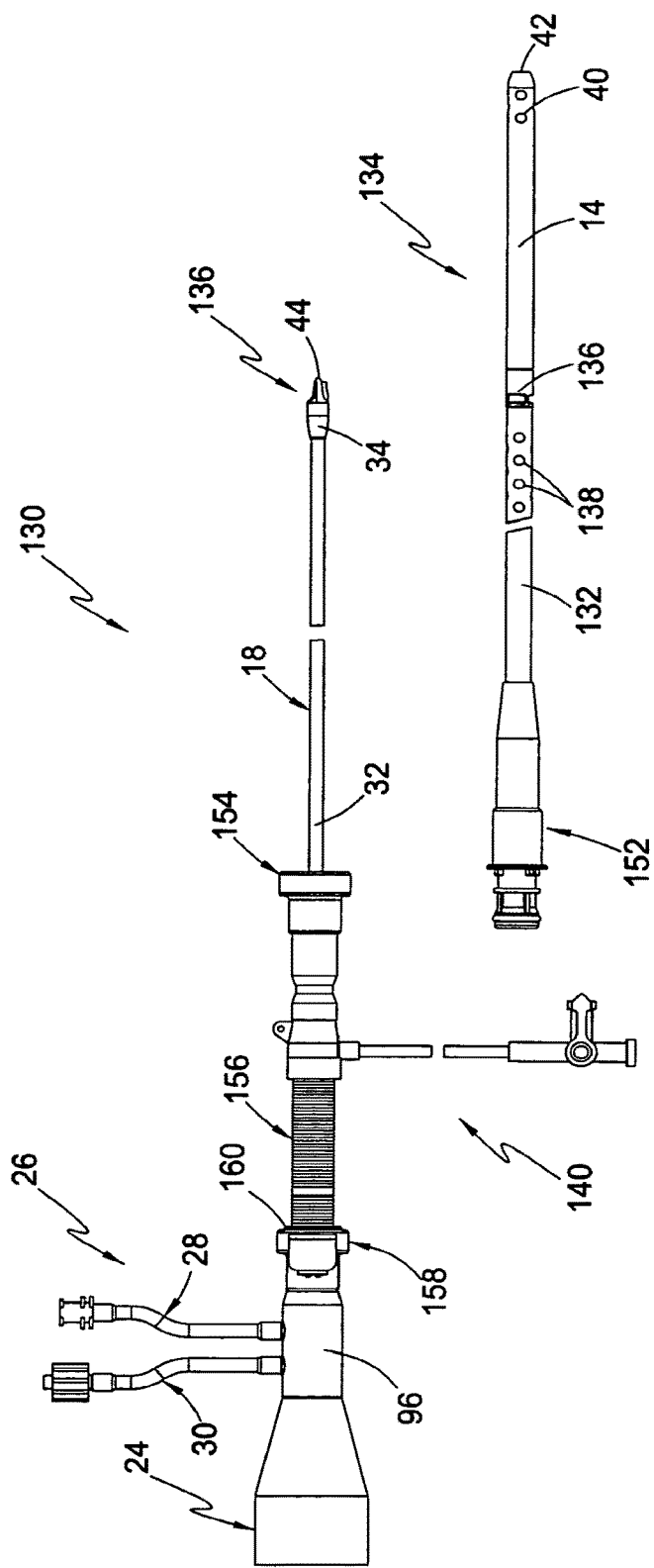
FIG. 12 is a side view of the intravascular blood pump system shown in FIGS. 10-11 illustrating the separable nature of a pump assembly and a conduit assembly which collectively form the intravascular blood pump system according to the third broad aspect of the present invention.

FIGS. 12-17 illustrate an exemplary construction of the intravascular blood pump system 130 according to the third broad aspect of the present invention. As shown in FIG. 12, the conduit assembly 134 may be selectively disengaged so as to remove the pump assembly 136 therefrom. According to the present invention, the conduit assembly 134 may be introduced (without the pump assembly 136) into the circulatory system of a patient and selectively guided such that the rotor shroud 36 and cannula 14 are positioned at a desired location. The pump assembly 136 can thereafter be selectively introduced into the conduit assembly 134. A challenge in such a "back-loading" arrangement is ensuring that the pump assembly 136 docks appropriately within the rotor shroud 36 and is maintained in proper engagement during operation of the resulting pump 12.

Figure 14:
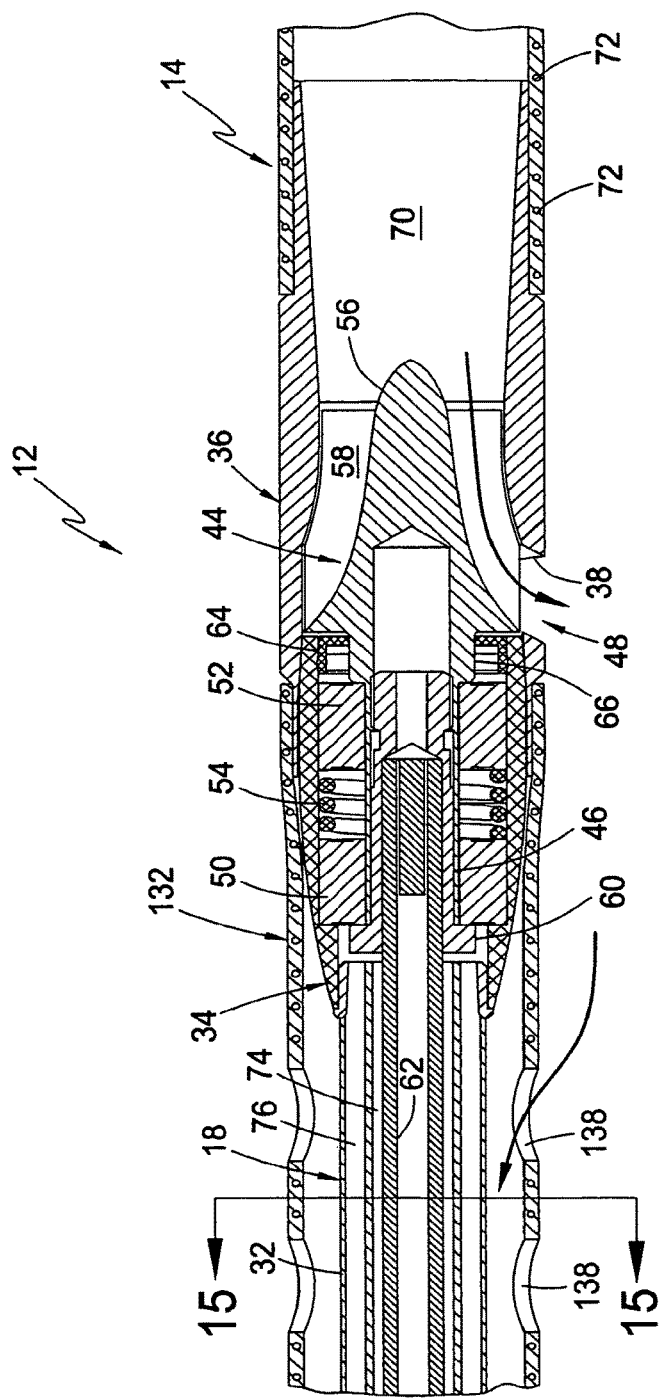
FIG. 14 is a cross-sectional view illustrating an exemplary construction of the blood pump, drive cable assembly, cannula, and guide catheter of the intravascular blood pump system shown in FIG. 13.
Figure 15:
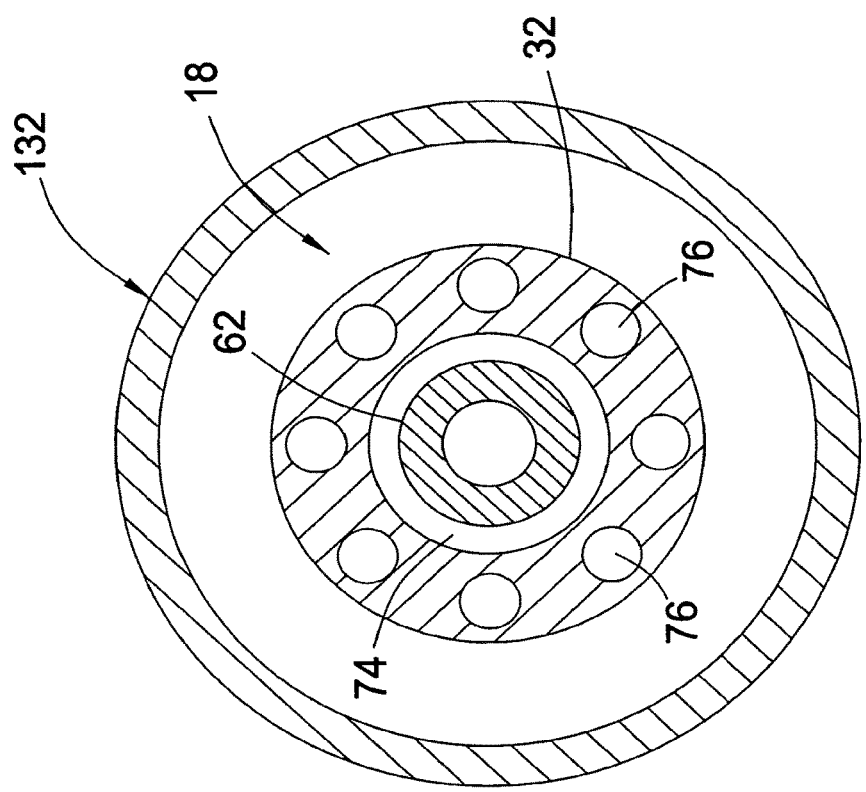
FIG. 15 is a cross-sectional view taken along lines 15-15 of FIG. 14 illustrating an exemplary construction of the drive cable assembly and guide catheter according to the third broad aspect of the present invention.
Figure 16:
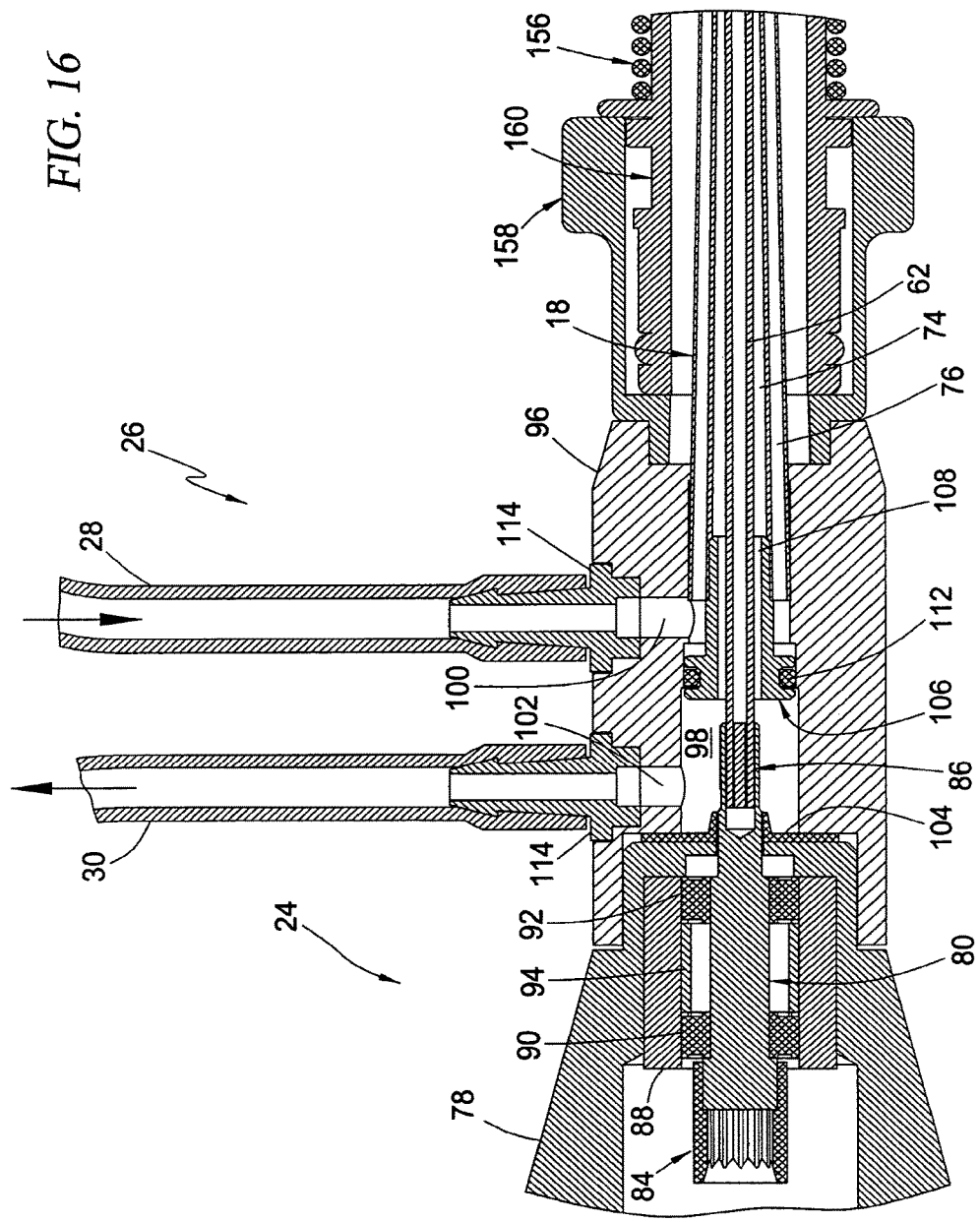
FIG. 16 is a cross-sectional view illustrating an exemplary construction of the motor coupler, purge fluid delivery system, and a proximal portion of the guide catheter biasing assembly according to the third broad aspect of the present invention.

An exemplary docking arrangement will now be described with reference to FIG. 14. In a preferred embodiment, the rotor 44 may be properly and accurately docked within the shroud 36 by forming angled mating surfaces on corresponding portions of the shroud 36 and pump body 34. More specifically, an angled mating surface may be formed on the interior surface of the rotor shroud 36 along that portion extending proximally from the flow aperture 38. A corresponding angled mating surface may be provided along the exterior surface of the pump body 34 along a distal portion thereof. The mating surfaces shown in FIG. 14 may preferably be formed in the range from about 2 degrees to 10 degrees, and more preferably formed in the range from about 3 degrees to 6 degrees. Mating angles within these ranges are adequate to guide the distal end of the pump body 34 to a point generally flush with the proximal edge of the flow aperture 38 as shown in FIG. 14. In this fashion, the pump assembly 136 and the rotor shroud 36 combine to form the blood pump 12. More importantly, this docking is carried out such that the rotor 44 and rotor blades 58 are maintained in proper position for efficient and safe pump operation.

An exemplary biasing scheme for maintaining the pump assembly 136 in this docked relationship will now be described with reference to FIGS. 12-13 and 16-17. The conduit assembly 134 is preferably equipped with a male quick-connect coupling 152 capable of engaging with a female quick-connect coupling 154 forming part of the perfusion assembly 140 of the present invention. A bias spring 156 is provided in between the perfusion assembly 140 and the housing 96 of the purge fluid delivery system 26. The bias spring 156 is preferably dimensioned so as to be in tension when the male quick-connect 152 is engaged within the female quick-connect 154 as part of the docking process of the present invention. As such, the bias spring 156 serves to maintain the pump assembly 136 in the docked position within the rotor shroud 36. The bias spring 156 may be coupled to the housing 96 of the purge fluid delivery system 26 in any number of suitable fashions. One such coupling arrangement may comprise a female quick-connect coupling 158 attached to the housing 96 and a male quick-connect coupling 160 attached to the bias spring 156.

Figure 13:
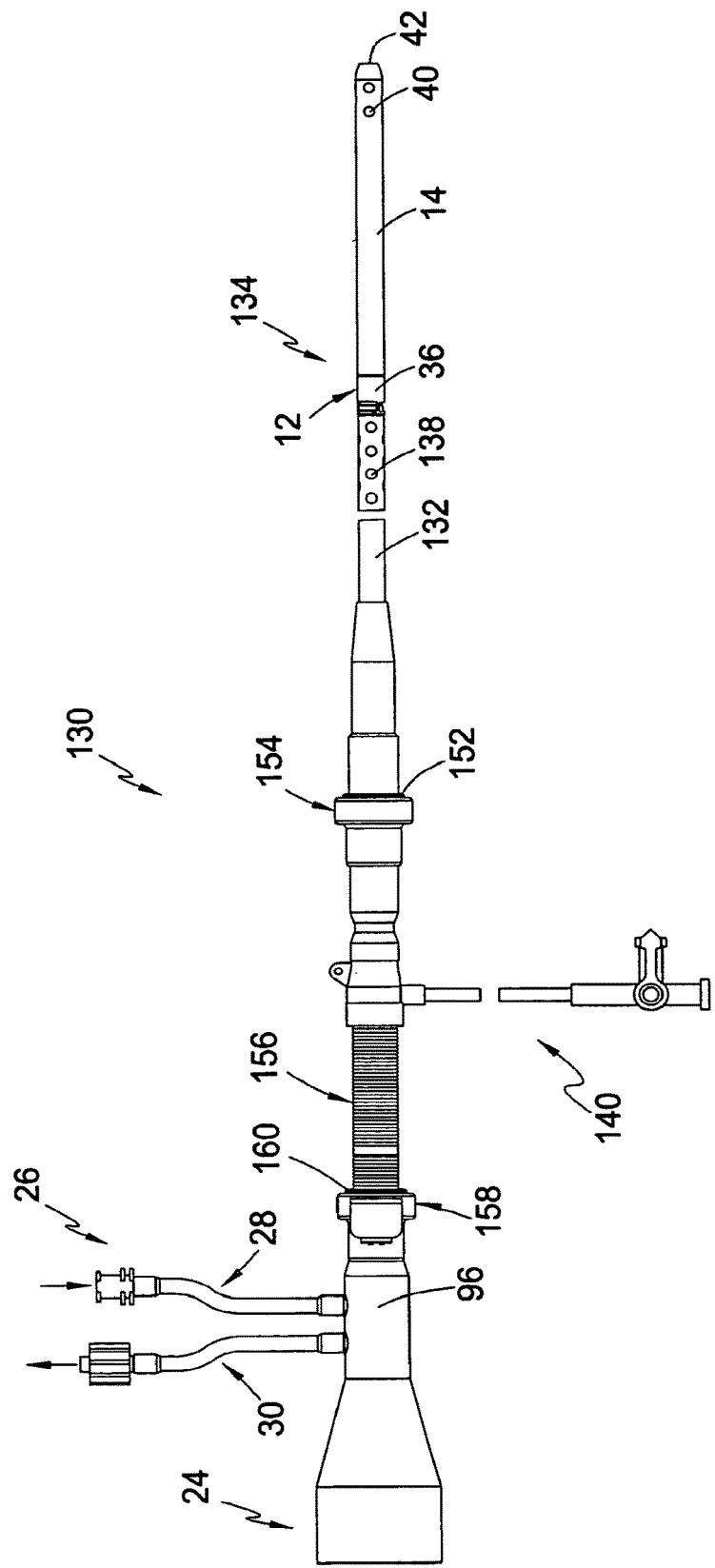
FIG. 13 is a side view illustrating the intravascular blood pump system shown in FIG. 12 with the pump assembly docked into the conduit assembly according to the third broad aspect of the present invention.
Figure 17:
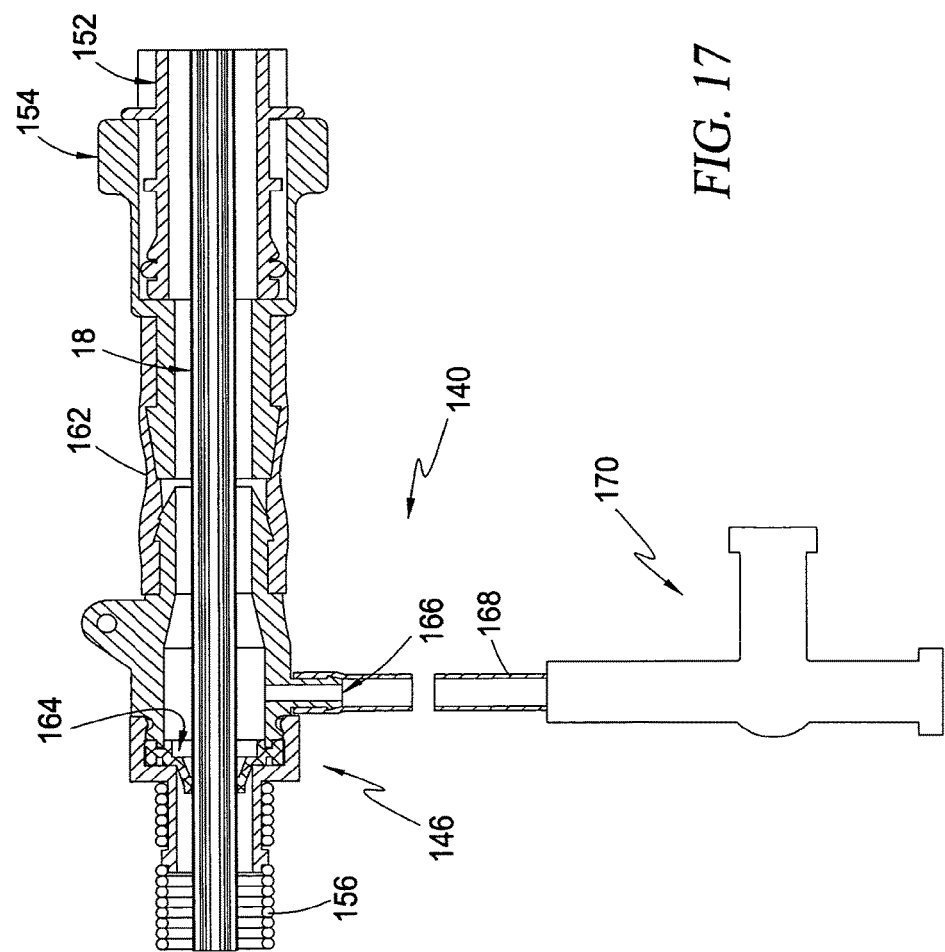
FIG. 17 is a cross-sectional view illustrating an exemplary construction of the perfusion assembly and a distal portion of the guide catheter biasing assembly according to the third broad aspect of the present invention.

An exemplary embodiment of the perfusion assembly 140 is shown with reference to FIGS. 12-13 and 17. The perfusion assembly 140 shown includes the hemostasis valve 146 coupled to the female quick-connect coupling 154. A length of tubing 162 extends between the opposing barb connectors of the hemostasis valve 146 and the female quick-connect coupling 154. A continuous lumen is formed extending through the interior of the male quick-connect coupling 152, the female-quick-connect coupling 154, the tubing 162, and the hemostasis valve 146. The drive cable assembly 18 extends through this continuous lumen and exits through a Touehy-Borst hemostasis seal 164 which prevents the migration of blood out of the proximal end of the perfusion assembly 140. A side-port 166 is disposed in fluid communication with the central lumen of the perfusion assembly 140. In one embodiment, this side-port 166 may be equipped with a conduit 168 having a stop-cock 170 to selectively control the distribution of blood through a perfusion conduit (i.e. conduit 142 of FIG. 11) coupled to the stop-cock 170. It will be appreciated that this type of manual control system for selectively perfusing the patient may be replaced with control circuitry for automatically controlling the rate of perfusion. Such automatic perfusion may be based on control algorithms based on contemporaneous feedback or pre-programmed thresholds.

The foregoing discussion details a host of inventive aspects forming part of the present invention. It will be appreciated by those skilled in the art that changes could be made to the embodiments described above without departing from the broad inventive concepts thereof. The following evidences, by way of example only, various additional aspects forming part of the present invention.

Figure 18:
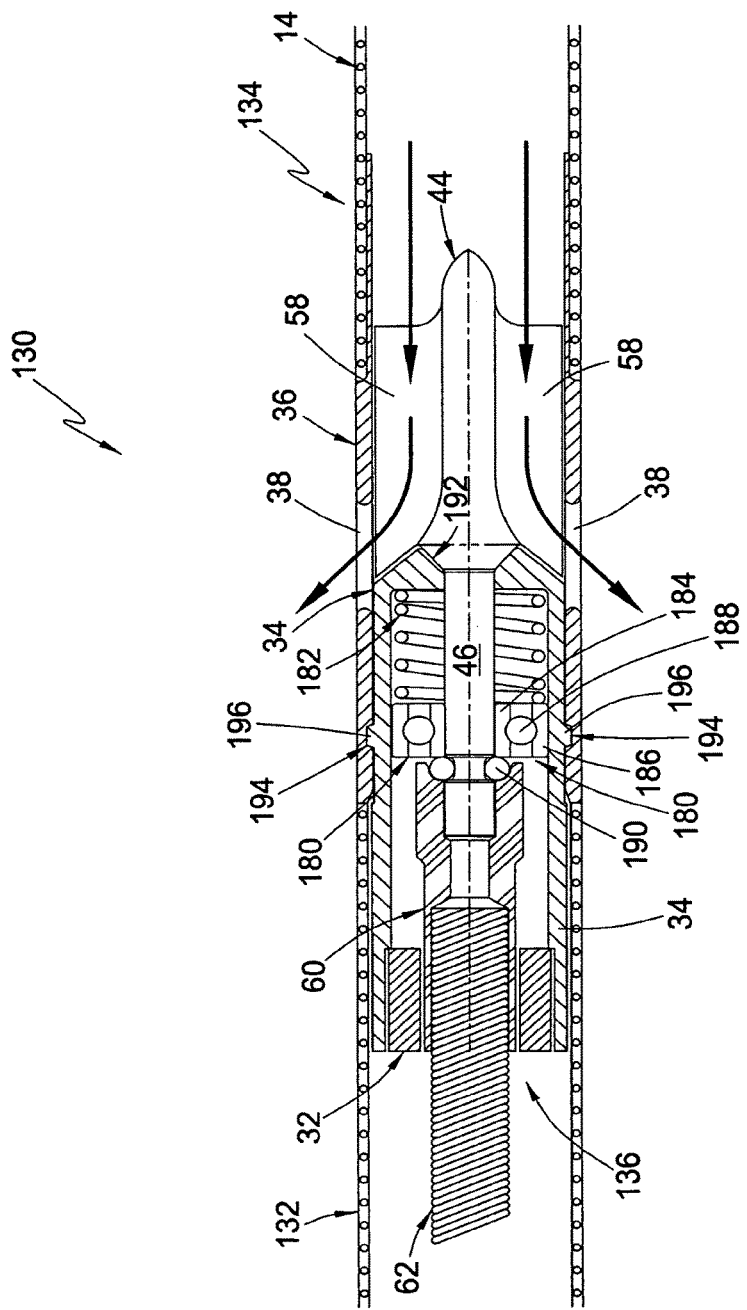
FIG. 18 is a cross-sectional view of an intravascular blood pump system of the type shown in FIGS. 12-13 having an alternate configuration for docking the rotor within the shroud according to the principles of the present invention.

FIG. 18 illustrates an alternate configuration of the intravascular blood pump system 130 of the third broad aspect of the present invention having an alternate bearing assembly, purge fluid delivery, and docking scheme. The bearing assembly includes a seal spring 182 and a bearing assembly 180. The bearing assembly 180 includes an inner race 184, an outer race 186, and a plurality of balls 188 which enable the inner race 184 to rotate along with the rotor shaft 46 while the outer race 186 remains in a static and fixed position relative to an inner surface of the pump body 34. An O-ring 190 is disposed within a groove formed in the rotor shaft 46 so as to maintain the bearing assembly 180 against the seal spring 182. The O-ring 190 is further secured within the groove in the rotor shaft 46 via a contoured lip portion extending from the distal end of the cable adapter 60. The proximal end of the cable adapter 60 flushly engages the drive cable 62.

The purge fluid delivery system of the embodiment shown in FIG. 18 provides for a one way delivery of purge fluid to the blood pump 12. That is, pressurized fluid (namely, fluid pressurized to some level elevated above the blood pressure in the surrounding vessel) is injected in between the drive cable 62 and the interior of the protective sheath 32 during operation. This serves to reduce any frictional heating that exists between the drive cable 62 and sheath 32. The pressurized fluid also flows through the interior of the pump 12 such that, if the seal at 192 is broken, the pressurized fluid will flow past the open seal 192 and onward through the blood flow ports 38 formed in the shroud 36. This serves to keep blood from entering the pump 12 in an effort to avoid clotting and/or damaging the pump 12.

The pump assembly 136 may be docked within the conduit assembly 134 in any number of different fashions without departing from the scope of the present invention. That is to say, the docking scheme shown in FIG. 18 is set forth by way of example only and is not to be deemed limiting or restrictive as to numerous ways to temporarily engage or "dock" the pump assembly 136 within the conduit assembly 134. The only requirement is that the pump assembly 136 and conduit assembly 134 dock such that the rotor 44 is disposed within the shroud 36 to provide the desired axial flow through the cannula 14 and out the shroud 36. The exemplary docking scheme involves forming an annular engagement groove 194 along the interior of the shroud 36, and forming a complementary annular ridge 196 along the exterior surface of the pump body 34. During insertion, the pump assembly 136 will be advanced into the conduit assembly 134 until the annular ridge 196 on the pump body 34 engages within the groove 194 formed in the shroud 36. This docking scheme is generally advantageous in that the engagement action between the annular ridge 196 and groove 194 will provide tactile feedback to the physician during the process of inserting the pump assembly 136 into the conduit assembly 134 such that the physician will be able to determine when the docking has been completed.

As will be appreciated by those skilled in the art, the location of the annular ridge 196 and engagement groove 194 may be varied such that they are disposed closer or farther away from the flow apertures 38. It may be advantageous to form these docking structures close to the flow apertures 38 in an effort to thwart the ingress of blood into the junction extending between the interior of the shroud 36 and the exterior surface of the pump body 34. It is also contemplated to employ selectively inflatable structures, such as balloons, in an effort to temporarily engage or dock the pump assembly 136 within the conduit assembly 134. In this regard, one or more lumens may be formed within the pump body 34 extending from the interior of the pump body 34 in fluid communication with a balloon disposed along the exterior surface of the pump body 34. The pressurized fluid flowing within the interior of the pump body 34 may then be used to inflate the balloon, which will then engage within an annular groove in the shroud 36, such as at 194. Of course, the engagement structures may also be reversed without departing from the scope of the present invention. For example, the shroud 36 may be equipped with a fluid delivery lumen therein for inflating a balloon disposed on the interior surface of the shroud 36, which may in turn be disposed within an annular engagement groove formed along the exterior surface of the pump body 34.

Figure 19:
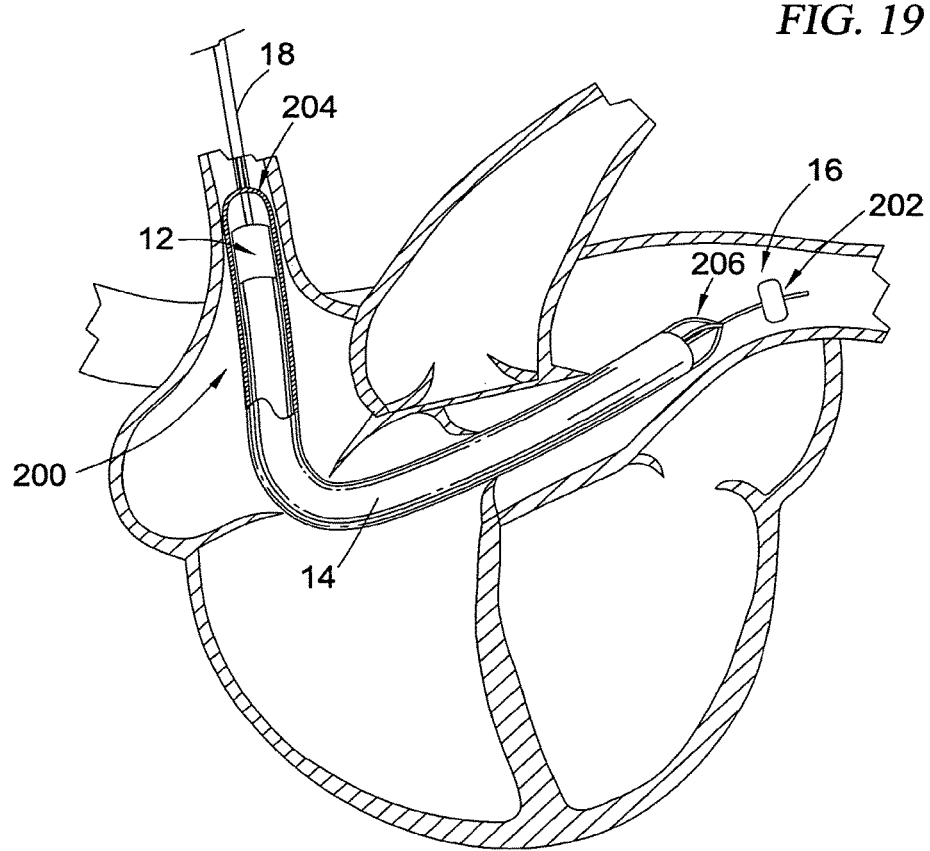
FIG. 19 is a partial sectional view of a human heart illustrating an alternate intravascular blood pump system having an "over-the-wire" type guide mechanism according to the first broad aspect of the present invention positioned, by way of example, in a trans-valvular configuration to provide right-heart assist.

While this invention has been shown in use largely in during left-heart applications it is to be readily appreciated that this does not limit the applications of this invention for use in left heart support only. Rather, the guidable intravascular blood pump of the present invention can be utilized in right-heart support applications and a wide variety of other applications apparent to those skilled in the art. For example, with reference to FIG. 19, shown is an intravascular blood pump 200 (of the type shown and described above with reference to FIGS. 2-5) configured for use in a right-heart support application. In this embodiment, the intravascular blood pump system 200 is equipped, by way of example, with an "over-the-wire" guide mechanism 16 comprising a balloon catheter 202. It is to be readily appreciated that, although shown and described below in terms of an embodiment of the type shown in FIGS. 2-5, the intravascular blood pump systems 120, 130 disclosed herein may also be configured for use in right-heart applications. Such right-heart configurations, and others apparent to those skilled in the art based on the broad principles enumerated in this application, are contemplated as being within the scope of the present invention.

The intravascular blood pump system 200 is shown positioned within the heart, such as may be advantageous to provide right heart support during beating heart surgery. To position the guidable intravascular blood pump system 200 in the right heart according to the present invention, a suitable guide element (such as balloon catheter 202) is first advanced to a desired location within the heart via the "sail" action of an inflated balloon. After the balloon catheter 202 is located in the desired position (such as in the pulmonary artery as shown), the intravascular blood pump system 200 according to the present invention may be advanced over the balloon catheter 202 and guided into a desired arrangement. For right heart support, this would involve advanced into the pump 12 and cannula 14 overt the balloon catheter 202 until the fluid inlet 204 is disposed within the vena cava (or right atrium) and the fluid outlet 206 is positioned within the pulmonary artery. The pump 12 may then be selectively (i.e. automatically or on-demand) controlled to transport blood from the vena cava (or right atrium) in a trans-valvular fashion through the tricuspid valve, the right ventricle, and the pulmonary valve for deposit within the pulmonary artery. Providing right-heart support during beating heart surgery advantageously overcomes conditions where cardiac output may become compromised during beating heart surgery, such as when the heart is lifted to gain access to posterior vessels, thereby avoiding the need for cardiopulmonary bypass.

It is also contemplated as part of the present invention that the guidable intravascular blood pump systems can be introduced into the patient's vasculature to achieve the intravascular access into the right or left heart through any number of access points, including but not limited to the internal jugular vein, the brachiocephalic vein, carotid artery, axillary artery, femoral vein, femoral artery, and subclavian artery. The intravascular blood pump systems of the present invention may also be introduced via direct introduction, such as into the aorta, the atria, and the ventricles. As is well known in the art, such intravascular access may be achieved percutaneously through the use of the Seldinger technique or directly through the use of minimally invasive access techniques.

Those skilled in the art will also appreciate that, although shown and described above in terms of "axial flow," the present invention is not limited to the axial flow type intravascular blood pumps. Rather, the intravascular blood pumps 12 may comprise any number of suitable types of intravascular blood pumps, including but not limited to so-called "mixed flow" intravascular blood pumps, without departing from the scope of the present invention.

With regard to the embodiments shown in FIGS. 10-17, it is furthermore contemplated that the guide catheter 132 may be separable from the conduit assembly 134 after the pump assembly 136 is docked within the shroud 36 to form the pump 12 at the desired location within the circulatory system of the patient. This may be accomplished by providing the guide catheter 132 in a detachable fashion via any number of suitable arrangements. By removing the guide catheter 132 after the pump 12 assembled, wound management of the access point into the patient's vasculature may be improved. This is due, in part, to the substantial reduction in size of the device extending into the patient (i.e. the drive cable assembly 18 as opposed to the larger diameter guide catheter 132).

It is also contemplated to incorporate various pressure sensing and/or guidability features into at least one of the cannula, 14 and pump 12. Such features may include, but are not necessarily limited to, those shown and described in commonly-owned and co-pending U.S. patent application Ser. No. 09/280,988 (filed Mar. 30, 1999) entitled "Steerable Cannula," and U.S. patent application Ser. No. 09/280,970 (filed Mar. 30, 1999) entitled "Pressure Sensing Cannula," the disclosures of which are hereby expressly incorporated by reference as if set forth herein in their entirety and physically incorporated as APPENDIX A and APPENDIX B respectively to the present specification. These pressure sensing features may include, but are not necessarily limited to, the use of fluid-filled lumens, piezo-electric pressure sensing elements, strain gauges, and analysis of the torque/current relationship (based on the dynamic pressure differential between the inlet and outlet of the pump). The guidability features may include, but are not necessarily limited to, the use of side lumens and deformable materials (i.e. Nitonol).

Various pump and cannula arrangements have been described and shown above for providing right and/or left heart support wherein blood is deliberately re-routed through and past the right and/or left ventricle in an effort to reduce the volume of blood to be pumped by the particular ventricle. While "unloading" the ventricles in this fashion is preferred in certain instances, it is to be readily understood that the pump and cannula arrangements described herein may also be employed to "preload" the ventricles. Ventricular preloading may be accomplished by positioning the outflow cannula from the pump into a given ventricle such that the pump may be employed to fill or preload the ventricle with blood. This may be particularly useful with the right ventricle. On occasion, the right ventricle is not supplied with sufficient levels of blood from the right atrium such that, upon contraction, the right ventricle delivers an insufficient quantity of blood to the pulmonary artery. This may result when the right ventricle and/or right atrium are in a stressed or distorted condition during surgery. Preloading overcomes this problem by actively supplying blood into the right ventricle, thereby facilitating the delivery of blood into the pulmonary artery. The same technique can be used to preload the left ventricle and thus facilitate the delivery of blood from the left ventricle into the aorta.

APPENDIX A—(U.S. SER. NO. 09/280,988)

Steerable Cannula

BACKGROUND OF THE INVENTION

1. Field of the Invention

The invention relates to vascular cannulas for use in medical procedures.

2. Description of Related Art

In medical applications and specifically in surgery, the list of uses for cannulas is exhaustive. Cannulas are to be distinguished from catheters in that catheters generally have a substantially smaller fluid-carrying capacity are used primarily for sampling or measurement purposes or for delivery of small quantities of fluid, whereas cannulas are generally larger and are used for volumetric fluid transfer. One application of cannulas involves the augmenting or supplementing of pulmonary blood flow through the beating heart during cardiac-surgery by use of one or more cannulas involved in the intake and return of blood into the circulatory system. The cannulas interface between the patient's circulatory system and the mechanical pumps that power the augmentation procedure. Such an application is described in co-pending PCT Application no. PCT/US97/18674 entitled "Single Port Cardiac Support Apparatus", filed Oct. 14, 1997 and incorporated herein by reference in its entirety.

As will be appreciated, precise and quick placement of the cannula in surgical applications is critical, given the severe time constraints facing a surgeon whose patient's vital life sustaining functions have been suspended during the procedure. Currently, methods for placing cannulas in a patient's body are crude, in that they rely on guesswork and trial and error. Specifically, a surgeon will insert the cannula and direct it towards the desired destination, but ultimately must feel by hand, through the patient's tissue for example, whether it has reached that destination. The surgeon may be forced to make several retractions and re-insertions until the process succeeds. Shortcomings of such a procedure are clear and may include damage to the delicate tissue involved and waste of valuable time. Additionally, constraints on the flexibility of the material are imposed since a prescribed amount of rigidity is required to enable the cannula to be felt through the tissue and insure that the cannula does not collapse under insertion force.

Alternatively, the surgeon may rely on the use of guiding devices such as a guide wire threaded through the cannula. The guide wire is often easier to manipulate than the cannula, and its placement precedes placement of the cannula. After the guide wire is in place, the cannula is pushed along the length of the guide wire, following the guide wire to the desired destination.

It is also known that a flow directed balloon catheter can be used as a guide wire. Balloon catheters are well known in the art and have a multitude of uses, including delivery or removal of fluid from the surgical site. However, flow directed balloon catheters are typically at least an order of magnitude smaller than cannulas. Their small size accordingly severely limits their application since both quantity and rate of fluid flow through the catheter are limited. In fact it is precisely because of their small size that flow directed balloon catheters can be used as guiding devices for the larger, more robust and versatile cannulas. During use as a guiding device for a cannula, the flow directed balloon catheter acts as a guide wire in facilitating the advancement of the cannula to the desired destination. The flow directed balloon catheter is first inserted into place in the patient's body, and the cannula, threaded around the flow directed balloon catheter, is then advanced into the desired position.

Insertion of the flow directed balloon catheter is effected using the inflatable balloon disposed at a distal tip of the flow directed balloon catheter. A lumen in communication with the balloon delivers inflating fluid to the balloon, thereby inflating the balloon and causing it to operate as a "sail" which is pulled along in the blood stream through the natural blood flow in the patient's circulatory system.

The above procedures have met with only limited success, and there exists a long felt need for devices and methods that facilitate placement of a cannula in a patient's body. A system that will assist in the manipulation of the cannula through the vascular structure or other bodily regions of the patient would accordingly serve to make the placement process more efficient and less time-consuming, improving the chance of overall success of a surgical procedure.

BRIEF SUMMARY OF THE INVENTION

The present invention overcomes the deficiencies of the prior art by providing a cannula which can be steered during its advancement in the body of the patient. Steering is implemented using cables connected to a deformable portion of the cannula. The cables extend to the proximal end of the cannula from where the operator can selectively apply tensional forces to thereby cause the cannula to curve at the deformable portion. The deformable portion is disposed preferable at the distal end of the cannula, but may be located at other sites along the length of the cannula.

In accordance with a second embodiment of the invention, the cannula is provided with more than one cable for facilitating deformation along multiple planes. Additionally, preformed curves may be provided along the length of the cannula, which curves can be either augmented or straightened by applied tension to the cables.

The cannula, in accordance with a third embodiment, is provided with a spiraling wire formed in the cannula wall. The spiraling wire operates to provide rigidity to the body of the cannula and maintain good fluid flow therein. The spiraling wire may comprise a portion of the cable used to impart deformation in an arrangement in accordance with a fourth embodiment of the invention.

In accordance with a fifth embodiment of the invention, the steerable cannula is provided with an inflatable balloon at the distal end thereof for assisting in guiding the cannula to its desired destination. The inflatable balloon is selectively inflatable using a lumen which effects fluid communication between an fluid source and the balloon.

In accordance with a fifth embodiment of the invention, the steerable cannula is provided with an inflatable balloon at the distal end thereof for assisting in guiding the cannula to its desired destination. The inflatable balloon is selectively inflatable using a lumen which effects fluid communication between an fluid source and the balloon.

In accordance with a sixth embodiment of the invention, a steerable cannula having a pigtail distal tip configuration is provided.

In accordance with a seventh embodiment of the invention, a steerable cannula having a movably supported guide wire is provided.

In accordance with an eighth embodiment of the invention, a steerable cannula having an integrally formed guide wire is provided.

In accordance with a ninth embodiment of the invention, a steerable cannula is used in a co-axial cannula arrangement.

BRIEF DESCRIPTION OF THE SEVERAL VIEWS OF THE DRAWING(S)

Figure 21:
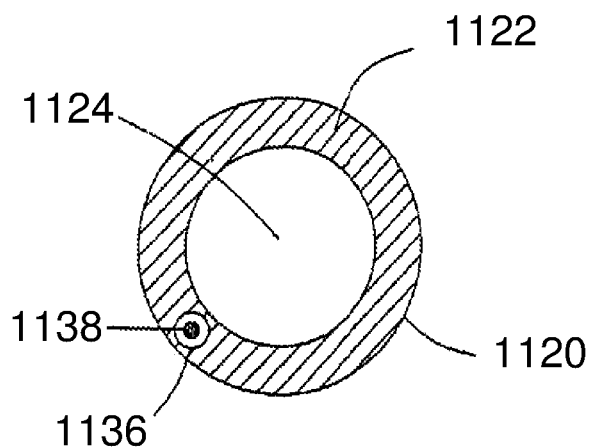
FIG. 21 corresponds to FIG. 2 of U.S. Ser. No. 09/280,988, and is a schematic cross-sectional view of the steerable cannula of FIG. 20 taken along line A-A.
Figure 23:
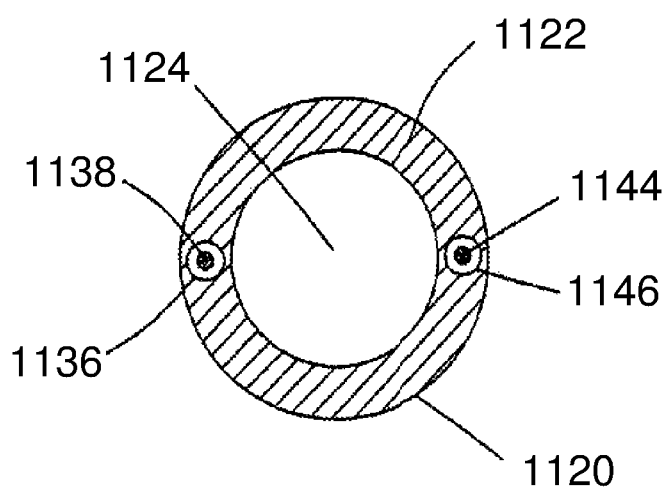
FIG. 23 corresponds to FIG. 4 of U.S. Ser. No. 09/280,988, and is a schematic cross-sectional view of a steerable cannula having two cables in accordance with a second embodiment of U.S. Ser. No. 09/280,988.
Figure 24:
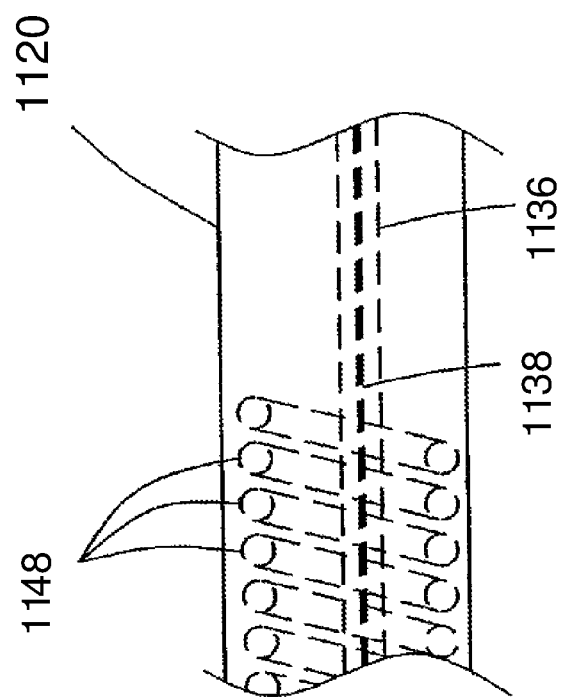
FIG. 24 corresponds to FIG. 5 of U.S. Ser. No. 09/280,988, and is a schematic side view of a steerable cannula having a reinforcing wire in accordance with a third embodiment of U.S. Ser. No. 09/280,988.
Figure 27:
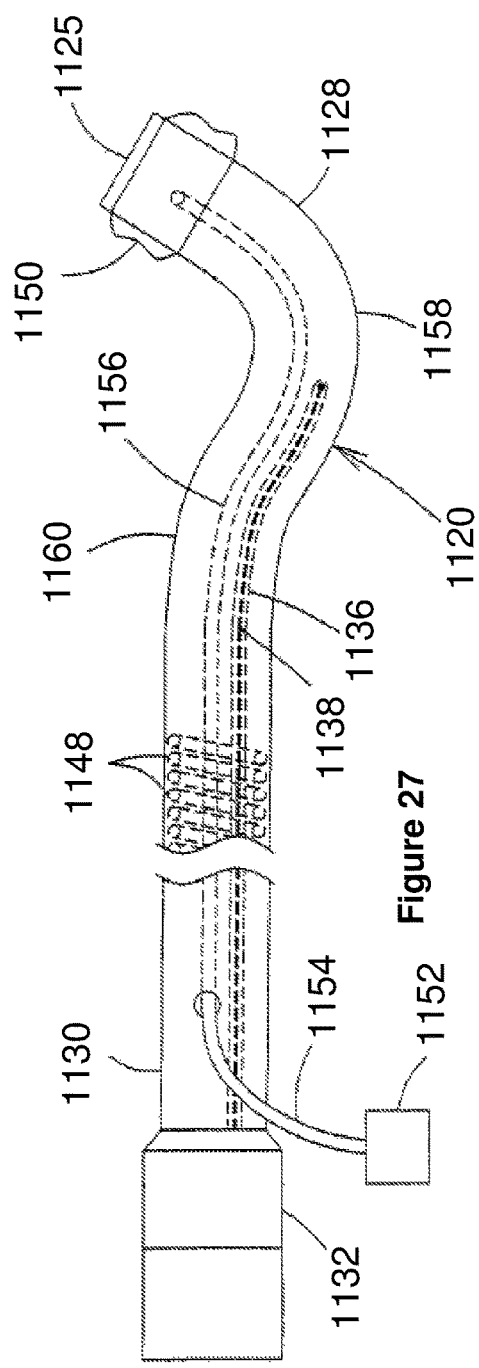
FIG. 27 corresponds to FIG. 8 of U.S. Ser. No. 09/280,988, and is a schematic side view of a steerable cannula having a preformed curve and an inflatable balloon formed at a distal end thereof in accordance with a fifth embodiment of U.S. Ser. No. 09/280,988.
Figure 28:
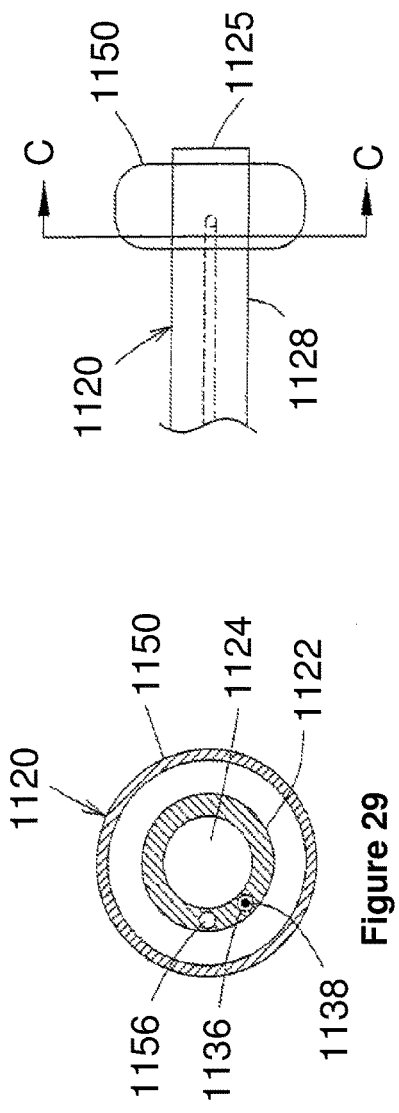
FIG. 28 corresponds to FIG. 9 of U.S. Ser. No. 09/280,988, and is a schematic side view of the inflatable balloon of a fifth embodiment of U.S. Ser. No. 09/280,988, wherein the balloon is shown in the inflated state.
Figure 29:
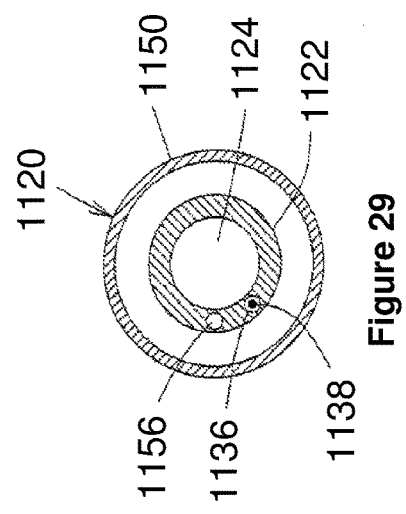
FIG. 29 corresponds to FIG. 10 of U.S. Ser. No. 09/280,988, and is a schematic cross-sectional view taken along line C-C of FIG. 28.
Figure 30:
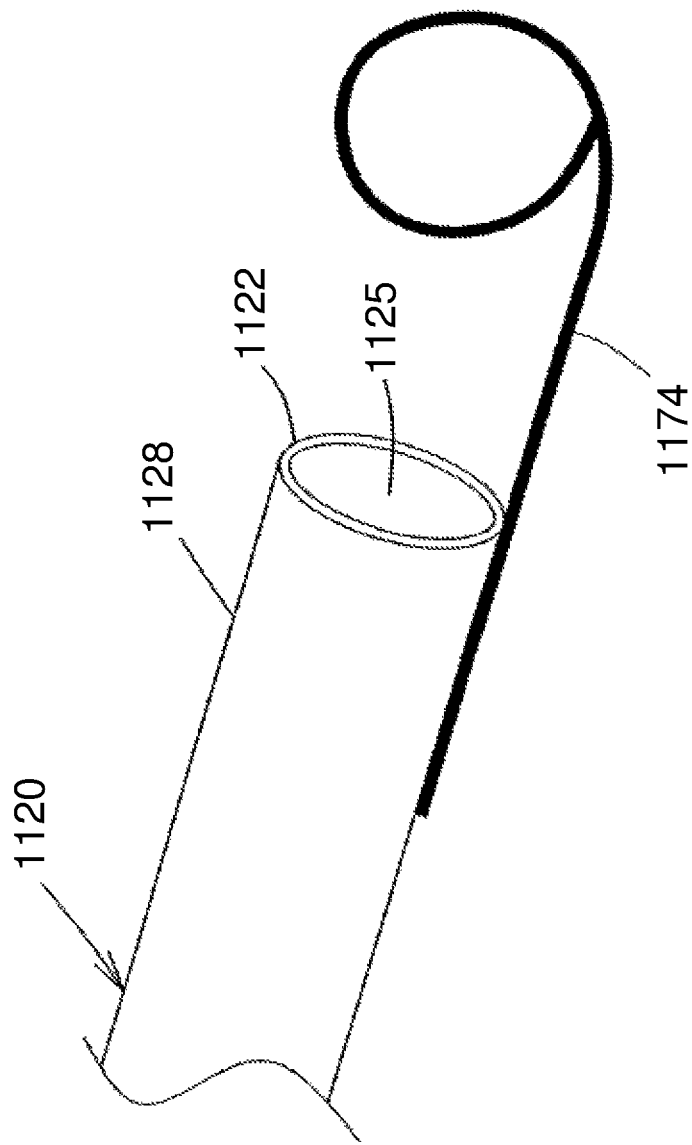
FIG. 30 corresponds to FIG. 11 of U.S. Ser. No. 09/280,988, and is a schematic view showing a steerable cannula having a pigtail distal tip configuration in accordance with a sixth embodiment of U.S. Ser. No. 09/280,988.
Figure 31:
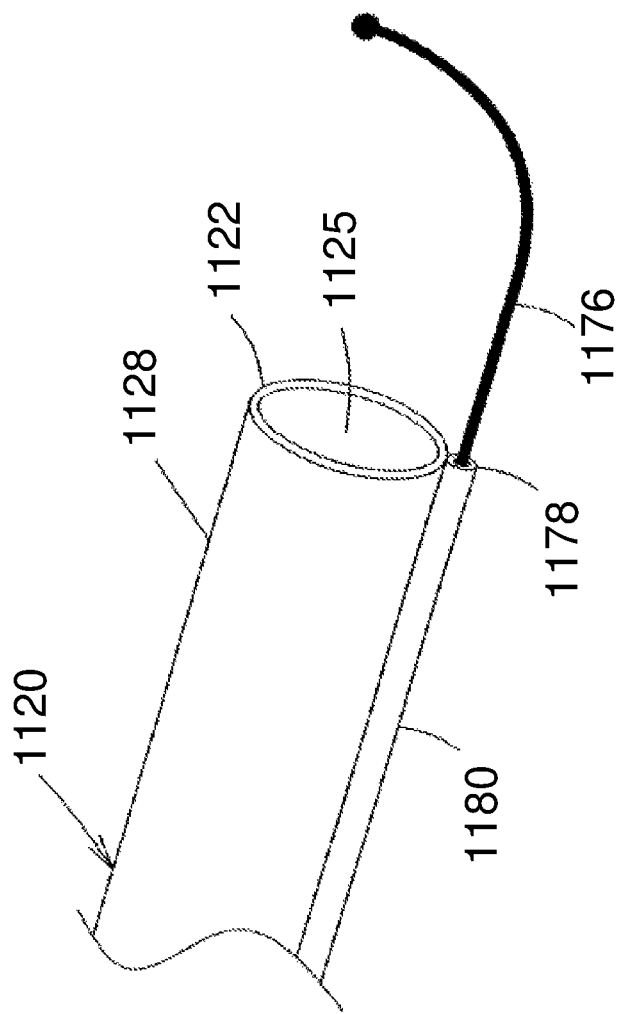
FIG. 31 corresponds to FIG. 12 of U.S. Ser. No. 09/280,988, and is a schematic view showing a steerable cannula having a guidewire distal tip configuration in accordance with a seventh embodiment of U.S. Ser. No. 09/280,988.
Figure 32:
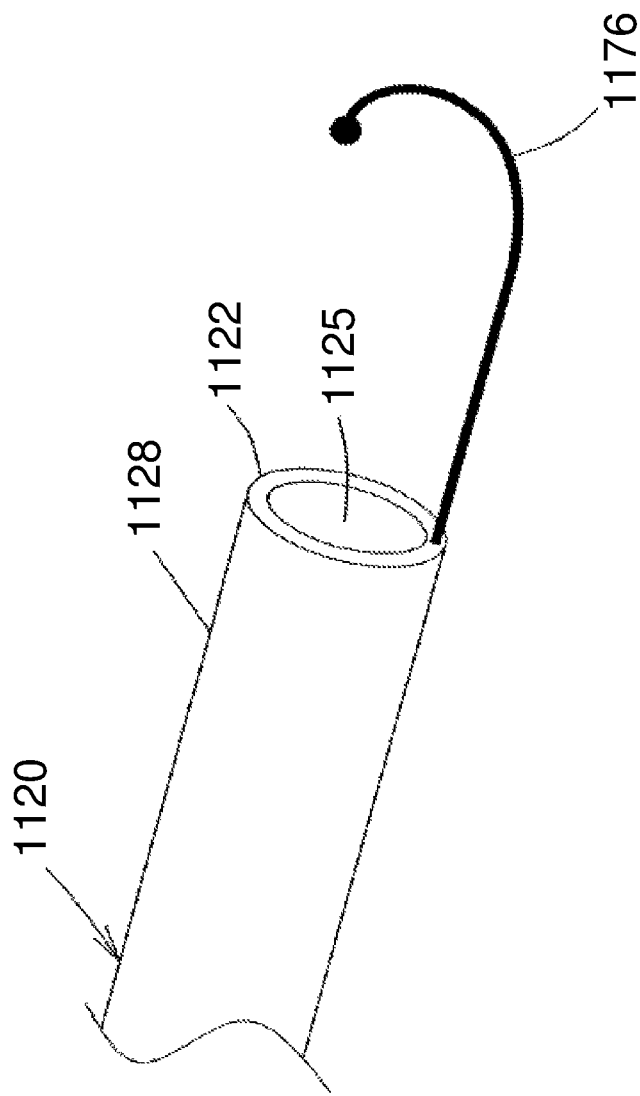
FIG. 32 corresponds to FIG. 13 of U.S. Ser. No. 09/280,988, and is a schematic view showing a steerable cannula having a guidewire distal tip configuration in accordance with an eighth embodiment of U.S. Ser. No. 09/280,988.
Figure 35:
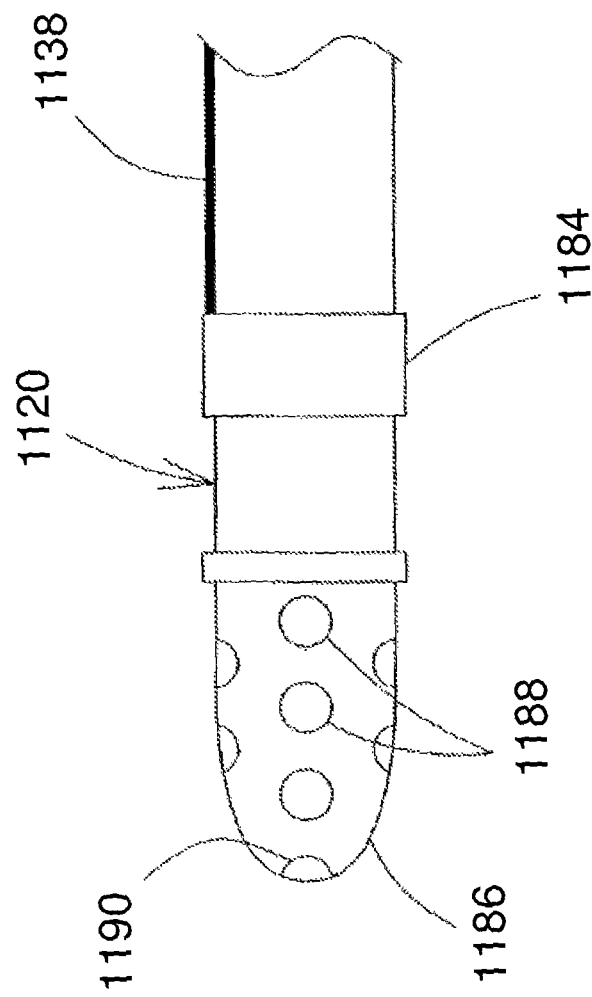
FIG. 35 corresponds to FIG. 16 of U.S. Ser. No. 09/280,988, and is a schematic side view of a configuration in accordance with a tenth embodiment of U.S. Ser. No. 09/280,988.

Many advantages of the present invention will be apparent to those skilled in the art with a reading of this specification in conjunction with the attached drawings, wherein like reference numerals are applied to like elements and wherein:

FIG. 20 is schematic side view of a steerable cannula in the undeformed state in accordance with the first embodiment of the invention;

FIG. 21 is a schematic cross-sectional view of the steerable cannula of FIG. 20 taken along line A-A;

FIG. 22 is a schematic side view of the steerable cannula in the deformed state in accordance with the first embodiment;

FIG. 23 is a schematic cross-sectional view of a steerable cannula having two cables in accordance with a second embodiment of the invention;

FIG. 24 is a schematic side view of a steerable cannula having a reinforcing wire in accordance with a third embodiment of the invention;

FIG. 25 is a schematic cut-away view of a steerable cannula in accordance with a fourth embodiment of the invention;

FIG. 26 is a schematic cross-sectional view taken along line B-B of FIG. 25;

FIG. 27 is a schematic side view of a steerable cannula having a preformed curve and an inflatable balloon formed at a distal end thereof in accordance with a fifth embodiment of the invention;

FIG. 28 is a schematic side view of the inflatable balloon of fifth embodiment of the invention, wherein the balloon is shown in the inflated state;

FIG. 29 is a schematic cross-sectional view taken along line C-C of FIG. 28;

FIG. 30 is a schematic view showing a steerable cannula having a pigtail distal tip configuration in accordance with a sixth embodiment of the invention;

FIG. 31 is a schematic view showing a steerable cannula having a guidewire distal tip configuration in accordance with a seventh embodiment of the invention;

FIG. 32 is a schematic view showing a steerable cannula having a guidewire distal tip configuration in accordance with an eighth embodiment of the invention;

FIG. 33 is a schematic side view showing a steerable cannula used in a co-axial configuration in accordance with a ninth embodiment of the invention, wherein the steerable cannula is advanced to a first relative position;

FIG. 34 is a schematic side view showing a steerable cannula of FIG. 33, wherein the steerable cannula is advanced to a second relative position; and FIG. 35 is a schematic side view of a configuration in accordance with a tenth embodiment of the invention.

DETAILED DESCRIPTION OF THE INVENTION

The present invention comprises a steerable cannula in which a portion which is adapted for insertion into the body of a patient, preferably into the vascular system of the patient, is configured to be selectively deformable. The deformation aids in changing the direction of the cannula during the insertion process such that the cannula can be steered in a desired direction as it is advanced toward its destination in the patient's body. Deformation is effected using a cable connected with the deformable portion of the cannula. Tension on the cable, induced by for example rotating a portion of a handle disposed at a proximal end of the cannula exterior of the body of the patient, results in tension on one wall of the deformable portion and thereby causes it to bend in the direction of the cable.

With reference to FIGS. 20-23 in which an exemplary arrangement in accordance with a first embodiment of the invention is shown, cannula 1120 can be seen as comprising a substantially cylindrical structure having a wall 1122 which defines a main lumen 1124. Lumen 1124 is adapted for fluid transport to or from the body of the patient and may be provided with one or more holes 1126 located adjacent to distal tip 1128 and permitting passage of fluid therethrough. Holes 1126 supplement fluid flow through main port 1125, especially in situations of blockage of main port 1125. Cannula 1120 may be one of two complementary cannulas (not shown) used in a surgical procedure, one for intake and the other for removal of blood or other fluid from the patient's body. Alternatively cannula 1120 may comprise a component of a co-axial, single port device in which cannula 1120 is surrounded by a second, larger conduit, with cannula 1120 for example operating to intake blood from the patient towards a pump system and the conduit operating to replace the blood from the pump back into the patient for augmentation of blood flow during beating heart surgery as described in co-pending PCT Application no. PCT/US97/18674 mentioned above.

At a proximal end 1130 of cannula 1120 is provided a handle 1132 which serves to transmit turning forces applied by an operator's hand to the cannula to aid in its manipulation in the patient's body. As such, handle 1132 is rigidly attached to wall 1122 of cannula 1120, although portions of handle 1132 may be configured for motion relative to cannula 1120 in order impart the necessary tension on cables used for deforming the cannula 1120 as described below. Rotation of the rigidly attached portion of handle 1132, results in a corresponding rotation of the distal end 1128 of the cannula 1120 within the patient's body, thus aiding in the cannula's manipulation and advancement to the desired destination.

Wall 1122, in addition to defining main lumen 1124 of cannula 1120, contains a secondary lumen 1136 formed therein. Movably mounted in lumen 1136 is a cable 1138 which is secured at point 1140 in wall 1122. Point 1140 may be disposed anywhere along the length of the cannula 1120, but in the preferred embodiment lies at distal end 1128.

Cannula 1120 is provided with a deformable portion 1142 formed along at least a segment of its length. In the exemplary arrangement shown in FIGS. 20-22, deformable portion 1142 is disposed in close proximity to distal end 1128 of cannula 1120; however, it is to be understood that this not intended to be limiting and that other regions in the cannula 1120 can alternatively or additionally be made deformable depending on the contemplated application.

Deformable portion 1142 serves to cause cannula 1120 to bend in response to tension applied to cable 1138 and thereby assume a configuration as shown in FIG. 22. Depending on the location of point 1140 and the location of lumen 1136 radially and axially along wall 1122, applied tension to cable 1138 causes cannula 1120 to turn on itself in the direction of pull to thereby assume a curve having a predetermined orientation. Additionally, if cannula 1120 is provided with one or more preformed curves, which may be in identical or in different planes along the length of the cannula as is contemplated, tension in cable 1138 can operate to temporarily straighten the cannula along at least one of these planes to facilitate handling during a particular maneuver through the patient's body.

It is also contemplated that more than one cable can be provided, supported in suitable secondary lumens formed in cannula 1120. As can be seen from FIG. 23, a second lumen 1146 can be provided in wall 1122 of cannula 1120, second lumen 1146 movably supporting cable 1144 therein. Cables 1138 and 1144 are thus disposed on opposite sides of cannula 1120 and serve to provide steerability in two directions. The cables are configured such that a pulling of one cable is coordinated with a slacking of the other cable in order permit bending of cannula 1120 at deformable portion 1142. Although shown to be diametrically opposed in position, cables 1138 and 1144 can occupy any position along wall 1122, and it will be appreciated that the number of such cables used can vary depending on the application, as can their distribution in wall 1122, and any desired number of turning directions can accordingly be achieved in accordance with the present invention.

Wall 1122 can be formed of materials ranging from rigid to flexible, and in the preferred embodiment comprises a semi-rigid transparent material such as silicone rubber. Of course it is to be understood that by definition deformable portion 1142 is to be constructed of a flexible material, regardless of the construction of the remainder of the wall 1122, such that cannula 1120 can bend when appropriate pulling forces are imparted through the cable(s).

Selective bending of cannula 1120 can also be facilitated using a core member provided for this purpose. Core member 1182, preferable formed of material having appreciable stiffness relative to wall 1122, is disposed longitudinally within cannula 1120 and serves to provide a deflection point to locate and control the bending point of the cannula. Core 1182 is removable and can be movable distally or proximally within cannula 1120 in order to alter the deflection point. In this manner also flow blockage in the cannula 1120 can be insured during insertion.

As can be seen from FIG. 24, a spiraling wire 1148 can be provided for structural reinforcement of cannula 1120. Wire 1148 is either molded into the wall 1122 or is otherwise supported therein, and extends either partially or fully across the length of the cannula 1120. Wire 1148 facilitates handling of the cannula 1120 and reduces the possibility of cannula 1120 collapsing or being pinched shut and thus closing off the flow of fluid to or from the patient. Other ways of reinforcing the tubular body of cannula 1120 are known in the art and will adapt equally well to the present invention. In addition, no reinforcement may be needed if the cannula material is sufficiently rigid or if sufficient fluid flow is present within the cannula.

Alternatively, as shown in FIGS. 25-26, spiraling wire 1148 can itself comprise a portion of cable 1138. In such an arrangement, cannula wall 1122 is formed of two layers 1162 and 1164, between which is formed a lumen 1166. Layers 1162 and 1164 may be discrete layers bonded together at appropriate regions, or they may be a single layer folded back upon itself to form the two layers, with lumen 1166 and wire 1148 occupying predetermined regions therebetween. Cable 1138 is housed in a polymide tube 1170 disposed in lumen 1166 and extends beyond the end 1168 of tube 1170 to then spiral exteriorly of inner layer 1162 and interiorly of outer layer 1164 to thereby lend structural support to the cannula 1120. Metal or other tape 1172 can be used to secure spiraling wire 1148 in place. In a variation of this, cable 1138 and wire 1148 may be two discrete components which are welded or otherwise connected together at any desired point along the body of cannula 1120. Alternatively, as shown in FIG. 35, cable 1138 may be secured to a band 1184 disposed radially about or adjacently to tip 1186 of cannula 1120. In all of these variations, cable 1138 may be formed of single or multiple strands of metal, plastic or carbon fiber composite, but preferably cable 1138 is formed of a single strand of stainless steel having a TEFLON™ coating. In the FIGS. 33-35 arrangements, cannula 1120 is shown with an atraumatic bullet tip 1186 having side holes 1188 and end holes 1190. It will be appreciated that such a tip can be provided for any arrangement of the invention. It will also be appreciated that the tip 1186 can itself serve as the anchor for the cable 1138 in certain arrangements. The tip 1186 is fixedly bonded to distal end 1125 of cannula 1120 and enables a simplified construction of the steering mechanism and provides a blunt surface that will not injure tissue in the body.

Lumens 1136 and 1146, or other similar lumens, in addition to supporting cables 1138 and 1144 therein, may be used to supply inflating fluid to a balloon 1150 provided at the outer surface of the distal end 1128 of cannula 1120. As shown in the exemplary embodiment of FIGS. 27-29, balloon 1150 is in fluid communication with inflating fluid source 1152, via supply tube 1154 and lumen 1156. Fluid source 1152 serves to selectively provide fluid, such as saline, air or other gas, to balloon 1150 to thereby cause the balloon to inflate within the patient's body. Balloon inflation in this manner assists in placement of the cannula 1120, especially when inserting the cannula antegrade, with the inflated balloon serving to float the tip of cannula within the fluid flow to thus transport it to the desired location in the body. Cannula 1120 is provided with one preformed curve 1158 in addition to curve 1160 imparted by the tension in cable 1138. Balloon 1150 is shown in the deflated state in FIG. 27 and in the inflated state in FIGS. 28 and 29.

Various distal tip configurations can be selected for cannula 1120, depending on the particular application as appreciated by those of ordinary skill in the art. For example, a pigtail shape can be used for crossing the aortic valve retrograde. The pigtail shape, illustrated in FIG. 30, can be formed by bonding or thermal welding or otherwise attaching a thermoplastic rod 1174 into a loop at the distal end of the cannula 1120. Alternatively, a J-tip wire 1176 can be configured to protrude from the distal tip 1128, as illustrated in FIGS. 31 and 32. The J-tip wire can be a conventional guidewire movable or fixedly supported in a dedicated lumen 1178 formed in a rigidly attached tube 1180 (FIG. 31), or it can be supported, rigidly or movably, between layers of material from which the wall 1122 of cannula 1120 is formed. Guidewires are known in the art and can for example be formed of windings of wire coiled around a core and having one or more preformed curves formed therein.

An embodiment in which cannula 1120 is used in a coaxial configuration is shown in FIGS. 33 and 34. Cannula 1120 serves as an inner cannula, passing through outer conduit 1180 while the two components are disposed in the patient's body. An important advantage of this arrangement is that outer conduit 1180 operates to vary the radius of curvature of inner cannula 1120 by providing a base point as the inner cannula 1120 is advanced. In this manner manipulation of the inner cannula 1120 and outer conduit 1180 is facilitated and advancement to the desired destination in the body of the patient is more efficiently accomplished.

The above are exemplary modes of carrying out the invention and are not intended to be limiting. It will be apparent to one of ordinary skill in the art that modifications thereto can be made without inventive departure from the spirit and scope of the invention.

ABSTRACT OF THE APPENDIX A

A steerable cannula is provided with at least one cable through which tension is communicated to a deformable portion of the cannula. The tension causes the cannula to bend at the deformable portion, enabling selective steering of the cannula during insertion into the body of the patient.

APPENDIX B—(U.S. SER. NO. 09/280,970)

Pressure Sensing Cannula

BACKGROUND OF THE INVENTION

Field of the Invention

The present invention relates to cannulas used in surgical applications, and more particularly, to a cannula equipped with a pressure/flow rate transducer.

Description of the Related Art

In medical applications and specifically in surgery, the list of uses for cannulas is exhaustive. One application involves the augmenting or supplementing of pulmonary blood flow through the beating heart during cardio-surgery by use of one or more cannulas involved in the intake and return of blood into the circulatory system. The cannulas interface between the patient's circulatory system and the mechanical pumps that power the augmentation procedure. Such an application is described in co-pending PCT Application no. PCT/US97/18674 entitled "Single Port Cardiac Support Apparatus", filed Oct. 14, 1997 and incorporated herein by reference in its entirety.

When performing cardiac surgery cannulas are placed within the patient's blood stream and used for inflow and outflow of blood or other fluids. If the operator wishes to determine the rate of fluid flow, either a catheter with appropriate sensors must also be placed in the patient's blood stream, or other sensors such as an external ultrasonic sensor as disclosed in U.S. Pat. No. 5,179,862 are used. A shortcoming of ultrasonic systems such as that described in U.S. Pat. No. 5,179,862 is that they require significant monitoring. Ultrasonic sensors also require that tubing of a specific diameter be used, thereby adding to the cost and complexity of the surgical procedure. Additionally, ultrasonic sensors are expensive and nondisposable, thereby adding to the cost of the surgical procedure.

Another method to measure flow rate is through the use of a thermodilution catheter. Thermodilution catheters require the infusion of a solution, typically saline, of a known temperature, with a distally disposed thermistor measuring the temperature change to determine the flow rate. This method is also expensive, increasing the cost of the surgical procedure. A second problem with using flow-sensing catheters, such as thermodilution catheters, is that they require the operator to place more incisions within the patient. The catheters must be placed so that they do not interfere with the inflow or out flow of the cannula. Visual markers along the length of the cannula may also be used to determine location, the greater the number of markers the more accurate the placement at the expense of quick readings due to the greater number of markings.

SUMMARY OF THE INVENTION

The present invention overcomes the deficiencies of the prior art by providing a cannula assembly having one or more pressure transducers coupled to a main lumen thereof. In accordance with a first embodiment, the pressure transducers are attached to the substantially tubular wall defining the main lumen.

In accordance with a second embodiment, a partial occlusion is provided in the cannula to increase the pressure drop across the main lumen. In this manner transducer signal is increased, and an improved differential pressure measurement signal achieved.

In accordance with a third embodiment of the invention, one or more pressure transducers are used in conjunction with a pair of coaxial cannulas for measuring pressure.

In accordance with at fourth embodiment of the invention, a differential pressure transducer is used, the differential pressure transducer being mounted in a dedicated secondary lumen in communication with the first lumen.

In accordance with a fifth embodiment of the invention, the secondary lumen housing the differential pressure transducer is disposed across a knee formed in the cannula to augment pressure measurement. Partial occlusions may also be provided for this purpose.

In accordance with a sixth embodiment of the invention, the secondary lumen housing the differential pressure transducer is formed integrally with the tubular wall defining the main lumen.

In accordance with a seventh embodiment of the invention, a soft, flexible tapered tip is provided at the distal end of the cannula. Such a configuration allows for easier negotiation through the patient's body during surgical procedure.

In accordance with an eighth embodiment of the invention, an inflatable balloon is provided at the distal end of the cannula. The inflatable balloon aids in transporting the cannula to the desired destination.

In accordance with a ninth embodiment of the invention, a guide wire lumen is provided for supporting a guide wire in the cannula. The guide wire is used as a predecessor step in the insertion of the cannula.

In accordance with a tenth embodiment of the invention, a light guide is supported in the cannula. The light guide conveys light to a predetermined portion of the cannula to thereby aid in the visualization and location of the cannula during the surgical procedure.

The invention realizes various advantages over the prior art, including a reduction in the number of incisions that a surgeon must make in performing surgical procedures, along with a reduction in the amount of foreign material introduced into the patient's body, while providing safe, rapid, accurate and cost-effective fluid flow rate measurements.

BRIEF DESCRIPTION OF THE DRAWINGS

Figure 36:
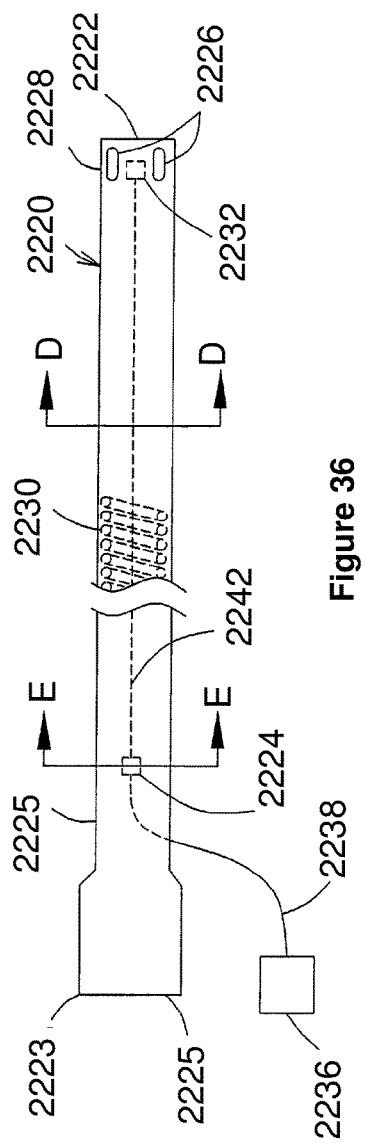
FIG. 36 corresponds to FIG. 1 of U.S. Ser. No. 09/280,970, and is a schematic side view of a first embodiment of U.S. Ser. No. 09/280,970.
Figure 38:
FIG. 38 corresponds to FIG. 3 of U.S. Ser. No. 09/280,970, and is a schematic cross-sectional view taken along line E-E of FIG. 36.
Figure 37:
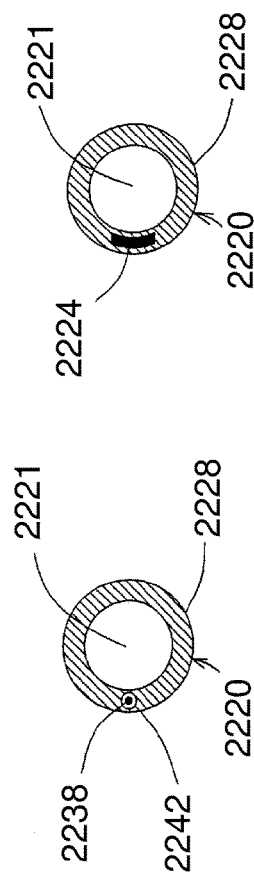
FIG. 37 corresponds to FIG. 2 of U.S. Ser. No. 09/280,970, and is a schematic cross-sectional view taken along line D-D of FIG. 36.
Figure 39:
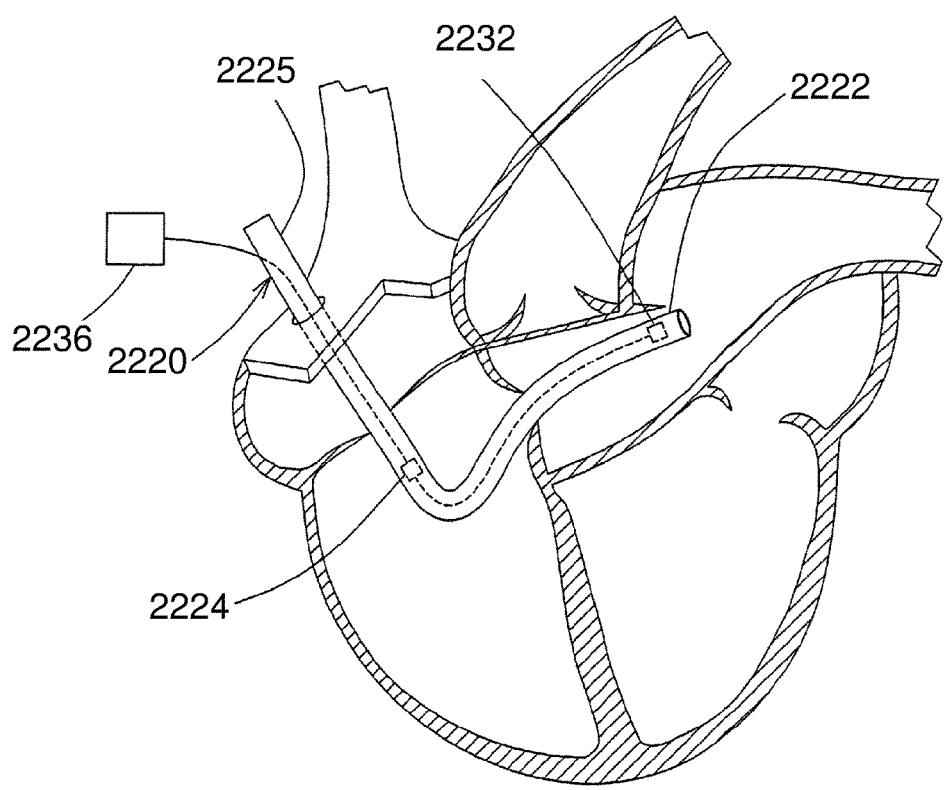
FIG. 39 corresponds to FIG. 4 of U.S. Ser. No. 09/280,970, and is a schematic view of a cannula in accordance with an embodiment in a surgical application.
Figure 40:
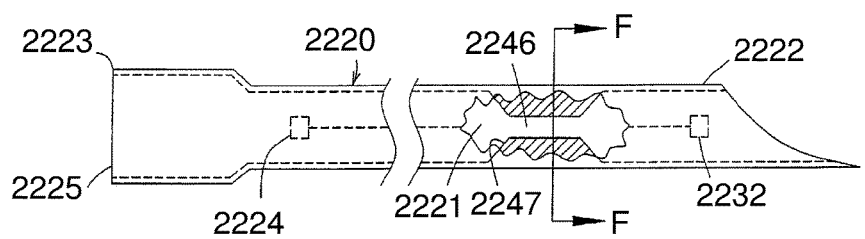
FIG. 40 corresponds to FIG. 5 of U.S. Ser. No. 09/280,970, and is a schematic partial cut-away side view of a second embodiment of U.S. Ser. No. 09/280,970.
Figure 41:
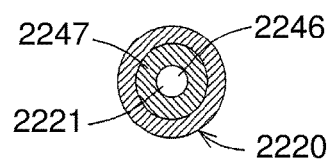
FIG. 41 corresponds to FIG. 6 of U.S. Ser. No. 09/280,970, and is a schematic cross-sectional view taken along line F-F of FIG. 40.
Figure 44:
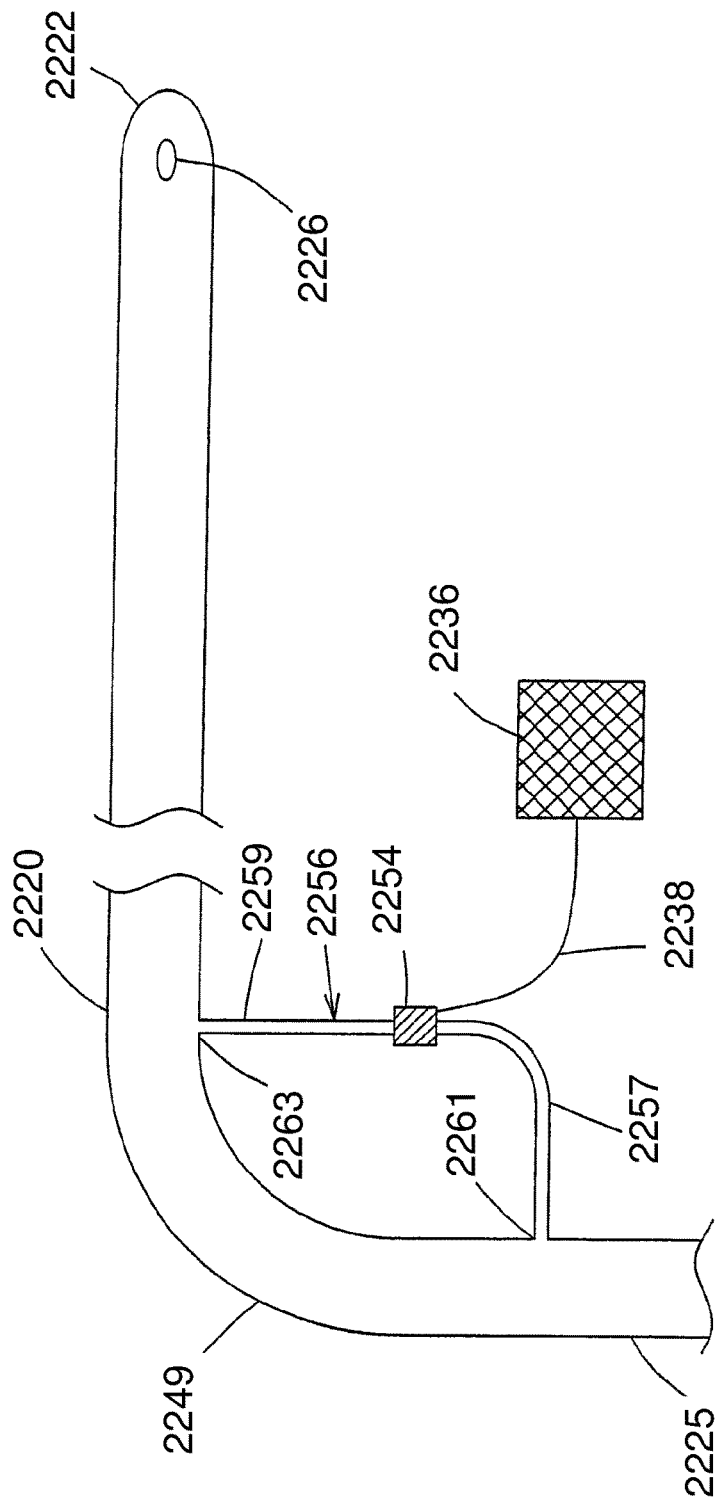
FIG. 44 corresponds to FIG. 9 of U.S. Ser. No. 09/280,970, and is a schematic side view of a fifth embodiment of U.S. Ser. No. 09/280,970.
Figure 45:
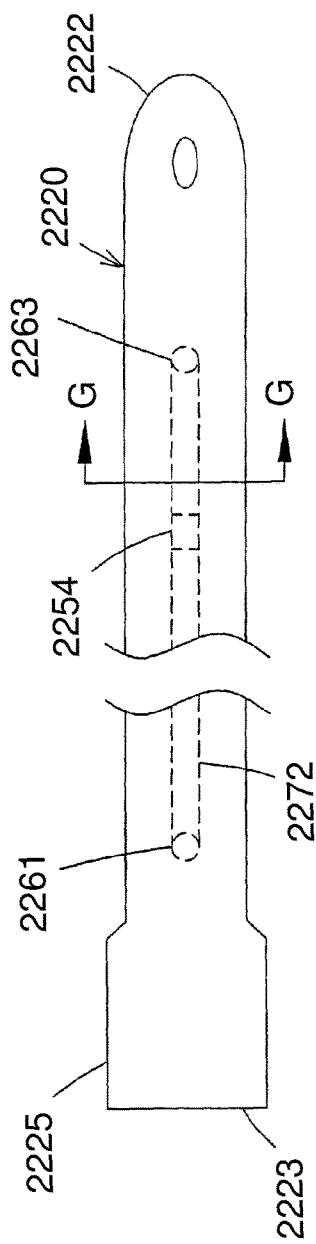
FIG. 45 corresponds to FIG. 10 of U.S. Ser. No. 09/280,970, and is a schematic side view of a sixth embodiment of U.S. Ser. No. 09/280,970.
Figure 46:
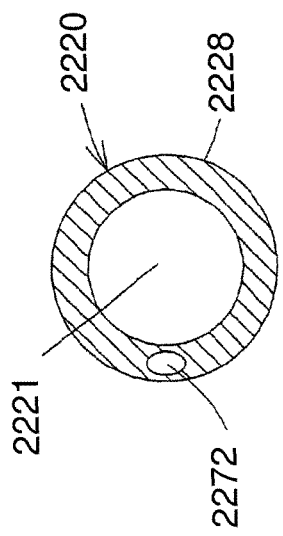
FIG. 46 corresponds to FIG. 11 of U.S. Ser. No. 09/280,970, and is a schematic cross sectional view taken along line G-G of FIG. 45.

Many advantages of the present invention will be apparent to those skilled in the art with a reading of this specification in conjunction with the attached drawings, wherein like reference numerals are applied to like elements and wherein:

FIG. 36 is a schematic side view of a first embodiment of the invention;

FIG. 37 is a schematic cross-sectional view taken along line D-D of FIG. 36;

FIG. 38 is a schematic cross-sectional view taken along line E-E of FIG. 36;

FIG. 39 is a schematic view of a cannula in accordance with the invention in a surgical application;

FIG. 40 is a schematic partial cut-away side view of a second embodiment of the invention;

FIG. 41 is a schematic cross-sectional view taken along line F-F of FIG. 40;

FIG. 42 is a schematic side view of a third embodiment of the invention;

FIG. 43 is a schematic side view of a fourth embodiment of the invention;

FIG. 44 is a schematic side view of a fifth embodiment of the invention;

FIG. 45 is a schematic side view of a sixth embodiment of the invention;

FIG. 46 is a schematic cross sectional view taken along line G-G of FIG. 45;

FIG. 47 is a schematic side view of a seventh embodiment of the invention;

FIGS. 48 and 49 are schematic side views of an eighth embodiment of the invention;

FIG. 50 is a schematic cross-sectional view taken along line H-H of FIG. 49:

FIG. 51 is a schematic side view of a ninth embodiment of the invention;

FIG. 52 is a schematic side view of a tenth embodiment of the invention; and

Figure 54:
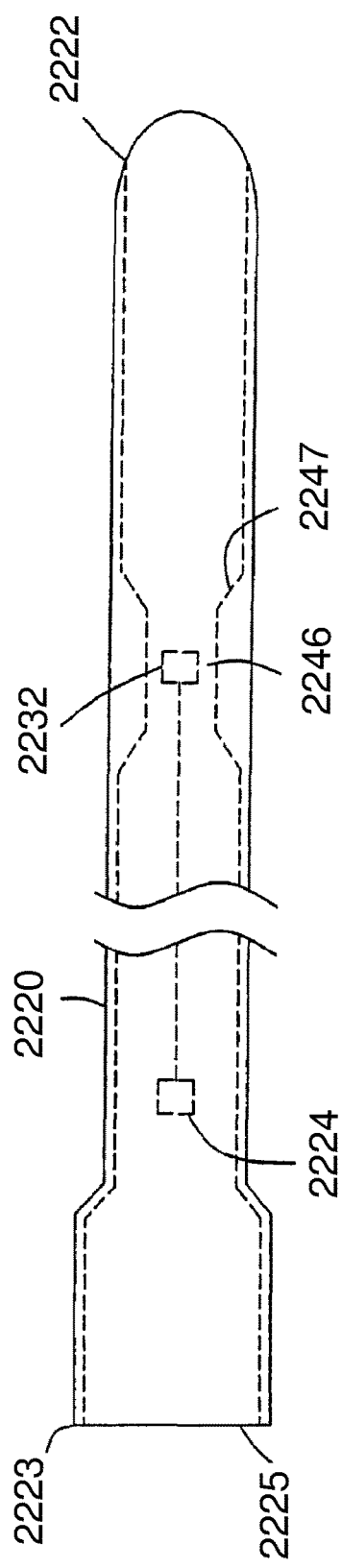
FIG. 54 corresponds to FIG. 19 of U.S. Ser. No. 09/280,970, and is a schematic side view of an eleventh embodiment of U.S. Ser. No. 09/280,970.

FIG. 53 is a schematic cross-sectional view taken along line K-K of FIG. 52; and FIG. 54 is a schematic side view of an eleventh embodiment of the invention.

DETAILED DESCRIPTION OF THE PREFERRED EMBODIMENTS

In accordance with the invention, a cannula comprising a substantially tubular, semi-flexible material adapted for fluid transport while inserted in a patient's body is provided with one or more pressure transducers which are fixedly or adjustably supported in the cannula. The pressure transducers are disposed internally or externally of the cannula and are used to provide a measurement of the rate of fluid flow. In the internal configuration, the rate of fluid flow within the cannula is measured. In the external configuration, the rate of fluid flow outside the cannula is measured. The cannula can also be adapted to support a guide wire to aid the operator in its insertion through the patient's body, and/or a light source to provide a visual reference during the insertion procedure. It is to be understood that the use of the term "cannula" is intended to encompass cannulas, catheters, and any related devices having similar application.

An exemplary arrangement in accordance with a first embodiment of the invention is shown FIGS. 36-38. Cannula 2220 comprises a substantially cylindrical structure having a wall 2228 defining a main lumen 2221. Wall 2228 can be formed of materials ranging from rigid to flexible, and in the preferred embodiment comprises a semi-rigid transparent material such as polyurethane, silicone rubber or other material. Lumens other than main lumen 2221 may also be provided, as described below. The cannula may also be formed from vinyl plastisol. To form a cannula of vinyl plastisol, a mandrel is dipped into liquid vinyl plastisol and heated. Wire is then wrapped around the mandrel and first formed layer. The mandrel is then dipped again encasing the wire, and then heated. The mandrel is then removed. Lumens and transducers may be formed within the wall of the cannula during the dipping process.

To lend structural support for the thin wall which allows maximum flow with minimal insertion damage, spiraling wire 2230 is provided for reinforcement and is either molded into the wall 2228 or is otherwise supported therein, and extends either partially or fully across the length of the cannula 2220. Wire 2230 facilitates handling of the cannula 2220 and reduces the possibility of cannula 2220 collapsing or being pinched shut and thus closing off the flow of fluid to or from the patient. Other ways of reinforcing the tubular body of cannula 2220 are known in the art and will adapt equally well to the present invention. In addition, no reinforcement may be needed if the cannula material is sufficiently rigid or if sufficient fluid flow is present within the cannula.

A connector 2223 is provided at the proximal 2225 end of cannula 2220. Connector 2223 is suitably sized to interface with various surgical instruments, including but not limited to a reverse flow pump or fluid conduits leading thereto (not shown). Cannula 2220 may also have one or more holes 2226 located adjacent to distal tip 2222 to facilitate fluid flow therethrough. Cannula 2220 may be one of two complementary cannulas used in a surgical procedure, one for intake and the other for removal of blood or other biocompatible fluid from the patient's body. Alternatively, cannula 2220 may comprise a component of a co-axial, single port device in which cannula 2220 is surrounded by a second, larger conduit, with cannula 2220 for example operating to intake blood from the patient towards a pump system and the conduit operating to replace the blood from the pump system back into the patient for augmentation of blood flow during beating heart surgery as described in the co-pending PCT Application No. PCT/US97/18674 mentioned above.

In order to provide real time fluid flow information in accordance with the present invention, a pair of pressure transducers 2224, 2232 are provided at two separate locations as illustrated in FIG. 36. Pressure transducers 2224, 2232 are of the type known in the art and each comprises for instance a piezo-electric crystal housed in an integrated circuit (IC) chip (not shown). The crystal configuration is designed to be pressure sensitive, generating an electrical signal in proportion to the amount of pressure experienced.

The principle governing the relationship between fluid flow and pressure is defined by Bernoulli's equation, herein solved for flow rate V and is determined by:

$$V = \sqrt{\frac{\Delta P \cdot 2d \cdot a^2}{f \cdot L \cdot \rho}}$$

where $\Delta P$ is the measured difference in pressure, d is the internal diameter of the lumen, a is the area of the lumen, f is a frictional factor of the lumen material. L is the lumen length over which the pressure measurement is conducted, and $\rho$ is a measurable constant representative of the density of the fluid. The flow rate information can be used for a variety of purposes, including monitoring the patient's condition and controlling the fluid pump used during the procedure.

In the preferred embodiment, transducers 2224, 2232 are imbedded in the wall 2228, which is formed for instance by application of successive layers of laminate and interjecting the transducers therebetween during the layering process. Depending on at what stage in the layering process the transducers 2224, 2232 are put in place in the wall 2228, their proximity to the interior of the cannula 2220 or its exterior can be controlled in order to optimize measurement of cannula interior or exterior pressure. From the interior pressure measurements, a determination of flow rate within main lumen 2221 can be made using the known diameter of the main lumen 2221. Similarly, from the exterior pressure measurements, flow rate of exterior fluid—for example, blood—can be measured if the diameter of the blood channel, such as the artery, is known, or the cannula can be calibrated with thermodilution catheters which assume the diameter of the vessel or artery they are placed within.

In the FIG. 36 exemplary arrangement, pressure transducer 2232 is disposed at a location near the distal tip 2222 of cannula 2220, while pressure transducer 2224 may be disposed anywhere along the length of cannula 2220 between pressure transducer 2232 and proximal end 2225. It is also contemplated that the pressure transducers 2224, 2232 may be detachably disposed in dedicated secondary lumens formed in or along tubular wall 2228, the dedicated secondary lumen extending to the proximal end 2225 and supporting any electrical cables connected to the pressure transducers 2224, 2232. In the detachable arrangement, the location of pressure transducers 2224, 2232 in the cannula 2220 can be adjusted to suit the particular application, such that one transducer can be disposed within one chamber of the heart while the other is at a different of portion of the heart to thereby provide a pressure/flow rate measurement of a predetermined portion of the patient's body, for example flow into the heart from a designated blood vessel. Such an application is shown in FIG. 39.

Pressure transducers 2224, 2232 are in electrical communication with console 2236 via cable 2238, which is supported in secondary lumen 4222 provided in cannula 2220. Calculations for determining fluid flow rate using signals generated by the pressure transducers 2224, 2232 and relayed via cable 2238 are conducted at the console 2236 or at any processor or processing system connected thereto.

As shown in FIGS. 40 and 41, cannula 2220 may also contain a partial occlusion portion 2247 that forms a venturi 2246 within the main lumen 2221 of cannula 2220. Venturi 2246, which may be disposed anywhere along the length of the cannula 2220, induces a pronounced pressure drop, creating a greater differential in pressure between proximal region 2225 and distal region 2222, thereby requiring less signal amplification of the pressure transducers and less filtering of the signal and consequently yielding a more accurate flow rate measurement. Preferably the location of the pressure transducer 2232 is in the vicinity of venturi 2246 as shown in FIG. 54.

FIG. 42 shows an embodiment in accordance with the invention in which the pressure transducers 2224, 2232 are used with a co-axial, single port device 2250 in which cannula 2220 is surrounded by a second, larger conduit 2248, with cannula 2220 for example operating to intake blood from the patient towards a pump system (not shown) and conduit 2248 operating to replace the blood from the pump system, via openings 2252, back into the patient for augmentation of blood flow during beating heart surgery as described in the co-pending PCT Application no. PCT/US97/18674 mentioned above. It is to be understood that pressure transducers 2224, 2232 can be mounted fixedly or detachably either to the interior or exterior of either the cannula 2220 or the conduit 2248 in the above-described manner. More than one pair of these transducers can also be used in a myriad possible combinations in accordance with the invention. In the preferred embodiment, the cannula 2220 is provided with a bullet nosed tip, as illustrated in for example FIGS. 42-44. Other tip configurations, such as a bevel, may also be used, as will be appreciated by those skilled in the art.

An alternative to using pairs of pressure transducers such as transducers 2224, 2232 is the use of a single differential pressure transducer 2254, as shown in FIG. 43. Differential pressure transducers are also well known in the art and comprise for example a piezo-electric crystal electro-mechanically configured to be responsive to a pressure difference between two opposing sides thereof. These two sides correspond respectively to proximal end 2257 and distal end 2259 of secondary lumen 2256 in which transducer 2254 is mounted. Proximal and distal ends 2257 and 2259 are attached at any desired points along the length of cannula 2220 to thereby couple secondary lumen 2256 to main lumen 2221 and provide a pressure difference measurement between the desired points. Attachment of lumen 2257 and transducer 2254 across knee 2249 of cannula 2220, as shown in FIG. 44, will provide a stronger signal, with knee 2249 operating in accordance with the same principal as venturi 2246 discussed above. Thus it is to be understood that a venturi could also be used in conjunction with the differential pressure transducer 2254. The ports 2261 and 2263 at which the lumen 2256 interfaces with cannula 2220 may be sealed by an appropriate membrane, with saline or other fluid being permanently housed in the lumen 2256. Alternatively, ports 2261 and 2263 may be open, permitting fluid communication between the cannula 2220 and the lumen 2256 and attached transducer 2254. The latter, open configuration would achieve a more faithful pressure representation. Stopcocks 2274 and 2276 can be provided in the ports 2261 and 2263 to permit priming and/or de-airing of the ports. It should also be noted that although in the arrangements of FIGS. 43 and 44 the lumen 2256 is provided as a separate tubular structure, lumen 2256 may alternatively be formed integrally with wall 2228 of cannula 2220, again with ports 2261 and 2263 being either open or closed to main lumen 2221 depending on the application. Such an arrangement is illustrated in FIGS. 45 and 46 in which is shown transducer 2254 in communication with lumen 2272 integrally formed in wall 2228 of cannula 2220.

Various distal tip configurations can be selected for cannula 2220 and used with the pressure sensing transducers, depending on the particular application as appreciated by those of ordinary skill in the art. FIG. 47 shows an exemplary embodiment in which the distal tip 2222 is formed of a soft, flexible material having a bullet shape. As shown exemplarily in FIGS. 48-50, the cannula 2220 may be equipped to support other tools, such as an inflatable balloon 2240 which is deployed for example in order to assist in transporting the distal tip 2222 to the desired destination in the patient's body during the surgical procedure. Balloon 2240 is inflated through an inflating lumen 2244 provided in cannula 2220 using a bio-compatible fluid such as saline or carbon dioxide gas. Preferably inflating lumen 2244 is formed integrally within wall 2228, by leaving an appropriate gap during the fabrication process, and is provided with a fitting (not shown) at its proximal end to interface with an inflating device for supplying the bio-compatible fluid. The lumen 2221 within the cannula 2220 can also be adapted to support a balloon catheter (not shown) which can be used to place the cannula within the patient's body. An obturator (not shown) may also be disposed through the main lumen 2221 to aid in insertion and guiding within the patient's body.

Another tool which cannula 2220 may support is shown in FIG. 51 and comprises a J-hook guidewire 2262 disposed slideably within lumen 2264, which is formed integrally in wall 2228 of cannula 2220. In operation, guidewire 2262, easier to manipulate than the cannula 2220, is first inserted into the patient's body and manipulated to the surgical site. Subsequently the cannula 2220 is maneuvering along the guidewire 2262, which passes through lumen 2264, to the desired destination.

As illustrated in FIGS. 52 and 53, cannula 2220 may also contain a light guide 2266, which may be supported in lumen 2268. Light guide 2266 comprises one or more optical fibers formed of, for example, glass or other materials, such as plastic, known for that purpose. Distal tip of light guide 2266 is configured for light projection, such that light provided at the proximal end of light guide 2266 is projected therefrom. An appropriate shape for such projection is a spherical shape, although other shapes and projection schemes, such as directional projection, fall within the purview of the invention. The source of light may be any conventional monochromatic (laser/LED) or polychromatic device 2270, and more than one light source with associated light guide can be used for color coding and providing a visual reference to different portions of the cannula 2220, depending on the colors of light used and on the location of the projection terminus of the light guides. In this manner cannula 2220 can be visually guided through the patient's body, relying on the transmissivity of tissue to permit the location of the illuminated cannula in the patient's body. As will be appreciated, the location of the cannula 2220 can also be determined by examining the pressure waveform detected by the pressure transducers 2224, 2232 and 2254. The physiological pressure waveform recorded by the transducers can be used to determine the location of cannula 2220 in relation to the valves of the patient's heart.

As will be appreciated by those skilled in the art, cannula 2220 may be provided with one or more preformed curves along its length to aid in its manipulation through the patient's vasculature. Multiple curves may be disposed along the same plane or in different planes, depending on the application.

An additional feature in accordance with the invention is the use of radiopaque markings (not shown) anywhere along the cannula body. Such markings render portions of the cannula 2220 visible to x-ray radiation for visualizing the cannula during its use.

The above are exemplary modes of carrying out the invention and are not intended to be limiting. It will be apparent to those skilled in the art that modifications thereto can be made without departure from the spirit and scope of the invention. It will also be apparent that all devices and methods herein disclosed will adapt equally to animal use as well as human use.

ABSTRACT OF APPENDIX B

A cannula is provided with one or more pressure transducers for measuring fluid pressure interiorly or exteriorly of the cannula. The pressure transducers may be mounted integrally with the tubular wall defining the main lumen of the cannula, or they may comprise differential pressure transducers mounted in dedicated lumens in communication with the main lumen. The pressure measurements from the transducers is used to determine fluid flow rate.

What is claimed is:

1. An intravascular blood pump system, comprising:
    a blood pump adapted to be guided to a predetermined location within a circulatory system of a patient by a guide wire and configured to provide left-heart support, the blood pump comprising a rotor having a rotor hub and at least one blade extending outward from the rotor hub;
    a rotor shroud at least partially disposed about the rotor hub;
    an elongate catheter extending proximally with respect to the blood pump;
    a cannula extending from the rotor shroud and comprising an outer cannula surface, the outer cannula surface having a substantially circular cross-section along a portion of its length, wherein a distal portion of the rotor shroud having an outer diameter matching an inner diameter of a proximal portion of the cannula, the proximal portion of the cannula disposed about a distal portion of the rotor shroud; and
    one or more first ports and one or more second ports establishing fluid communication between a cannula lumen and an exterior region of the cannula, wherein at least one first port of the one or more first ports is located in proximity to the rotor and at least one second port of the one or more second ports is spaced apart from and located distal to the at least one first port, wherein the cannula is configured such that when the blood pump is positioned in the patient to provide left-heart support a distal end of the cannula and the at least one second port are positioned inside the patient's heart and a proximal end of the cannula and the at least one first port are positioned in the patient's aorta, and the blood pump is configured to draw blood from the patient's heart into the at least one second port through the cannula lumen and out the at least one first port to provide left-heart support while the cannula is positioned across an aortic valve of the patient.

2. The intravascular blood pump system of claim 1, further comprising a pressure sensing element configured to sense pressure proximate the blood pump, wherein the pressure sensing element comprises at least one of a piezoelectric pressure sensing element and a strain gauge.

3. The intravascular blood pump system of claim 2, wherein the pressure sensing element is adjacent to the one or more first ports.

4. The intravascular blood pump system of claim 1, further comprising an elongate lumen sized to slidably receive the guide wire and dimensioned such that the guide wire passes slidably through the elongate lumen, the elongate lumen is sized smaller cross sectionally than the cannula lumen and is shorter in length than the cannula, and wherein the elongate lumen is at least one of an integral extension of a wall of the cannula and at least partially disposed within an outer surface of the cannula.

5. The intravascular blood pump system of claim 4, further comprising:
    a motor assembly and a drive cable,
    wherein the motor assembly and drive cable are configured to drive the rotor,
        wherein the elongate lumen is proximal to the cannula and the motor assembly is configured to remain external to the patient, and
        wherein the intravascular blood pump system comprises a dual construction arrangement whereby the rotor is configured to be docked within the rotor shroud.

6. An intravascular blood pump system, comprising:
a blood pump adapted to be guided to a predetermined location within a circulatory system of a patient by a guide wire and configured to provide left-heart support, the blood pump comprising a rotor having a rotor hub and at least one blade extending outward from the rotor hub;
a rotor shroud at least partially disposed about the rotor hub;
an elongate catheter extending proximally with respect to the blood pump;
a cannula extending from the rotor shroud and comprising an outer cannula surface, the outer cannula surface having a substantially circular cross-section along a portion of its length, wherein at least a proximal portion of the rotor shroud has the same outer diameter as a proximal portion of the cannula, the proximal portion of the cannula disposed about a distal portion of the rotor shroud; and
one or more first ports and one or more second ports establishing fluid communication between a cannula lumen and an exterior region of the cannula, wherein at least one first port of the one or more first ports is located in proximity to the rotor and at least one second port of the one or more second ports is spaced apart from and located distal to the at least one first port, wherein the cannula is configured such that when the blood pump is positioned in the patient to provide left-heart support a distal end of the cannula and the at least one second port are positioned inside the patient's heart and a proximal end of the cannula and the at least one first port are positioned in the patient's aorta, and the blood pump is configured to draw blood from the patient's heart into the at least one second port through the cannula lumen and out the at least one first port to provide left-heart support while the cannula is positioned across an aortic valve of the patient.

7. The intravascular blood pump system of claim 6, further comprising a pressure sensing element configured to sense pressure proximate the blood pump, wherein the pressure sensing element comprises at least one of a piezoelectric pressure sensing element and a strain gauge.

8. The intravascular blood pump system of claim 7, wherein the pressure sensing element is adjacent to the one or more first ports.

9. The intravascular blood pump system of claim 6, further comprising an elongate lumen sized to slidably receive the guide wire and dimensioned such that the guide wire passes slidably through the elongate lumen, the elongate lumen is sized smaller cross sectionally than the cannula lumen and is shorter in length than the cannula, and wherein the elongate lumen is at least one of an integral extension of a wall of the cannula and at least partially disposed within an outer surface of the cannula.

10. The intravascular blood pump system of claim 9, further comprising:
a motor assembly and a drive cable,
wherein the motor assembly and drive cable are configured to drive the rotor,
wherein the elongate lumen is proximal to the cannula and the motor assembly is configured to remain external to the patient, and
wherein the intravascular blood pump system comprises a dual construction arrangement whereby the rotor is configured to be docked within the rotor shroud.

11. An intravascular blood pump system, comprising:
a blood pump adapted to be guided to a predetermined location within a circulatory system of a patient by a guide wire and configured to provide left-heart support, the blood pump comprising a rotor having a rotor hub and at least one blade extending outward from the rotor hub;
a rotor shroud at least partially disposed about the rotor hub;
an elongate catheter extending proximally with respect to the blood pump;
a cannula extending from the rotor shroud and comprising an outer cannula surface, the outer cannula surface having a substantially circular cross-section along a portion of its length;
one or more first ports and one or more second ports establishing fluid communication between a cannula lumen and an exterior region of the cannula, wherein at least one first port of the one or more first ports is located in proximity to the rotor and at least one second port of the one or more second ports is spaced apart from and located distal to the at least one first port, wherein the cannula is configured such that when the blood pump is positioned in the patient to provide left-heart support a distal end of the cannula and the at least one second port are positioned inside the patient's heart and a proximal end of the cannula and the at least one first port are positioned in the patient's aorta, and the blood pump is configured to draw blood from the patient's heart into the at least one second port through the cannula lumen and out the at least one first port to provide left-heart support while the cannula is positioned across an aortic valve of the patient; and
a pigtail shaped distal tip or a J-shaped distal tip, wherein a proximal end of the pigtail shaped distal tip or the J-shaped distal tip is fixed or attached to a distal end of the cannula and the pigtail shaped distal tip or the J-shaped distal tip is distal to each of the one or more second ports.

12. The intravascular blood pump system of claim 11, wherein a proximal linear portion of the pigtail shaped distal tip or the J-shaped distal tip is adjacent to the one or more second ports.

13. The intravascular blood pump system of claim 11, further comprising a pressure sensing element configured to sense pressure proximate the blood pump, wherein the pressure sensing element comprises at least one of a piezoelectric pressure sensing element and a strain gauge.

14. The intravascular blood pump system of claim 13, wherein the pressure sensing element is adjacent to the one or more first ports.

15. The intravascular blood pump system of claim 11, further comprising an elongate lumen sized to slidably receive the guide wire and dimensioned such that the guide wire passes slidably through the elongate lumen, the elongate lumen is sized smaller cross sectionally than the cannula lumen and is shorter in length than the cannula, and wherein the elongate lumen is at least one of an integral extension of a wall of the cannula and at least partially disposed within an outer surface of the cannula.

16. The intravascular blood pump system of claim 15, further comprising:
a motor assembly and a drive cable,
wherein the motor assembly and drive cable are configured to drive the rotor,
wherein the elongate lumen is proximal to the cannula and the motor assembly is configured to remain external to the patient, and wherein the intravascular blood pump system comprises a dual construction arrangement whereby the rotor is configured to be docked within the rotor shroud.

17. An intravascular blood pump system, comprising:
a blood pump adapted to be guided to a predetermined location within a circulatory system of a patient by a guide wire and configured to provide left-heart support, the blood pump comprising a rotor having a rotor hub and at least one blade extending outward from the rotor hub;
a rotor shroud at least partially disposed about the rotor hub;
an elongate catheter extending proximally with respect to the blood pump;
a cannula extending from the rotor shroud and comprising an outer cannula surface, the outer cannula surface having a substantially circular cross-section along a portion of its length;
one or more first ports and one or more second ports establishing fluid communication between a cannula lumen and an exterior region of the cannula, wherein at least one first port of the one or more first ports is located in proximity to the rotor and at least one second port of the one or more second ports is spaced apart from and located distal to the at least one first port, wherein the cannula is configured such that when the blood pump is positioned in the patient to provide left-heart support a distal end of the cannula and the at least one second port are positioned inside the patient's heart and a proximal end of the cannula and the at least one first port are positioned in the patient's aorta, and the blood pump is configured to draw blood from the patient's heart into the at least one second port through the cannula lumen and out the at least one first port to provide left-heart support while the cannula is positioned across an aortic valve of the patient; and
a pressure sensing element configured to sense pressure proximate the blood pump, wherein the pressure sensing element comprises a fluid column and at least one of a piezo-electric pressure sensing element and a strain gauge associated with the fluid column.

18. The intravascular blood pump system of claim 17, further comprising a pigtail shaped distal tip or a J-shaped distal tip, wherein a proximal end of the pigtail shaped distal tip or the J-shaped distal tip is fixed or attached to a distal end of the cannula and the pigtail shaped distal tip or the J-shaped distal tip is distal to each of the one or more second ports.

19. The intravascular blood pump system of claim 18, wherein a proximal linear portion of the pigtail shaped distal tip or the J-shaped distal tip is adjacent to the one or more second ports.

20. The intravascular blood pump system of claim 17, wherein a distal portion of the rotor shroud having an outer diameter matching an inner diameter of a proximal portion of the cannula, the proximal portion of the cannula disposed about a distal portion of the rotor shroud, and at least a proximal portion of the rotor shroud has the same outer diameter as the proximal portion of the cannula.

21. The intravascular blood pump system of claim 17, wherein the pressure sensing element is adjacent to the one or more first ports.

22. The intravascular blood pump system of claim 17, further comprising an elongate lumen sized to slidably receive the guide wire and dimensioned such that the guide wire passes slidably through the elongate lumen, the elongate lumen is sized smaller cross sectionally than the cannula lumen and is shorter in length than the cannula, and wherein the elongate lumen is at least one of an integral extension of a wall of the cannula and at least partially disposed within an outer surface of the cannula.

23. The intravascular blood pump system of claim 22, further comprising:
a motor assembly and a drive cable,
wherein the motor assembly and drive cable are configured to drive the rotor,
wherein the elongate lumen is proximal to the cannula and the motor assembly is configured to remain external to the patient, and
wherein the intravascular blood pump system comprises a dual construction arrangement whereby the rotor is configured to be docked within the rotor shroud.

* * * * *